(12) United States Patent
Witte et al.

(10) Patent No.: US 6,709,830 B2
(45) Date of Patent: Mar. 23, 2004

(54) METHODS FOR MODULATING THE ACTIVATION OF A LYMPHOCYTE EXPRESSED G PROTEIN COUPLED RECEPTOR INVOLVED IN CELL PROLIFERATION, AUTOIMMUNITY AND INFLAMMATION

(75) Inventors: Owen N. Witte, Sherman Oaks, CA (US); Zhigang Weng, Brookline, MA (US); Lu Q. Le, Los Angeles, CA (US); Janusz H. S. Kabarowski, Los Angeles, CA (US); Yan Xu, Pepper Pike, OH (US); Kui Zhu, Richmond Heights, OH (US)

(73) Assignee: The Regents of the University of California, Oakland, CA (US)

( * ) Notice: Subject to any disclaimer, the term of this patent is extended or adjusted under 35 U.S.C. 154(b) by 470 days.

(21) Appl. No.: 09/796,266

(22) Filed: Feb. 28, 2001

(65) Prior Publication Data

US 2002/0051980 A1 May 2, 2002

Related U.S. Application Data

(63) Continuation-in-part of application No. 09/553,875, filed on Apr. 20, 2000, now Pat. No. 6,514,696, which is a continuation-in-part of application No. 09/120,025, filed on Jul. 17, 1998, now Pat. No. 6,214,562, which is a continuation-in-part of application No. 08/969,815, filed on Nov. 13, 1997, now Pat. No. 6,207,412.

(51) Int. Cl.[7] .................. G01N 33/50; C12N 15/12; C12N 15/63
(52) U.S. Cl. .................. 435/7.1; 435/7.2; 435/7.21; 435/69.1; 435/325; 435/172.3; 435/252.3; 536/24.3; 536/23.1
(58) Field of Search .................. 435/7.1, 7.2, 7.21, 435/69.1, 325, 172.3, 252.3; 536/24.3, 23.1

(56) References Cited

FOREIGN PATENT DOCUMENTS

WO   WO 99/25830   5/1999

OTHER PUBLICATIONS

Mahadevan, M. S. et al., Isolation of a novel G protein coupled receptor, PIR 76 Database, Accession No. B57641, Feb. 8, 1996.*

Mahadevan, M. S. et al., Isolation of a novel G protein coupled receptor, Swissprot 41 Database, Accession No.P50132, Nov. 1, 1996.*

J.H.S. Kabarowski et al., 2000, "Direct genetic demonstration of . . . rearrangement," PNAS, 97(22):12109–12114, 2000.

I.F. Zohn et al., 2000, "G2A is an oncogenic G protein–coupled receptor," Oncogene (2000) 19:3866–3877, 2000.

W.H. Moolenaar, 1999, "Bioactive Lysophospholipids and Their G Protein–Coupled Receptors," Experimental Cell Research 253:230–238, 1999.

Choe et al., "The β–Chemokine . . . Isolates," Cell, 85:1135–1148, 1996.

R.J. Davis, "Transcriptional Regulation by MAP Kinases," Molecular Reproduction and Development, 42:459–467, 1995.

Deng et al., "Identification of a major co–receptor for primary isolates of HIV–1" Nature, 381:661–666, 1996.

Choi et al., "Identification of a Putative G Protein . . . Cells," Cellular Immunology, 168:78–84, 1996.

Doranz et al., "A Dual–Tropic Primary . . . Cofactors," Cell, 85:1148–1158, 1996.

Dragic et al., "HIV–1 entry into CD4[+] cells . . . CC–CKR–5," Nature, 381:667–673, 1996.

Feng et al., "HIV–1 Entry Cofactor: Functional cDNA . . . Receptor," Science, 272:872–877, 1996.

Forster et al., "A Putative Chemokine Receptor . . . Spleen," Cell, 87:1037–1047, 1996.

M.L.X. Fu, "Characterization of anti–heart M2 muscarinic . . . study," Molecular and Cellular Biochemistry, 163/164:343–347, 1996.

Goga et al., "Alternative Signals to RAS for Hematopoietic . . . Oncogene," Cell, 82:981–988, 1995.

Hubank et al., "Identifying differences in mRNA expression . . . cDNA," Nucleic Acids Research, 22(25):5640–5648, 1996.

Koshiba et al., "Transient up–regulation of $P2Y_2$ nucleotide . . . thymocytes," Proc. Natl. Acad. Sci. USA, 94:831–836, 1997.

Kurzrock et al., "The Molecular Genetics of . . . Leukemias," The New England Journal of Medicine, 319(15):990–998, 1988.

Lugo et al., "The BCR0ABL Oncogene . . . v–myc," Molecular and Cellular Biology 9(3):1263–1270, 1989.

McLaughlin et al., "Alternative Forms of the . . . Cells," Molecular and Cellular Biology, 9(5):1866–1874, 1989.

(List continued on next page.)

Primary Examiner—Yvonne Eyler
Assistant Examiner—Nirmals Basi
(74) Attorney, Agent, or Firm—Gates & Cooper LLP

(57) ABSTRACT

The invention provided herein describes ligands and methods for modulating a G protein-coupled receptor (GPCR), designated G2A, a lymphocyte expressed receptor whose genetic ablation results in the development of autoimmunity. The present disclosure teaches that lysophosphatidylcholine (LPC) is a high affinity ligand for G2A and that sphingosylphosphorylcholine (SPC) is a lower affinity ligand for G2A. As G2A activation is shown to be involved in a variety of physiological processes including cell proliferation, autoimmunity and inflammation, methods which modulate its activity have a variety of diagnostic and therapeutic applications.

15 Claims, 27 Drawing Sheets

OTHER PUBLICATIONS

Muller et al., "BCR First Exon Sequences . . . Leukemias," Molecular and Cellular Biology, 11(4):1785–1792, 1991.

P.M. Murphy, "The Molecular Biology . . . Receptors," Annu. Rev. Immunol., 12:593–633, 1994.

Pear et al., "Production of high–titer helper–free . . . transfection," Proc. Natl. Acad. Sci. USA 90:8392–8396, 1993.

Pendergast et al., "BCR–ABL–Induced Oncogenesis . . . Protein," Cell, 75:175–185, 1997.

Schneider et al., "Genes Specifically Expressed . . . Cells," Cell, 54:787–793, 1988.

Strader et al., "The family of G–protein–coupled receptors," The FASEB Journal, 9:745–754, 1995.

Strader et al., "Structure and Function of G Protein–Coupled Receptors," Annu. Rev. Biochem., 63:101–132, 1996.

Tsukada et al., "Deficient Expression of a . . . Agammaglobulinemia," Cell 72:279–290, 1993.

Lisitsyn et al., "Cloning the Differences Between . . . Genomes," Science 259:946–951, 1997.

Libert et al., "Selective Amplitication and Cloning . . . Family," Science, 244:569–572, 1989.

Bouvier et al., "Dynamic Palmitoylation of G–Protein . . . Cells," Methods in Enzymology, Academic Press, pp. 300–314, 1995.

* cited by examiner

ALIGNMENT OF MOUSE AND HUMAN GPCRS

```
  1 MRSEPTNAAGNTTLGVTSVLQSTSVPSSETCHVSYEESRVVLVVVYSAVC   50 MOUSE
    |  . .:..|:||.|:: ...:: :..|:|||||.|||||||||||
  4 MLLKNGYNGNATPVTTAPWASLGLSAKTCNNVSFEESRIVLVVVYSAVC   53 HUMAN

51 LLGLPANCLTAWLTLLQVLQRNVLAVLFCLSLCELLYISTVPLWIIYIQ  100 MOUSE
    |:|:|||||||||.|||.||||||||||:|.|.|||||.:|:|:|:|.
 54 TLGVPANCLTAWLALLQVLQGNVALVLLCLALCELLYTGTLPLWVIYIR  103 HUMAN

101 NQHKWNLGPQACKVTAYIFFCNIYISILLCCISCDRYMAVVYALESRGH  150 MOUSE
    |||:|.||:.|||||||||||||||:||||||||||::|||||||||:
104 NQHRWTLGLLACKVTAYIFFCNIYVSILFLCCISCDRFVAVVYALESRGR  153 HUMAN

151 RHQRTAVTISACVILLVGLVNYPVFDMKVEKSFCFEPLRMNSKIAGYHYL  200 MOUSE
    |:..|||:|||:|||:||:|:||||::.|:  :|.:.|:|||||.|||||
154 RRRRTAILISACIFILVGIVHYPVFQTE.DKETCFDMLQMDSRIAGYYYA  202 HUMAN

201 RFTFGFAIPLGILAFTNHQIFRSIKLSDSLSAAQKNKVKRSAIAVVTIFL  250 MOUSE
    ||| ||||||.|||||||:|||||||:|||||||:||:||||||:||||
203 RFTVGFAIPLSIIAFTNHRIFRSIKQSMGLSAAQKAKVKHSAIAVVVIFL  252 HUMAN

251 VCFAPYHVLLVKAASFSFYQGDMDAVCAFESRLYTVSMVFLCLSTVNSV  300 MOUSE
    ||||||:|||||||:||: . .::.:.|:|||||||:|||||||||:|
253 VCFAPYHLVLVKAAAFSYYRGDRNAMCGLEERLYTASVVFLCLSTVNGV  302 HUMAN

301 ADPIIYVLGTDHSRQEVSRIHTGWKKWSTKTYV...TCSKDSEETHLPTE  347 MOUSE
    ||||||||.||||||||||||:||:|| ..||::.|:.
303 ADPIIYVLATDHSRQEVSRIHKGWKEWSMKTDVTRLTHSRDTEELQSPVA  352 HUMAN

348 LSNTYTFPNPAHPPGSQPAKLGLLCSPERLPEELC  382 MOUSE
    |.:  |||.|.|||||
353           CPAKRLIEESC  380 HUMAN
```

FIG. 2

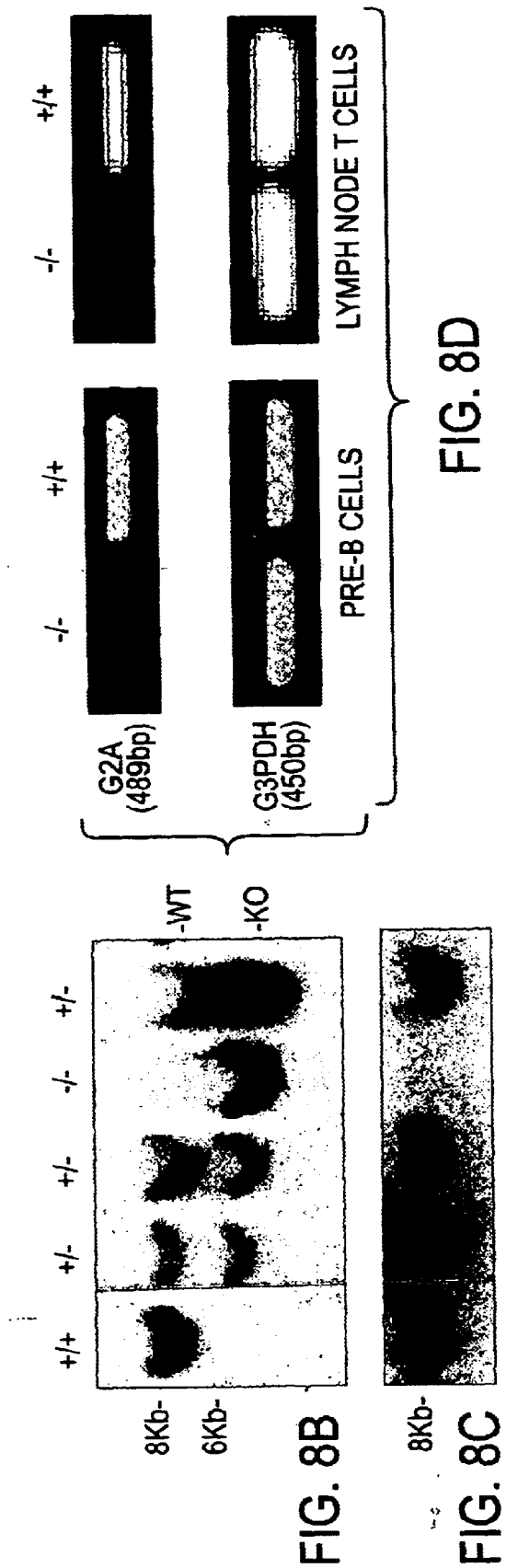

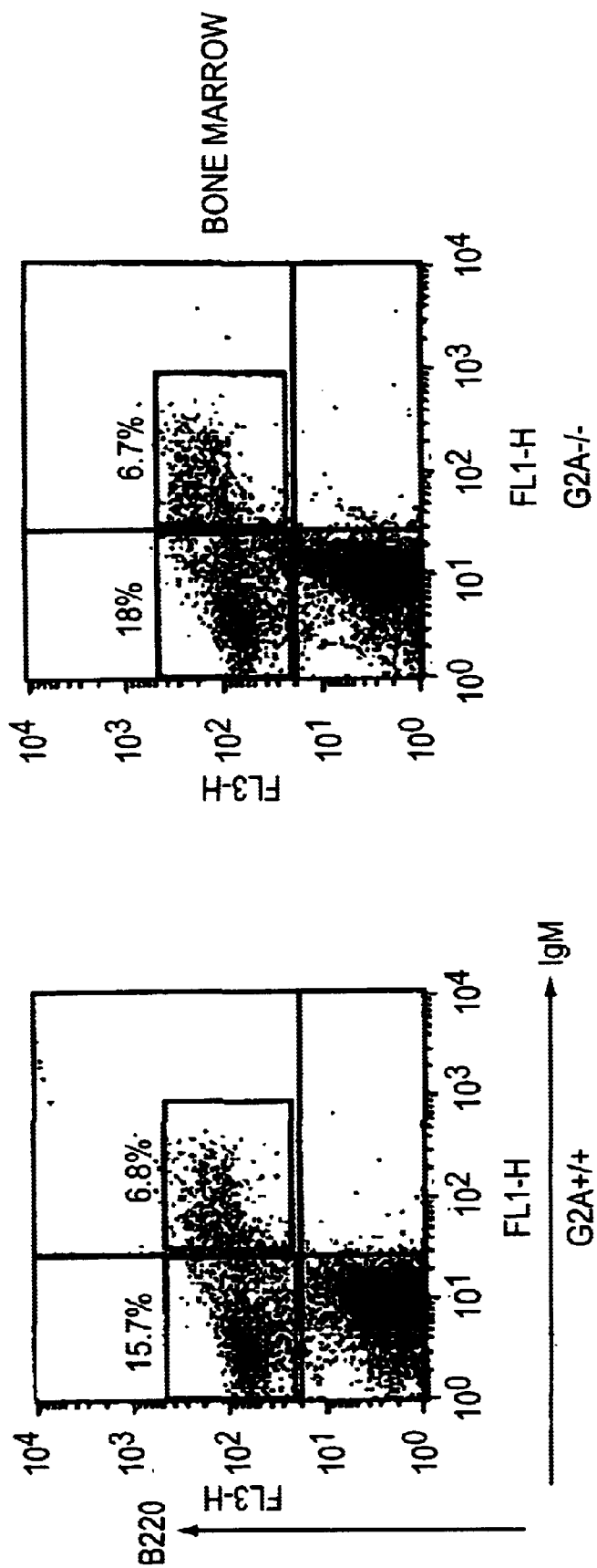

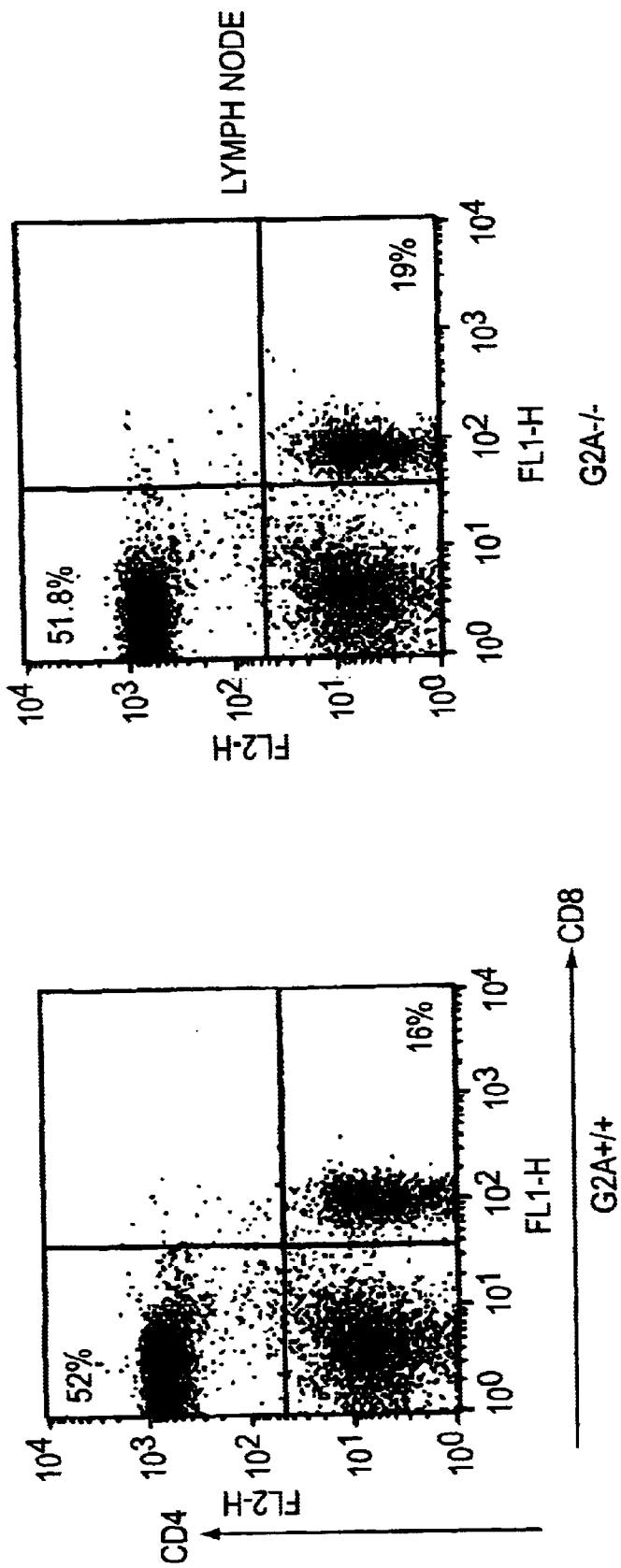

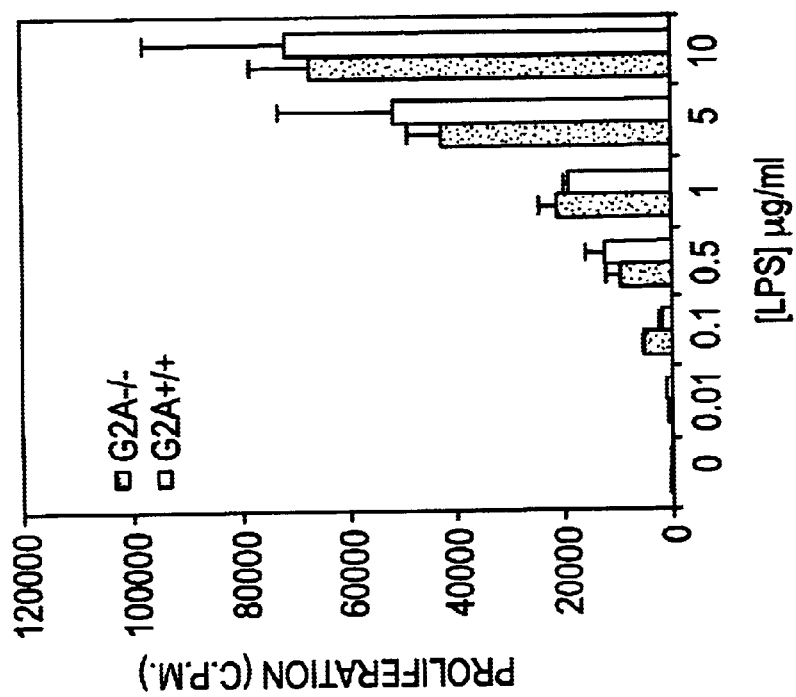
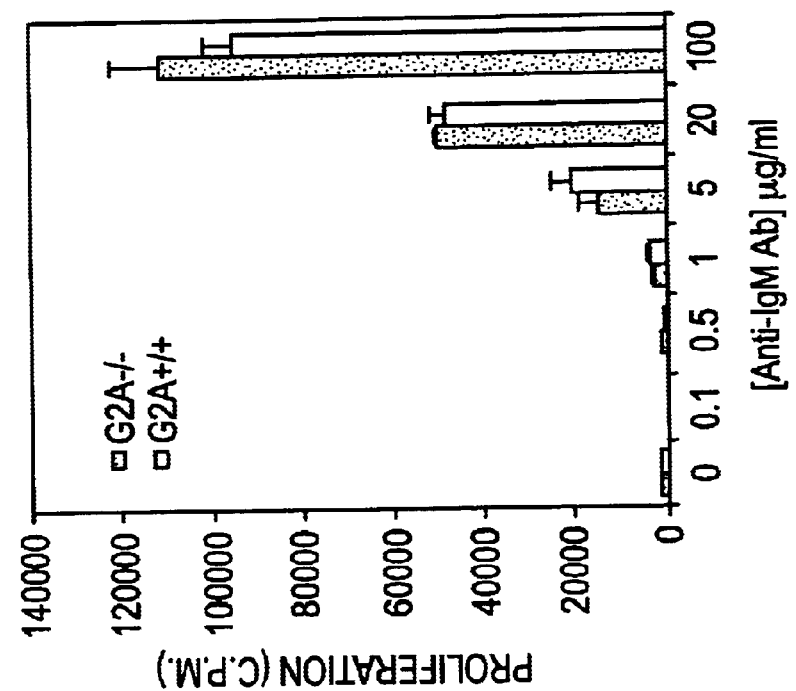

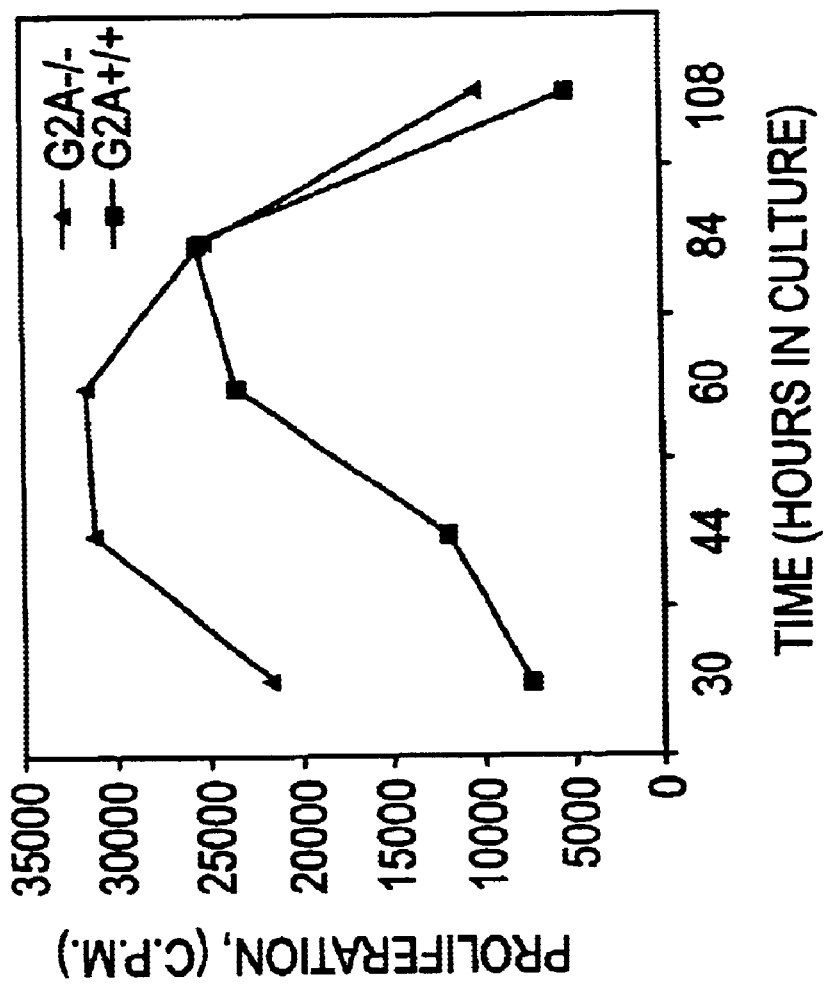

US 6,709,830 B2

METHODS FOR MODULATING THE ACTIVATION OF A LYMPHOCYTE EXPRESSED G PROTEIN COUPLED RECEPTOR INVOLVED IN CELL PROLIFERATION, AUTOIMMUNITY AND INFLAMMATION

RELATED APPLICATIONS

This present application is a continuation-in-part of U.S. patent application Ser. No. 09/553,875 filed Apr. 20, 2000, U.S. Pat. No. 6,514,696, which is a continuation-in-part of U.S. patent application Ser. No. 09/120,025 filed Jul. 17, 1998, U.S. Pat. No. 6,214,562, which is a continuation-in-part of U.S. patent application Ser. No. 08/969,815, filed on Nov. 13, 1997, U.S. Pat. No. 6,207,412.

STATEMENT REGARDING FEDERALLY SPONSORED RESEARCH OR DEVELOPMENT

This invention was made with Government support under Grant No. CA53867. awarded by the National Institutes of Health. The Government has certain rights in this invention

FIELD OF THE INVENTION

The present invention relates to methods for modulating the signalling of a G protein-coupled receptor which is expressed predominantly in lymphoid cells, and influences diverse physiological processes including cell proliferation, autoimmunity and inflammation.

BACKGROUND OF THE INVENTION

Bioactive lysophosphohipids regulate a wide variety of cellular activities including proliferation, smooth muscle contraction, wound healing, tumour cell invasiveness and inflammation. Formation of lysophospholipids is enhanced during oxidation of low density lipoprotein (LDL) and under inflammatory conditions. Most notably, lysophosphatidylcholine (LPC) plays a major aetiological role in atherescle-rosis (Lusis, AJ, Nature, 407: pp233–241, 2000), and is also implicated in the pathogenesis of the autoimmune disease Systemic Lupus Erythematosus (SLE) (Wu, R, et al, Lupus, 8: pp142–150, 1999) (Wu, R, et al, Clin Exp Immunol, 115: pp561–566, 1999). Both these diseases can be regarded as chronic inflammatory conditions and oxidatively modified phospholipids are increasingly recognised as autoantigens instrumental in their initiation and progression (Romero, FI, et al, Lupus, 9: pp 206–209, 2000) (Iuliano, L, et al, Blood, 90: pp3931–3935, 1997) (Koh, JS, et al, J Immunol, 165: pp4190–4201, 2000).

LPC is produced by the action of phospholipase $A_2$ ($PLA_2$) on phosphatidylcholine and promotes inflammatory effects including upregulation of endothelial cell adhesion molecules and growth factors (Kume, N, et al, J Clin Invest, 90: pp1138–1144, 1992) (Kume, N, et al, J Clin Invest, 93: pp907–911, 1994), chemotaxis of monocytes (Quinn, MT, et al, PNAS, 84: pp2995–2998, 1994), and stimulation of macrophage activation (Yamamoto, N, et al, J Immunol, 147: pp273–280, 1991). Although its mechanisms of action are poorly understood, LPC exerts both stimulatory and inhibitory effects upon several intracellular signalling molecules in certain contexts, supporting a role for LPC as an intracellular second messenger (Prokazova, NV, et al, Biochemistry (Moscow), 63: pp31–37, 1998) (Nishizuka, T, Science, 258: pp607–614, 1992) (Flavahan, NA, Am J Physiol, 264: ppH722–H727, 1993) (Okajima, F, et al, Biochem J, 336: pp491–500, 1998).

Unlike other lysophospholipids, it was thought that LPC actions were not mediated through specific cellular receptors such as membrane-bound GPCRs, a view that arose from the cell lytic properties of extracellular LPC and its abundance in cell membranes and body fluids (Lee, MJ, et al, Science, 279: pp1552–1555, 1998) (Okajima, F, et al, Biochemical Journal, 336: pp491–500, 1998) (Okita, M, et al, Int J Cancer, 71: pp31–34, 1997). Although studies demonstrating G protein-dependent cellular responses to LPC support the notion that this lysophospholipid also elicits biological effects via one or mote of the 250 plus members within the family of G protein-coupled receptors (Yuan, Y, et al, J Biol Chem, 271: pp27090–27098, 1996) (Okajima, F, et al, Biochemical Journal, 336: pp491–500, 1998), no specific high affinity LPC receptor has yet been identified.

Interest in both LPC and the GPCR family of receptors continues to increase due to data which suggests that they may targets for new diagnostic and therapeutic modalities. For example, from the perspective of their clinical significance, there is considerable focus on GPCRs expressed in the hematopoietic and lymphoid systems as many have been shown to play pivotal roles in the regulation of hematopoiesis and immune function. Receptor/ligand relationships within the GPCR family exhibit significant promiscuity, with many receptors recognizing more than one ligand and vice versa. This is especially true among chemokine receptors. Therefore, a major goal in the art is to identify receptor/ligand interactions within this family of GPCRs, particularly among lymphoid expressed orphan receptors of unknown function.

Consequently, there is a need in the art for the identification of both the receptors for LPC and related molecules as well as the ligands for orphan G protein-coupled receptors. The invention provided herein satisfies this need.

SUMMARY OF THE INVENTION

The invention provided herein describes ligands and methods for modulating a novel G protein-coupled receptor (GPCR), called G2A, a lymphocyte expressed orphan G protein-coupled receptor whose genetic ablation results in the development of autoimmunity. For example, the present disclosure teaches that lysophosphatidylcholine (LPC) is a high affinity ligand for G2A and that sphingosylphosphorylcholine (SPC) is a lower affinity ligand for G2A. In G2A-transfected cells, LPC binds to G2A with high affinity (Kd=65 nM) and specificity, and transiently increases intracellular calcium concentration. In addition, the specific binding of LPC to G2A also induces ERK MAP kinase activation and causes G2A receptor internalisation.

The invention described herein has a number of embodiments. A typical embodiment is a method of modulating G2A receptor mediated signaling in a cell comprising altering the concentration of G2A ligand present in the cell's environment that is capable of binding to and activating the G2A receptor. A specific embodiment consists of a method of modulating LPC mediated activation of a G2A receptor in a cell comprising altering the concentration of LPC capable of binding to and activating the G2A receptor. Yet another embodiment consists of a method of modulating SPC mediated activation of a G2A receptor in a cell comprising altering the concentration of SPC capable of binding to and activating the G2A receptor Methods that modulate G2A activation can be assessed by a variety of protocols.

In one embodiment, G2A receptor mediated signaling is measured by observing a transient elevation in the concentration of intracellular calcium ($[Ca^{2+}]$). In another embodiment, G2A receptor mediated signaling is measured by observing an induction of ERK MAP kinase activation. In a related embodiment, ligand binding to the G2A receptor is measured by a radioligand binding assay.

The concentration of G2A ligand present in the cell's environment that is capable of binding to and activating the G2A receptor can be altered in a variety of ways. Typically, the concentration of G2A ligand present in the cell's environment that is capable of binding to and activating the G2A receptor is increased by introducing exogenous LPC or SPC into the cell's environment. Alternatively, the concentration of G2A ligand present in the cell's environment that is capable of binding to and activating the G2A receptor is decreased, for example by antibody inhibition of the ligand-receptor interaction or by the LPC antagonist choline. Alternatively, other competitive molecules can be employed in such methods. For example, the concentration of SPC capable of binding to and activating the G2A receptor can be decreased by introducing exogenous LPC into the cell's environment. Alternatively, the concentration of LPC capable of binding to and activating the G2A receptor can be decreased by introducing exogenous SPC into the cell's environment.

BRIEF DESCRIPTION OF THE DRAWINGS

FIGS. 8A–D show the targeting vector for homologous recombination into the G2A locus. (A) genomic organisation of the wild-type G2A allele, structure of the G2A targeting vector and predicted structure of the correctly targeted mutant allele. (B and C) Southern Blot analysis of Pst1 digested tail genomic DNA hybridized with the external probe B (B) for genotypic determination, or the internal probe A (C) to determine successful deletion of the G2A gene. (D) RT-PCR analysis of total RNA derived from splenic T cells (right panels) and BCR-ABL transformed Pre-B cells (left panels) using G2A-specific primers P1 and P2.

FIGS. 9A–H show normal T and B lymphoid development in G2A-/- mice. Flow cytometric analysis of thymic, splenic, lymph node and bone marrow cells from 8 week old wild-type mice (left panels) and 8 week old G2A-/- mice (right panels). Proportions of cells in each quadrant are indicated as percentages.

FIGS. 13A–F show that G2A−/− T cells but not B cells exhibit hyperproliferative responses to antigen receptors cross-linking stimulation in vitro. Proliferation of peripheral T cells from young wild-type and G2A−/− mice stimulated by various concentrations of anti-CD3ε antibody alone (A), or with CD28 costimulation (B). Proliferation was assessed in triplicate by [$^3$H] Thymidine incorporation during the last 12 hours of culture. FACS analysis of propidium iodide stained G2A−/− (C) and wild-type (D) T cells 36 hours following anti-CD3ε stimulation. Equal proliferative responses of splenic B cells from wild-type and G2A−/− mice by anti-IgM cross-linking (E) or LPS (F).

FIGS. 14A–C show self-reactive, hyperresponsive and altered threshold of TCR-dependent activation in G2A−/− T cells. Syngeneic (A) and allogenic (B) mixed lymphocyte reactions using lymph node T cells as responder cells and autologous splenic B cells or B6 derived B cells as stimulators. (C) Kinetics of stimulation of wild-type and G2A−/− T cells by 5 μg/ml anti-CD3L antibody. T cell proliferation was assessed in triplicate by measurement of [3H] Thymidine incorporation during a 12-hour period ending at the indicated time points following stimulation.

DETAILED DESCRIPTION OF THE INVENTION

Figure 1:
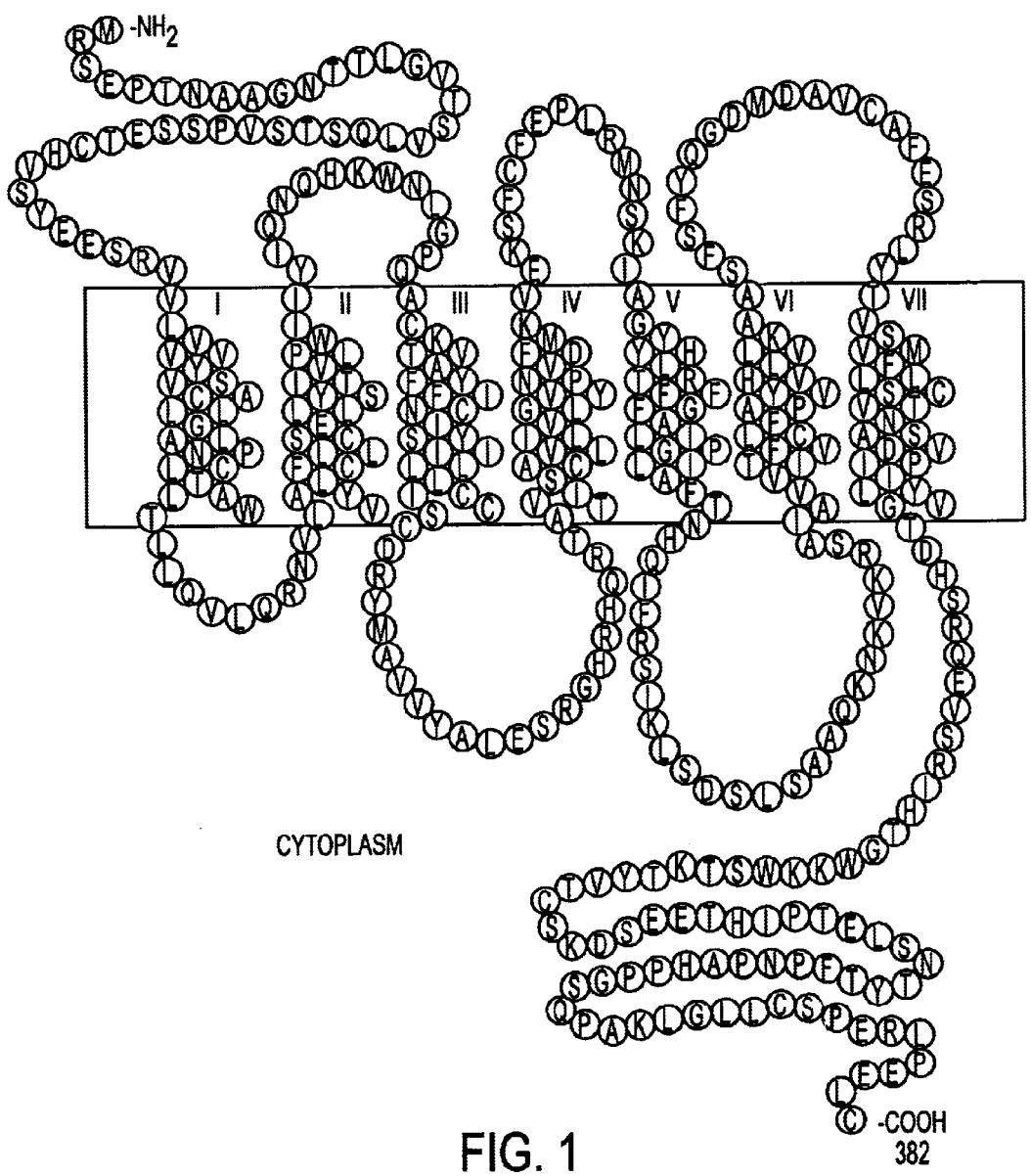
FIG. 1 is a schematic diagram of murine G2A (SEQ ID NO:2) showing the seven predicted transmembrane domains.
Figure 3:
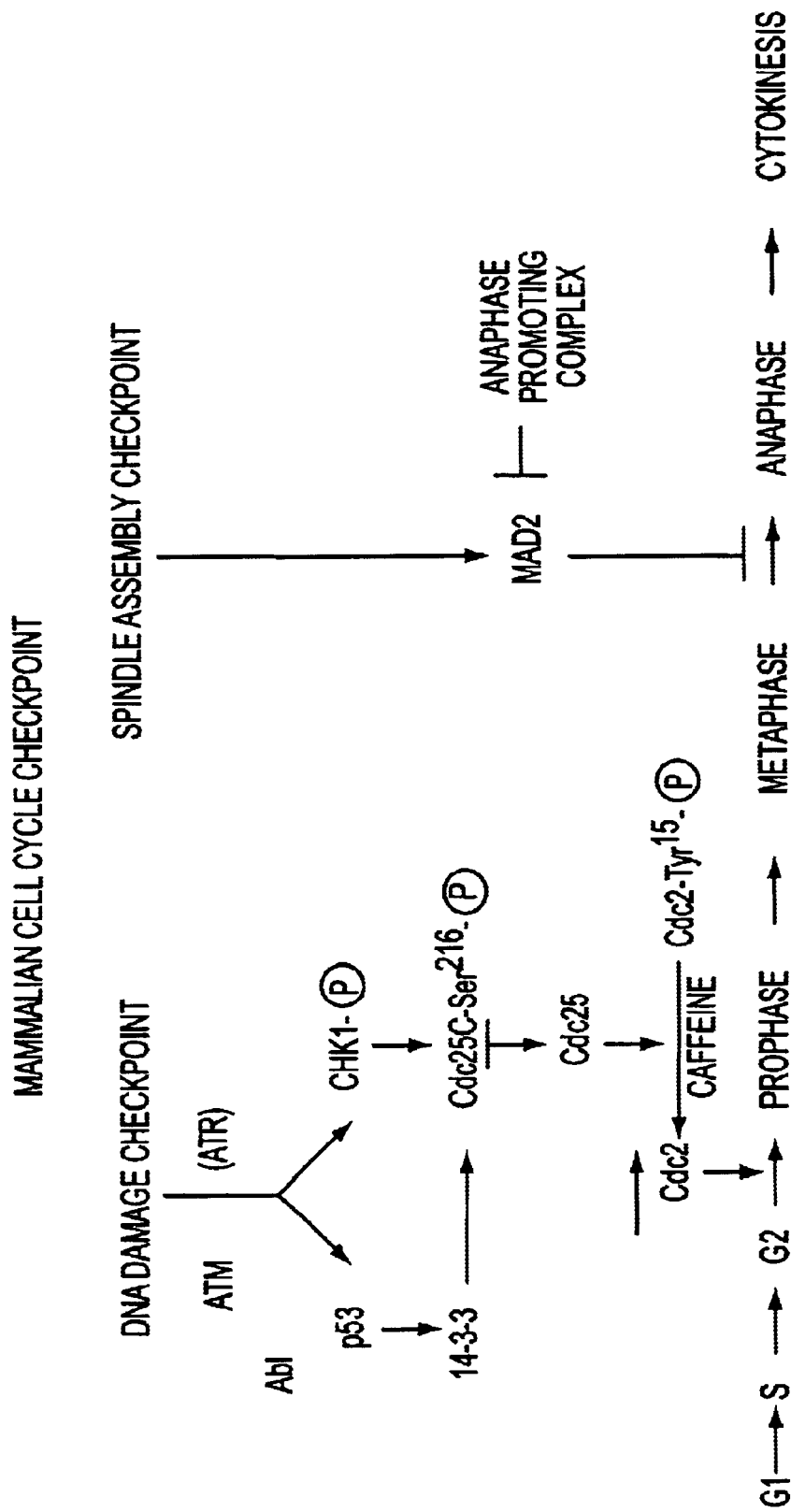
FIG. 3 is a schematic diagram showing the mammalian cell cycle checkpoint.

Despite its recognition as an important aetiological factor in human systemic autoimmune disease and atherosclerosis, biological actions of lysophosphatidylcholine (LPC) have been established primarily as an intracellular second messenger and no cognate receptor has been identified. Here we show that lysophosphatidylcholine is a high affinity ligand (and sphingosylphosphorylcholine (SPC) is a lower affinity ligand) for a novel G protein-coupled receptor (GPCR), called G2A, a lymphocyte expressed orphan G protein-coupled receptor whose genetic ablation results in the development of autoimmunity. In G2A-transfected cells, LPC binds to G2A with high affinity (1 Kd=65 nM) and specificity, and transiently increases intracellular calcium concentration. The specific binding of LPC to G2A also induces ERK MAP kinase activation and causes receptor internalisation.

Designated G2A for G2 arrest, this G protein-coupled receptor is transcriptionally regulated by a variety of intracellular and extracellular stimuli including tyrosine kinases, DNA damaging agents and chemotherapeutic drugs. G2A appears to serve as a tissue specific sensor of DNA damage and cellular proliferation, and functions at the G2/M checkpoint to delay mitosis following DNA damage, or to prevent deregulated growth incurred by excessive growth stimuli. Therefore, G2A may couple proliferative signaling and cell cycle checkpoint pathways to ensure faithful and properly controlled duplication of hematopoietic cells.

In addition, transcriptional induction and expression of G2A integrates diverse signals by modulation of cytoskeletal architecture. Employing microinjection of constructs encoding G2A into Swiss 3T3 fibroblasts and embryonic fibroblasts derived from various Gα knockout mice, a signaling pathway was delineated downstream of G2A leading to actin reorganization into stress fibers via Gα13 and RhoA. Microinjection of constitutively active mutants of RhoA into Swiss 3T3 fibroblasts induces the formation of actin stress fibers and focal adhesions (Ridley et al., Cell 70:389–399, 1992). In addition, RhoA functions as a downstream component of signaling pathways initiated by ligand stimulation of the G protein-coupled LPA receptor leading to stress fiber assembly (Barry et al., J. Cell Sci. 107:2033–2045, 1994). Direct activation of RhoA by G2A was observed in Swiss 3T3 fibroblasts. In addition, RhoA dependent transcriptional activation of Serum Response Factor (SRF) induced by transient expression of G2A required both Gα13 and Gα12. Thus, G2A expression and transcriptional induction may play a role in the integration of proliferative and/or differentiative signals with cytoskeletal reorganization.

G2A also functions as a tumor suppressor gene, induces cell cycle arrest during mitosis and is found on human chromosome 14q32.3, a region frequently found altered in human cancers. G2A was identified while studying cellular genes that can be regulated by BCR-ABL. Using representational difference analysis RDA), a PCR-based differential screening technique (Lisitsyn et al., Science 259:946–951, 1993; Hubank et al., Nucl. Acids Res. 22:5640–5648, 1994), genes expressed in murine bone marrow (pre-B) cells transformed by the wild type (WT) BCR-ABL were compared to those expressed when a transformation-defective mutant variant carrying a mutation in the SH2 domain of BCR-ABL was used to infect these cells. More than a dozen genes were found to be upregulated by BCR-ABL. One of these differentially expressed murine genes (G2A) was predominantly expressed primarily in hematopoietic and lymphoid tissues such as spleen, thymus and lymph nodes as determined by semi-quantitative PCR, and was induced by WT BCR-ABL, but not the SH2 mutant.

The cDNA and deduced amino acid sequences of the murine G2A are shown in SEQ ID NO: 1 and SEQ ID NO: 2, respectively. The human homologue of the mouse protein was then isolated using the murine cDNA as a probe. The corresponding human cDNA and deduced amino acid sequences are shown in SEQ ID NO: 3 and SEQ ID NO: 4, respectively. The G2A protein sequence of the invention has the sequence shown in SEQ ID NOS; 2 and 4, or sequence variations thereof which do not substantially compromise the ability of these genes to be regulated by protein tyrosine kinases or sequence variations thereof which do not substantially compromise the functional activities of these proteins. From the assays of G2A signalling that are provided herein, it will be appreciated that the modulation of functional G2A proteins containing one or more amino acid replacements or modifications in various positions of the sequences shown in SEQ ID NOS: 2 and 4 are also within the scope of the invention.

The murine protein was determined to be a member of the GPCR superfamily by its homology to other GPCRs, including the mouse TDAG8 protein and the P2Y receptor, using sequence alignment programs. A schematic diagram of murine G2A showing the seven predicted transmembrane domains is shown in FIG. 1. The human G2A homologue was isolated by screening a human spleen cDNA library under high stringency conditions (2× SSC, 0.1% SDS, 65° C.). The murine and human G2As share approximately 70% identity at the amino acid level (FIG. 2) and have a calculated molecular weight of about 42 kDa. These proteins share the highest degree of identity (76%) in the seven transmembrane domains as well as the extracellular and intracellular loops, whereas they are more divergent in the N-terminal extracellular domain (25% identity) and C-terminal cytoplasmic tail (55% identity). Both murine and human G2A contain putative N-linked glycosylation sites in the N-terminal extracellular domain characteristic of GPCRs.

The G2A is expressed in spleen, thymus, and pro-B cells in bone marrow, suggesting that it may play an important role in mid- and late stages of T and B cell development. During development, self-reactive immature thymocytes are clonally deleted in the thymus, a phenomenon which establishes T cell tolerance (negative selection). It has been shown that the deletion of self-reactive immature T cells in the thymus is mediated by apoptosis upon T cell receptor engagement. TDAG8, a GPCR family member, is induced in T cells during apoptosis upon T cell receptor activation (Choi et al., Cell. Immunol, 168:78–84, 1996). This suggests that TDAG8 may play a role in negative selection of T cells. Since the G2As that we isolated share about 30% homology with TDAG8, it is conceivable that the G2As may also play a role in negative selection of T cells. Sequence analysis of the G2A with its family members reveal that they also share significant homology with the P2Y receptor, a GPCR for ATP. It has been shown recently that P2Y receptor is transcriptionally upregulated during T cell activation (Koshiba et al., Proc. Natl. Acad. Sd. U.S.A., 94:831–836, 1997).

G2A may play a role in directing migration of lymphocytes into specific anatomical compartments of spleen and thymus for maturation. Previous studies on a hematopoietic-specific GPCR, BLR1, suggest that BLR1 plays an important role for directing migration of lymphocytes into splenic follicles as well as migration of activated B cells into B cell-folicles of the spleen, a prerequisite for the development of an antigen-specific immune response (Forster et al., Cell, 87:1037–1047, 1996). Expression of G2As in hematopoietic-specific tissues suggest that it may also play similar roles in directing migration of lymphocytes into lymphoid organs for their maturation.

Both the mouse and human G2A cDNA clones can be used for in situ analysis to examine whether the expression of the receptor is restricted to certain anatomical regions of the spleen and thymus. The mouse and human genomic clones encoding the full length G2As were also isolated. The mouse genomic clone has been used for constructing a targeting vector to knock-out the G2A in mice by homologous recombination. The G2A –/–mice will allow further evaluation of the physiological functions of this receptor. The G2A –/–mice will also allow determination of whether in vivo leukemogenesis is dependent on the GZA. The mouse and human genomic clones may contain the distal and proximal promoters of the G2As that will allow the analysis of the transcriptional regulation of hematopoietic-specific genes. Both the mouse and human genomic clones can also be used for cytogenetic mapping to examine whether the G2As are linked to any known genetic diseases.

As discussed herein, it is well known in the art that molecules such as antibodies are used to modulate the activation of a wide variety of cellular receptors including GPCRs (see, e.g., Fu et al.; Receptors Channels 1994;2(2):121–30; Zijlstra-Westhoff et al., J Reprod Immunol 1998 July; 38(2):139–54; Petrucci et al., Br J Pharmacol 2000 February; 129(3):471–84). Rabbit antiserum to G2A was prepared which was reactive with either the N-terminal portion or the C-terminal portion of the receptor as confirmed by ELISA. Briefly, two rabbits were injected with a 13 amino-acid peptide corresponding to the cytoplasmic tail of the receptor. Another two rabbits were injected with GST-G2A-N, a glutathione-S-transferase fusion protein containing the N-terminal extracellular domain of the G2A. The sera from the second, third, and fourth production bleed of both rabbits exhibited strong immune response to the peptide as seen in the ELISA assay. The antibodies were affinity purified using a peptide affinity column and are valuable for analyzing the expression of this G2A in T and B cell development. These antibodies were used to assist in determining the structure and localization of the G2A protein. Antibody results suggest that the N-terminal portion is the extracellular domain and the C-terminal portion is the intracellular domain which is consistent with known GPCRs.

Monoclonal antibodies to the receptor can also be generated using conventional hybridoma technology known to one or ordinary skill in the art. Briefly, three mice are immunized with 25 μg recombinant receptor prepared as described in Example 9. Mice are inoculated at 3 week intervals with 20 μg G2A per mouse (½ subcutaneously and ½ intraperitoneally). Serum collected from each animal after the first inoculation reacts with G2A as determined by immunoprecipitation. Three days after the final inoculation, mice are sacrificed and the spleens harvested and prepared for cell fusion. Splenocytes are fused with Sp2/0 AG14 myeloma cells (ATCC CRL 1581) with polyethylene glycol (PEG). Following PEG fusion, cell preparations are distributed in 96-well plates at a density of $10^5$ cells per well and selected in hypoxanthine/aminopterin/thymidine (HAT) medium containing 10% fetal calf serum and 100 U/ml interleukin-6. The medium is replaced with fresh HAT medium 10 days after plating. To identify hybridomas producing MAbs which recognize G2A, hybridoma supernatants are tested for the ability to immunoprecipitate purified recombinant G2A or to detect G2A by immunoblotting.

A glutathione-S-transferase (GST) fusion protein of the N-terminal extracellular domain of the G2A was constructed. The mouse and human G2As were cloned into various eukaryotic expression vectors which will allow the overexpression of recombinant mouse and human G2As in transfected cells in vitro and in vivo by methods well known to one of ordinary skill in the art. Preferably, the constructs containing the G2A is transfected into eukaryotic cells; more preferably into mammalian cells. Alternatively, the construct may be used to transform bacterial cells.

Growth arrest induced by G2A indicates its potential for therapeutic intervention in cases of deregulated proliferation of lymphoid cells. G2A resists cellular proliferation, thus its agonists are useful in delaying the progression of diseases including leukemias, lymphomas and autoimmune diseases. Since G2A is upregulated by BCR-ABL and can suppress the outgrowth of lymphocytes and fibroblasts (Tables 1A–B), antibodies, drugs or natural ligands can be screened in vitro which can activate G2A. Drugs, antibodies or natural ligands which inhibit the growth of lymphocytes are useful for treatment of the diseases mentioned above.

Conversely, monoclonal antibodies can be generated against particular regions of G2As which block the G2As and stimulate the growth of normal lymphocytes in vivo. In addition, in vitro screening assays can be used to find drugs or natural ligands which bind to and either activate or inactivate the G2A. These antibodies, drugs or natural ligands can stimulate the growth of lymphocytes, which may in turn cure or alleviate the symptoms of patients who have either inherited immunodeficiency diseases or Acquired immune deficiency syndrome (AIDS). For example, patients with severe combined immune deficiency (SCID), DiGeorge syndrome, or Bare lymphocyte syndrome lack T cells, and patients with X-linked agammaglobulinemia lack B cells.

The antibodies, drugs, natural ligands can be delivered into these patients to inhibit the G2A to stimulate the growth of the T and B cells in their immune system.

Recently, the orphan GPCR OGR-1 was identified as a high affinity receptor for sphingosylphosphorylcholine (SPC), a lysophospholipid structurally similar to LPC (Yan Xu, et al, Nature Cell Biology, 2: pp261–267, 2000). Based upon protein sequence homology, OGR-1 is closely related to G2A (Weng, Z., et al, PNAS, 95:12334–12339, 1998), TDAG8 (Choi, J. W. et al, Cell Immunol, 168:78–84, 1996), and GPR4 (Reiber, M., et al, DNA & Cell Biology, 14:25–35, 1995). These GPCRs may therefore constitute a sub-family with overlapping functions and specificities towards related ligands. Amongst these receptors, G2A is expressed predominantly in T lymphocytes and its genetic ablation in mice results in the development of an autoimmune syndrome similar to SLE (Weng, Z., et al, PNAS, 95:12334–12339, 1998). As disclosed herein we examine ligand properties of various lysophospholipids towards G2A by measurement of intracellular calcium release, ERK MAP kinase activation, receptor internalisation and direct binding assays in G2A expressing cells.

G2A may be a hitherto unrecognised aetiological factor in atherosclerosis. Despite their recruitment to atherosclerotic lesions and chemotactic responses to LPC (Lusis, A J, Nature, 407: pp233–241, 2000) (McMurray, H, et al, J Clin Invest, 92: pp1004–1008, 1993), early studies suggested that T cells may not play major roles in atherogenesis (Fyfe, A I, et al, J Clin Invest, 94: pp2516–2528, 1994). However, more recent studies have revealed the importance of CD40/CD40 ligand interactions (Sakata-IJaneko, S, et al, FEBS Letters, 433: pp161–165, 1998) (Schonbeck, V, et al, PNAS, 97: pp7458–7463, 2000), T cell production of interferon Tγ (Gupta, S, et al, J Clin Invest, 99: pp2752–2761, 1997), and antibodies to oxLDL epitopes, most notably LPC (Shaw, PY, et al, J Clin Invest, 105: pp1731–1740, 2000).

Increased levels of antibodies against LPC are also a feature of SLE (Wu, R, et al, Lupus, 8: pp142–150, 1999) (Wu, R, et al, Clin Exp Immunol, 115: pp561–566, 1999) (George, J, et al, Lupus, 8: pp220–226, 1999). How the pathology of this disease could relate to this receptor/ligand pair, if at all, is perplexing and likely to be complex considering the multiple susceptibility factors involved in SLE (Sullivan, K E, Rheumatic Diseases Clinics of North America, 26: No. 2, 2000). Further complexity is introduced by the broad cellular involvement in SLE and the presence of related lysophospholipid receptors. Nevertheless, several possibilities can be proposed. For example, it is possible that G2A plays a role as a sensor of LPC levels produced at sites of inflammation and limits expansion of tissue infiltrating cells and progression to overt autoimmune disease. Differential effects of exogenously applied LPC in T cells have been reported, including potentiation of proliferative responses induced by diacylglycerol activation of PKC (Asaoka, Y, et al, PNAS, 89: pp6447–6451, 1992). While these effects are elicited by high concentrations of LPC and involve its action as a second messenger, several studies suggest that endogenously produced LPC may influence T cell responses and that receptor mediated signals are involved. For example, PLA$_2$ mediated LPC production is stimulated in T cells following T cell receptor (TCR) crosslinking in vitro (Asaoka, Y, et al, PNAS, 89: pp6447–6451, 1992) and may modulate long-term responses of activated T lymphocytes. Consistent with this hypothesis, T cells from G2A-deficient mice exhibit hyperproliferative responses to TCR stimulation in vitro.

Increased phospholipid oxidation is also a feature of apoptotic cells, which express oxLDL specific ligands on their surfaces and are increasingly recognised as targets of autoantibodies in SLE (Buttke, T M & Sandstrom, P A, Immunol Today, 15: pp7–10, 1994) (Dixit, V M, et al, Science, 281: pp1305–1326, 1998) (Price, B E, et al, J Immunol, 157: pp2201, 1996). Indeed, an impairment in apoptotic clearance may be a pathophysiological factor and such a defect can be induced by antibodies against LPC (Koh, J S, & Levine, J S, Curr Opin Nephrol Hypertens, 6: pp259, 1997) (Chang, M K, et al, PNAS, 96: pp6353–6358, 1999). G2A is also expressed in macrophages, providing evidence that G2A may play a role in the recognition of apoptotic antigens.

Attempts to determine whether G2A-deficient cells exhibit altered responsiveness to exogenously applied LPC in vitro may be hampered by the high physiological concentrations of this lysophospholipid in serum (Okajima, F, et al, Biochemical Journal, 336: pp491–500, 1998) (Okita, M, et al, Int J Cancer, 71: pp31–34, 1997). In addition, homologous GPCRs may compensate for loss of G2A function (Choi, J W, et al, Cellular Immunol, 168: pp78–84, 1996) (Heiber, M, et al, DNA & Cell Biology, 14: pp25–35, 1995). Furthermore, LPC can exist in several physiological forms, including free, micellar, LDL, bound to hydrophobic serum proteins such as albumin, consumed within immune complexes, and incorporated into plasma membranes. While our studies show that application of LPC elicits short-term responses, we cannot exclude the possibility that long-term exposure of cells to exogenously applied LPC results in its conversion to a form with altered receptor binding properties.

The identification of LPC as a ligand for G2A provides a novel perspective on the role of this lysophospholipid as an extracellular mediator of inflammatory autoimmune disease and atherosclerosis. The suitability of GPCRs as targets of drug based therapeutic intervention promises that further studies may uncover clinical benefits of modulating G2A activity in the treatment of these diseases.

A. Typical Methods for Modulating the G2A-ligand Interaction

The invention disclosed herein provides a number of methods for modulating the interaction between G2A and G2A ligands such as LPC and SPC. A typical embodiment consists of a method of modulating G2A receptor mediated signaling in a cell comprising altering the concentration of G2A ligand present in the cell's environment that is capable of binding to and activating the G2A receptor. In a preferred embodiment, the concentration of G2A ligand present in the cell's environment that is capable of binding to and activating the G2A receptor is altered by the introduction of an exogenous ligand. In introducing a ligand into the cell's environment, it is meant that the ligand is placed into the cell's mllieu so that it can effect a physiological process of that cell either directly or indirectly. A variety of methods for introducing therapeutic molecules such as polypeptides, small molecules or other ligands into a cell's environment ate well known in the art, with typical methods including intravenous or site specific injection. Another related embodiment of the invention is a method of controlling or influencing the intracellular calcium release that is associated with G2A activation, typically by modulating the concentration of G2A ligand that is present in the cell's environment and capable of binding to and activating G2A.

The term concentration as used, for example in "altering the concentration of G2A ligand" refers to its art accepted meaning of the relative content of a component (e.g. a ligand such as LPC) in a particular milieu (e.g. in vivo or in vitro).

The concentration of G2A ligand capable of binding to and activating a receptor can be altered by a number means. Typically, an amount of exogenous G2A ligand is added to the particular milieu by means known in the art in order to alter a concentration in that context (e.g. intravenous or site specific injection).

In addition as it is well known in the art that because ligands can exist in several physiological forms (e.g. free or bound to another molecule such as a protein), one can alter the concentration of ligand capable of binding to and activating a receptor by controlling or influencing the amount of ligand in the form that is capable of effecting activation. Similarly, one can alter the concentration of ligand capable of binding to and activating a receptor by employing a molecule that inhibits a ligand's ability to activate the receptor. Typically, an antibody is used to inhibit the ability of a ligand to activate a receptor, for example by binding to the ligand and/or the receptor and acting as a stearic hindrance in the ligand-receptor interaction. In addition, one can alter the concentration of ligand capable of binding to and activating a receptor by employing a molecule that competitively inhibits the ligand's ability to activate the receptor. In this way such molecules alter the concentration, for example, of G2A ligand present in the cell's environment that is capable of binding to and activating G2A by competing with the ligand, thereby preventing a ligand that would otherwise active G2A, from doing so.

There are a variety of art accepted methods for measuring the G2A-ligand interaction, a number of which are described herein. In a typical preferred embodiment, G2A mediated signaling is measured by observing a transient elevation in the concentration of intracellular calcium ($[Ca^{2+}]$) (see e.g. Example 9). Alternatively, one can measure the G2A receptor mediated signaling by observing an induction of ERIE MAP kinase activation (see e.g. Example 11). In another preferred embodiment, the G2A-ligand interaction is measured by a radioligand binding assay (see e.g. Example 13).

In preferred methods of the invention, the concentration of G2A ligand present in the cell's environment that is capable of binding to and activating the G2A receptor is increased. Typically, the concentration of G2A ligand present in the cell's environment that is capable of binding to and activating the G2A receptor is increased by introducing exogenous lysophosphatidylcholine into the cell's environment. Alternatively, the concentration of G2A ligand present in the cell's environment that is capable of binding to and activating the G2A receptor is increased by introducing exogenous sphingosylphosphorylcholine into the cell's environment. Typically, an amount of exogenous G2A ligand is added to the cell's environment by one of the well known means known in the art (e.g. intravenous or site specific injection).

In another preferred embodiment of invention, the concentration of G2A ligand present in the cell's environment that is capable of binding to and activating the G2A receptor is decreased. A variety of methods for decreasing the amount of G2A ligand present in the cell's environment are known in the art. For example in the context of in vitro systems, the concentration of G2A ligand present in the cell's environment that is capable of binding to and activating the G2A receptor can be decreased by dilution. In the context of in vivo systems, the concentration of G2A ligand present in the cell's environment that is capable of binding to and activating the G2A receptor can be decreased by the addition of an anti-ligand antibody, for example a anti-LPC antibody which inhibits the ligand-receptor interaction (see, e.g., Wu et al., Lupus 1999, 8(2): 142–150; Wu et al., Arterioscler. Thromb. Vasc. Biol. 1998, 18(4): 626–630). Alternatively, the concentration of G2A ligand present in the cell's environment that is capable of binding to and activating the G2A receptor can be decreased by the addition of an anti-G2A antibody which inhibits the ligand-receptor interaction. In a similar embodiment, the concentration of G2A ligand present in the cell's environment that is capable of binding to and activating the G2A receptor can be decreased by the addition of an soluble receptor construct which effective competes with G2A for ligand binding (see, e.g., Komesli et al., Eur J Biochem Jun. 15, 1998; 254(3):505–13; Remy et al., J Biol Chem Oct. 3, 2000; PMID: 11018026). In yet another embodiment, the concentration of G2A ligand present in the cell's environment that is capable of binding to and activating the G2A receptor can be decreased by the addition of an LPC antagonist such as choline (see, e.g., Gupta et al., 1997: Indian J. Chest. Dis. Allied Sci., 39(3): 149–156; Gupta et al., Indian J Chest Dis Allied Sci 1997 April–June; 39(2):107–13). In yet another embodiment, the concentration of G2A ligand present in the cell's environment that is capable of binding to and activating the G2A receptor may be decreased by the addition of an agent known to decrease that class of molecules (see, e.g., Guijarro et al., Kidney Int Suppl 1999 July; 71:S88–91). It is also known in the art that a number of different molecules such as pertussis toxin can modulate the activities of molecules such as SPC and LPC (see, e.g., Okajima et al., J. Biol. Chem. 1995 270(44): 26332–40; Anderson et al., Br. J. Pharmacol 1996 117(7): 1387–1394; Masamune et al., Pancreas 2001, 22(1): 75–83; Krajewska et al., J. Infect. Dis. 1993, 167(4): 899–904; Seufferlein et al., J. Biol. Chem. 1995, 270(41): 24334–42; Flavahan, N. A., Am. J. Physiol. 1993, 264(3 pt 2): H722–7).

LPC and SPC are high and low affinity (respectively) G2A ligands identified herein which are capable of binding to and activating the G2A receptor. The invention disclosed herein also provides a model for identifying and/or assessing other G2A ligands, by for example, providing a set of high and low affinity standard ligands which provide parameter means for identifying and assessing novel molecules. Typically this aspect of the invention provides a process for identifying and/or assessing the ability of a novel molecule to bind to G2A in a comparative assay that compares the novel molecule's measured activity with that of LPC and/or SPC. In this context, a number of analytical assays for analyzing ligand-receptor interactions are well known in the art and include for example the binding and activation assays discussed in the Examples below. Also included in this embodiment is a product identified and/or assessed by this process. A related method for identifying a compound which binds to G2A comprises the steps of contacting a G2A receptor with a test compound, determining whether said compound binds to said G2A; and if the compound binds to G2A, determining whether said compound activates the G2A receptor. Typically, the activation of G2A indicates that the compound is useful for modulating G2A activity. Also included in this embodiment is a product identified and/or assessed by such methods.

A highly preferred embodiment of the invention consists of a method of modulating G2A receptor mediated signaling in a cell comprising altering the concentration of lysophosphatidylcholine or sphingosylphosphorylcholine present in the cell's environment that is capable of binding to and activating the G2A receptor (i.e. the G2A ligand is selected from the group consisting of lysophosphatidylcholine and sphingosylphosphorylcholine). As noted above a number of methods for altering the concentration of lysophosphatidylcholine and sphingosylphosphorylcholine in this context are well known in the art. For example, one can alter the concentration of lysophosphatidylcholine or sphingosylphosphorylcholine capable of binding to and activating a receptor by employing a molecule that competitively inhibits lysophosphatidylcholine's or sphingosylphosphorylcholine's ability to activate the receptor. In this way such molecules alter the concentration, for example, of G2A ligand present in the cell's environment that is capable of binding to and activating G2A by competing with the ligand, thereby preventing a ligand that would otherwise active G2A, from doing so. An illustrative example of such a competition is the use of LPC to compete with SPC for G2A activation.

As discussed herein, LPC and SPC are high and low affinity ligands for G2A which can be evaluated in a number assays observing the binding to and/or activation of G2A. While LPC is typically discussed herein as a representative molecule analogous methods employing SPC are also contemplated. A typical embodiment consists of a method of modulating SPC mediated activation of a G2A receptor in a cell comprising altering the concentration of SPC capable of binding to and activating the G2A receptor. Typical methods for increasing the concentration of SPC capable of binding to and activating the G2A receptor include the introduction of exogenous SPC by means known in the art (e.g. intravenous or site specific injection). Alternatively, the concentration of SPC capable of binding to and activating the G2A receptor can be decreased, for example by introducing exogenous LPC into the cell's environment. In this context, LPC is a higher affinity ligand for G2A which can compete with the SPC for G2A activation, thereby preventing SPC that would otherwise active G2A, from doing so.

A number of typical specific methods that can be used to evaluate molecules that modulate G2A activation are known in the art. In one embodiment, the cDNA encoding the G2A is placed in a eukaryotic expression vector for transfection into or infection of a mammalian cell line in order to create a cell based assay for activity. Many such cell lines are known in the art, including NIH 3T3, Rat-1, 293T, COS-1, COS-7 and Chinese hamster ovary (CHO) cells, most of which are available from the American type Culture Collection (ATCC), Manassas, Va. Many such expression vectors are known and are commercially available. Preferred expression vectors include retrovital vectors, adenoviral vectors and SV40-based vectors. The vector may contain a selectable marker, such as antibiotic resistance, to select for cells which are expressing the receptor. Alternatively, the expression of the G2A can be under the control of a regulatory promoter. Stable transfectants ate used to screen large libraries of synthetic or natural compounds to identify compounds which bind to the G2A. Compounds which bind to the G2A are then tested in the assays such as those described in Examples 3, 5, 6, and 7 to determine whether they are agonists or antagonists of G2A activation as well as their ability to compete with and/or augment the activation of G2A that is triggered by LPC and SPC.

In one embodiment of the invention, a compound to be tested is radioactively, colorimetrically or fluorimetrically labeled using methods well known in the art and incubated with the receptor. After incubation, it is determined whether the test compound is bound to the receptor. If so, the compound is a potential agonist or antagonist. Functional assays are performed to determine whether the receptor activity is activated or inhibited. These assays include fibroblast and bone marrow transformation assays, cell cycle analysis and in vivo tumor formation assay. Alternatively, one can utilize assays such as those that measure the activation of ERK MAP kinase or the ligand induced internalization of G2A as shown in Examples 11 and 12 respectively. Responses can also be measured in cells expressing the receptor using signal transduction systems including, but not limited to, protein phosphorylation, adenylate cyclase activity, phosphoinositide hydrolysis, guanylate cyclase activity, ion fluxes (i.e. calcium) and pH changes. These types of responses can either be present in the host cell or introduced into the host cell along with the receptor.

G2A receptor agonists isolated as described above can be used to promote cell cycle arrest at the G2/M transition in malignant cells, particularly hematopoietic cells such as leukemia cells and lymphoma cells, both in vitro and in vivo. The DNA sequence can also be used as a probe to search for additional closely-related family members which may play similar roles in oncogenesis.

As determined using mouse knock-out experiments, loss of function of G2A makes lymphoid cells more susceptible to leukemogenesis and results in hyper-proliferative T lymphocytes. Thus, agonists to the G2A receptor would be useful in limiting T cell responses and could be used to treat a broad range of autoimmune and inflammatory disorders resulting from excessive responses of T lymphocytes (T cell hyperproliferation). These disorders include, but are not limited to, rheumatoid arthritis, psoriasis, inflammatory bowel diseases (e.g., Crohn's disease, colitis), T cell and immature B cell malignancies and diabetes. Thus, the assays for identifying agonists of G2A described herein can also be used to identify compounds which can be used to treat T cell-mediated autoimmune and inflammatory disorders. These assays comprise the steps of determining whether a compound binds to G2A, and testing compounds which bind to G2A to determine whether they activate the G2A receptor using any of the methods described herein.

G2A is expressed in some normal bone marrow cells, and is expressed in spleen. Thus, it is possible that G2A regulates blood cell development. Regulation of the activity of the G2A (by antibodies, inhibitory or stimulatory drugs, or natural ligands) may be clinically useful in restoring the normal number and function of the blood cell population with suppressed hematopoiesis, such as that which occurs after treatment to obtain immune depression for organ transplants or after cytotoxic cancer therapy.

Since we have isolated both murine and human G2As, the cDNAs can be used to isolate the homologue of the G2As in other species. Identification of the homologues in other species may lead to a cure for the diseases mentioned above in animals, and will therefore have broad applications in veterinary medicine. The amino acid sequence information of the highly conserved regions of the mutine and human G2As can be used to develop antibodies or drugs that can be used to treat diseases in both human and animals.

B. Uses of the Invention

A wide variety of syndromes characterized by inflammation and autoimmunity discussed as well as models for characterizing them that are well described in the art (see e.g. W073349A1, which is incorporated herein by reference). In this context, the methods of the invention provided herein are shown have a number of different utilities. In particular, the identification of the one or more ligands which modulate the activity a cellular receptor (particularly one shown to be associated with pathological conditions) is a crucial element in many typical protocols that are employed in the art for a variety of purposes. Such uses include for example, the determination of ligand concentrations, the development of ligand agonists and antagonists and the characterization of the physiological roles of these ligands and their receptors. Consequently, a wide variety of protocols based on methods pertaining to such ligand-receptor interactions are described for these purposes (see, e.g., U.S. Pat. No. 5,871,909, U.S. Pat. No. 5,030,576, U.S. Pat. No. 6,110,737 and U.S. Pat. No. 6,040,290). In this context, the disclosure provided herein allows for example, a comprehensive characterization of the role of G2A in normal physiological processes as well as its associated pathological conditions including inflammation and autoimmunity.

In addition, these methods may be employed in protocols for treating pathological conditions in mammals such as cancer or immune-related diseases. In typical methods, a G2A ligand or a competitor or agonist or antagonist thereof, is administered to a mammal, alone or in combination with still other therapeutic agents or techniques.

Diagnosis in mammals of the various pathological conditions described herein can be made by the skilled practitioner. Diagnostic techniques are available in the art which allow, e.g., for the diagnosis or detection of cancer or immune related disease in a mammal. For instance, cancers may be identified through techniques, including but not limited to, palpation, blood analysis, x-ray, NMR and the like. Immune related diseases can also be readily identified. For example, in systemic lupus erythematosus, the central mediator of disease is the production of auto-reactive antibodies to self proteins/tissues and the subsequent generation of immune-mediated inflammation. Multiple organs and systems are affected clinically including kidney, lung, musculoskeletal system, mucocutaneous, eye, central nervous system, cardiovascular system, gastrointestinal tract, bone marrow and blood. Other typical pathological conditions are described below.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, interstitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing sponylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of anti-nuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjogren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinunra is a result of production of anti-bodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet β cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including Multiple Sclerosis; idiopathic demyelinating polyneuropathy or Guillain-Barr syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+T lymphocytes are the predominant cell type at lesions. The mechanism of oligodendrocyte cell death and subsequent demyelination is not known but is likely T lymphocyte driven.

Inflammatory and Fibrotic Lung Disease, including Eosinophilic Pneumonias; Idiopathic Pulmonary Fibrosis, and Hypersensitivity Pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative.

Other diseases in which intervention of the immune and/or inflammatory response have benefit are infectious diseases including but not limited to viral infection (including but not limited to AIDS, hepatitis A, B, C, D, E) bacterial infection, fungal infections, and protozoal and parasitic infections (molecules (or derivatives/agonists) in which stimulation of an immune response can be utilized therapeutically to enhance the immune response to infectious agents), diseases of immunodeficiency (molecules/derivatives/agonists) which stimulate an immune response can be utilized therapeutically to enhance the immune response for conditions of inherited, acquired, infectious induced (as in HIV infection), or iatrogenic (i.e. as from chemotherapy) immunodeficiency), and neoplasia.

The G2A ligand, agonist or antagonist thereof is preferably administered to the mammal in a carrier; preferably a pharmaceutically-acceptable carrier. Suitable carriers and their formulations are described in *Remington's Pharmaceutical Sciences,* 16th ed., 1980, Mack Publishing Co., edited by Oslo et al. Typically, an appropriate amount of a pharmaceutically-acceptable salt is used in the formulation to render the formulation isotonic. Examples of the carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing, for example, the G2A ligand LPC, which matrices are in the form of shaped articles, e.g., films, liposomes or microparticles. It will be apparent to those persons skilled in the art that certain carriers may be more preferable depending upon, for instance, the route of administration and concentration of G2A ligand being administered.

The G2A ligand, agonist or antagonist thereof can be administered to the mammal by injection (e.g., intravenous, intraperitoneal, subcutaneous, intramuscular, intraportal), or by other methods such as infusion that ensure its delivery to the bloodstream in an effective form. The G2A ligand, agonist or antagonist thereof may also be administered by isolated perfusion techniques, such as isolated tissue perfusion, to exert local therapeutic effects. Local or intravenous injection is preferred.

Effective dosages and schedules for administering the G2A ligands may be determined empirically, and making such determinations is within the skill in the art. Those skilled in the art will understand that the dosage of G2A ligand, agonist or antagonist thereof that must be administered will vary depending on, for example, the mammal which will receive the G2A ligand, agonist or antagonist thereof, the route of administration, the particular type of molecule used (e.g. LPC, SPC, antibody etc.) used and other drugs being administered to the mammal.

The G2A ligand, agonist or antagonist thereof may also be administered to the mammal in combination with effective amounts of one or more other therapeutic agents. The one or more other therapeutic agents or therapies may include, but are not limited to, chemotherapy (chemotherapeutic agents), radiation therapy, immunoadjuvants, growth inhibitory agents, cytotoxic agents, and cytokines.

Chemotherapies contemplated by the invention include chemical substances or drugs which are known in the art and are commercially available, such as Doxorubicin, 5-Fluorouracil, etoposide, camptothecin, Leucovorin, Cytosine arabinoside, Cyclophosphamide, Thiotepa, Busulfan, Cytoxin, Taxol, Methottexate, Cisplatin, Meiphalan, Vinblastine and Carboplatin. Preparation and dosing schedules for such chemotherapy may be used according to manufacturer's instructions or as determined empirically by the skilled practitioner. Preparation and dosing schedules for such chemotherapy are also described in Chemotherapy Service Ed., M. C. Perry, Williams & Wilkins, Baltimore, Md. (1992).

The chemotherapy is preferably administered in a pharmaceutically-acceptable carrier, such as those described above. The mode of administration of the chemotherapy may be the same as employed for the G2A ligands or it may be administered to the mammal via a different mode. For example, the G2A ligands may be injected while the chemotherapy is administered orally to the mammal.

Radiation therapy can be administered to the mammal according to protocols commonly employed in the art and known to the skilled artisan. Such therapy may include cesium, iridium, iodine or cobalt radiation. The radiation therapy may be whole body radiation, or may be directed locally to a specific site or tissue in or on the body. Typically, radiation therapy is administered in pulses over a period of time from about 1 to about 2 weeks. The radiation therapy may, however, be administered over longer periods of time. Optionally, the radiation therapy may be administered as a single dose or as multiple, sequential doses.

The G2A ligand, agonist or antagonist thereof may be administered sequentially or concurrently with one or more other therapeutic agents. The amounts of this molecule and therapeutic agent depend, for example, on what type of drugs are used, the pathological condition being treated, and the scheduling and routes of administration but would generally be less than if each were used individually.

Following administration of a G2A ligand to the mammal, the mammal's physiological condition can be monitored in various ways well known to the skilled practitioner.

It is contemplated that the antagonist or blocking G2A antibodies may also be used in therapy. For example, a G2A antibody could be administered to a mammal (such as described above) to block G2A receptor binding to LPC and/or SPC.

The therapeutic effects of the G2A ligands of the invention can be examined in in vitro assays and using in zero animal models. A variety of well known animal models can be used to further understand the role of the G2A ligands identified herein in the development and pathogenesis of for instance, immune related disease or cancer, and to test the efficacy of the candidate therapeutic agents. The in in vivo nature of such models makes them particularly predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g. subcutaneous injection, tail vein injection, spleen implantation, intraperitoneal implantation, and implantation under the renal capsule.

Animal models, for example, for graft-versus-host disease are known. Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in Current Protocols in Immunology, unit 4.3.

An animal model for skin allograft rejection is a means of testing the ability of T cells to mediate in vivo tissue destruction which is indicative of and a measure of their role in anti-viral and tumor immunity. The most common and accepted models use murine tail-skin grafts. Repeated experiments have shown that skin allograft rejection is mediated by T cells, helper T cells and killer-effector T cells, and not antibodies. [Auchincloss, H. Jr. and Sachs, D. H., *Fundamental Immunology*, 2nd ed., W. E. Paul ed., Raven Press, NY, 1989, 889–992]. A suitable procedure is described in detail in Current Protocols in Immunology, unit 4.4. Other transplant rejection models which can be used to test the compositions of the invention are the allogeneic heart transplant models described by Tanabe, M. et al., *Transplantation,* (1994) 58:23 and Tinubu, S. A. et al., *J. Immunol.,* (1994) 4330–4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in Current Protocols in Immunology, unit 4.5.

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The G2A ligands of the invention can be tested for activity against autoimmune arthritis using the protocols described in Current Protocols in Immunology, above, units 15.5. See also the model using a monoclonal antibody to CD18 and VLA-4 integrins described in Issekutz, A. C. et al., *Immunology,* (1996) 88:569.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compositions of the invention for activity and effectiveness in the treatment of asthma are described by Wolyniec, W. W. et al., *Am. J. Respir. Cell Mol. Biol.*, (1998) 18:777 and the references cited therein.

Additionally, the G2A ligands, agonists or antagonists thereof of the methods of the invention can be tested on animal models for psoriasis like diseases. For example, the G2A ligands used in the methods of the invention can be tested in the scid/scid mouse model described by Schon, M. P. et al., *Nat. Med.*, (1997) 3:183, in which the mice demonstrate histopathologic skin lesions resembling psoriasis. Another suitable model is the human skin/scid mouse chimera prepared as described by Nickoloff, B. J. et al., *Am. J. Path.*, (1995) 146:580.

Various animal models are well known for testing anti-cancer activity of a candidate therapeutic composition. These include human tumor xenografting into athymic nude mice or scid/scid mice, or genetic murine tumor models such as p53 knockout mice.

Recombinant (transgenic) animal models can be engineered by introducing the coding portion of the molecules identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA,* 82, 6148–615 [1985]); gene targeting in embryonic stem cells (Thompson et al., *Cell,* 56, 313–321 [1989]); electroporation of embryos (Lo, *Mol. Cel. Biol.,* 3, 1803–1814 [1983]); sperm-mediated gene transfer (Lavitrano et al., *Cell* 57, 717–73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA,* 89, 6232–636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals may be further examined for signs of immune disease pathology, for example by histological examination to determine infiltration of immune cells into specific tissues or for the presence of cancerous or malignant tissue.

As shown in Example 14, "knock out" animals can be constructed which have a defective or altered gene encoding a polypeptide identified herein, as a result of homologous recombination between the endogenous gene encoding the polypeptide and altered genonic DNA encoding the same polypeptide introduced into an embryonic cell of the animal. For example, cDNA encoding a particular polypeptide can be used to clone genomnic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocardinonmas and Embronic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

In another embodiment of the invention, methods for employing the G2A ligands in diagnostic assays are provided. For instance, the G2A ligands may be employed in diagnostic assays to detect expression or overexpression of G2A in specific cells and tissues. Various diagnostic assay techniques known in the art may be used, such as in vivo imaging assays, in vitro competitive binding assays, direct or indirect binding assays. The G2A ligands used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the G2A ligand to the detectable moiety may be employed, including those methods described by Hunter et al., *Nature*, 144:945 (1962); David et al., *Biochemistry*, 13:1014–1021 (1974); Pain et al., *J. Immunol. Meth.*, 40:219–230 (1981); and Nygren, *J. Histochem. and Cytochem.*, 30:407–412 (1982).

G2A ligands also are useful for the affinity purification of G2A from recombinant cell culture or natural sources. In this process, the G2A ligands are immobilized on a suitable support, such a Sephadex resin or filter paper, using methods well known in the art. The immobilized ligand then is contacted with a sample containing the G2A to be purified, and thereafter the support is washed with a suitable solvent that will remove substantially all the material in the sample except the G2A, which is bound to the immobilized ligand. Finally, the support is washed with another suitable solvent that will release the G2A from the ligand.

In a further embodiment of the invention, there ate provided articles of manufacture and kits containing materials useful for treating pathological conditions or detecting or purifying G2A. The article of manufacture comprises a container with a label. Suitable containers include, for example, bottles, vials, and test tubes. The containers may be formed from a variety of materials such as glass or plastic. The container holds a composition having an active agent which is effective for treating pathological conditions or for detecting or purifying G2A. The active agent in the composition is a G2A ligand and preferably, comprises SPC and or LPC. The label on the container indicates that the composition is used for treating pathological conditions or detecting or purifying G2A, and may also indicate directions for either in vivo or in vitro use, such as those described above.

The kit of the invention comprises the container described above and a second container comprising a buffer. It may further include other materials desirable from a commercial and user standpoint, including other buffers, diluents, filters, needles, syringes, and package inserts with instructions for use.

EXAMPLES

Example 1

Illustrative General Methods and Materials Involving G2A Molecules

Plasmid constructs, cell lines, preparation of viral stocks, generation of antibodies The WT p185 BCR-ABL and the SH2 mutant were cloned into the pSRαMSV vector (Muller et al., *Mol. Cell Biol.* 11:1785–1792. 1991) under the control of the LTR promoter as previously described (Afar et al., *Science* 264:424–426, 1994; Pendergast et al., *Cell* 75:175–185, 1993). The pSRαMSV vector was used to produce helper-free retroviral stocks by transient transfection of 293T cells along with the ψ packaging vector (Pear et al., *Proc. Natl. Acad, Sci. U.S.A.*, 90:8392–8396, 1993; Afar et al., *Science* 264:424–426, 1994). A 13-amino acid peptide (KDSEETHLPTELS; SEQ ID NO: 5) corresponding to the C-terminal intracellular portion of the murine G2A was synthesized and injected into rabbit for antibody production (Babco, Berkeley, Calif.). Five production bleeds were obtained. To generate the antibodies against the murine N-terminal extracellular portion of the G2A, a GST-Mu-G2A-N fusion construct was made by PCR using GST-Mu-N2A-N5' and GST-Mu-N2A-N3' primers.

Briefly, PCR was performed in a total of 100 µl reaction mixture containing 20 ng template, 30 µl 3.3× XL buffer (Perkin Elmer, Norwalk, Conn.), 6 µl 25 mM magnesium acetate, 2 µl dNTPs (10 mM each nucleotide), 20 pmol of GST-Mu-N2A-N5' and GST-Mu-N2A-N3' primers, and 1 µl rTth polymerase (Perkin Elmer). The cycling conditions were 95° C. for 5 min, 30 cycles of denaturation at 94° C. for 0.5 min, annealing at 56° C. for 1 min and elongation at 72° C. for 1 min. After incubation at 72° C. for 10 min, the amplified PCR fragment was digested with BamHI and EcoRI (Boehringer Mannheim, Indianapolis, Ind.) in Buffer B (10 mM Tris, 5 mM $MgCl_2$, 100 mM NaCl, 1 mM β-mercaptoethanol, pH 8.0, Boehringer Mannheim), and fractionated on an agarose gel. The DNA fragment was excised, purified using Geneclean™ (Bio 101, La Jolla, Calif.) and cloned into the pGEX-2T vector (Pharmacia Biotech) at the BamHI/EcoRI sites. Approximately 50 ng pGEX-2T BamHI/EcoRI fragment was ligated to the PCR product at a 1:3 molar ratio in 1× T4 DNA ligase buffer (50 mM Tris-HCl (pH 7.8), 10 mM $MgCl_2$, 10 mM DTT, 1 mM ATP, 50 µg/ml BSA) and 1 µl T4 DNA ligase (New England Biolabs, Beverly, Mass.) in a 10 µl reaction volume at 16° C. overnight. Transformation was performed by mg 10% of the ligation reaction with 100 µl of DH5α competent *E. coli* cells on ice for 20 min. After heat shock at 42° C. for 2 min and incubation on ice for 2 min. ml TYE was added and the transformed cells were further incubated at 37° C. for 1 hr. The transformation mix was plated out on TYE plates containing ampicillin (50 µg/ml). One positive clone containing the insert was identified. The plasmid was sequenced to ensure the proper fusion of the murine N-terminal extracellular portion of G2A to GST.

Example 2

Assessing G2A Via Northern Analysis

Northern analysis

RNA was purified using the Ultraspec RNA isolation system (Biotecx laboratories, Inc., Houston, Tex.). To examine the expression level of a gene of interest, a DNA fragment of the gene was labeled using the Prime-it II random primer labeling kit (Stratagene). Northern blotting was performed as previously described (Schneider at al., *Cell* 54:787–793, 1993). Briefly, the RNA samples were fractionated in an agarose gel (1% agarose, 20 mM phosphate, pH 7.0, 7% formaldehyde), transferred to Nitro-Pure nitrocellulose transfer membrane (Micron Separations, Inc. Westborough, Mass.) using 20× SSC. The blot was baked at 80° C. for 2 h and prehybridized in the prehybridization buffer (50% formamide, 5× SSC, 1× Denhardt's, 50 mM phosphate stock buffer and 0.25 mg/ml salmon sperm DNA) for 4 h. The blot was then hybridized overnight at 42° C. with the probe in 8 ml prehybridization buffer and 2 ml 50% dextran sulfate. The blot was washed once with 2× SSC, 0.1% SDS at room temperature for 30 min, and once with 2× SSC, 0.1% SDS at 60° C. for 30 min. The blot was exposed to x-ray film at −70° C.

To assess whether G2A affects hematopoietic cell transformation by BCR-ABL, a bone marrow transformation assay was applied to quantitatively measure the kinetics of the BCR-ABL-mediated transformation in the presence or absence of G2A. Retroviral-mediated expression of BCR-ABL in primary murine bone marrow cells results in the outgrowth of stromal cell-dependent pre-B cultures (McLaughlin et al., 1987). The growth rate of pre-B cells from infected marrow is directly dependent on the strength of the tyrosine kinase activity. To monitor the protein level of ectopically-expressed G2A, a chimeric G2A-GFP fusion protein was generated whose level could be quantitatively measured by FACS. The assay was performed as described in the following example.

Example 3
Use of G2A to Modulate the Transformation of Lymphoid Cells

Murine bone marrow transformation assay and Reconstitution of Irradiated Mice

Fresh bone marrow cells from the tibias and femurs of 3- to 4-week-old BALB/c mice were isolated and infected with retrovirus encoding either the WT BCR-ABL p185 along with the G2A-GFP fusion protein (pMSCV G2A-GFP IRES p185 WT) or GFP as a control. IRES is an internal ribosome entry binding site element which improves the yield of the expressing clones. The anti-sense version of G2A-GFP and GFP were also used as controls. The cells were plated at a density of $5 \times 10^6$ cells per 6-cm dish in RPMI containing 10% fetal bovine serum and β-mercaptoethanol ($5 \times 10^{-5}$ M) as previously described (McLaughlin et al., *Mol. Cell. Biol.* 9:1866–1874, 1989). The viral stocks were prepared as described (Goga et al., *Cell* 82:981–988, 1995). Liquid cultures were plated in triplicates and monitored for pre-B cell growth. Transformed pre-B-lymphoid cells were counted at various days following infection. The Expression of G2A-GFP and GFP were confirmed by FACS analysis.

During the first two weeks of the assay, G2A expression with BCR-ABL delayed the induction of pre-B cell outgrowth compared to BCR-ABL plus GFP or the G2A-GFP anti-sense control. Bone marrow cultures transformed by BCR-ABL in the absence of G2A reached confluency (>1× $10^7$ cells per 3 ml culture) within 1½ weeks, whereas it took nearly three weeks to reach saturation in the presence of G2A. Similar results were obtained in three independent experiments. This indicates that G2A slows the transformation process of BCR-ABL in lymphoid cells. Because G2A is linked to GFP, protein levels could be measured in these cultures during the three-week period by FACS. GFP alone did not significantly change its expression levels; however, G2A-GFP protein levels decreased gradually and after three weeks were nearly undetectable. This counter-selection against B cells expressing high levels of G2A strongly suggests an anti-oncogenic effect of G2A as seen in fibroblasts.

Since G2A is not natively expressed but induced by BCR-ABL in pre-B cells, it was determined whether the expression of G2A was regulated during different states of B cell development. B lymphocytes are generated from hematopoietic stem cells by successive steps of differentiation during which a diverse repertoire of antigen receptors are generated by immunoglobulin gene rearrangement. The initiation of D-J rearrangement occurs in the early pro-B cells and at the pre-B cell stage, intact heavy chains are produced. The light chain genes then undergo rearrangement resulting in the expression of a complete IgM protein on the surface of immature B cells which then differentiate into IgM and IgD-expressing mature B cells capable of responding to antigen.

Transcriptional regulation of G2A in B cells

To examine the expression of G2A, mouse bone marrow B cells were fractionated into pro-B, pre-B, immature B and mature B cells to examine the expression of G2A in different developmental compartments in lymphoid cells. A semi-quantitative RT-PCR method was used to measure the RNA levels of G2A. The G2A transcript is almost exclusively present in pro-B cells which coincidentally have the highest proliferation potential and are undergoing recombination. Extended PCR cycles revealed a low level of G2A transcript in pre-B, immature B and mature B cells.

Rabbit polyclonal anti-G2A antibodies were used to examine the protein level of GZA in the same pro-B, pre-B, immature B and mature B cell fractions. High levels of G2A protein were detected in pro-B cells whereas very weak staining was present in the other three fractions of B cells using FACS. These results show that the mRNA level of G2A corresponds to G2A protein level and that the effect of GZA may be predominantly restricted in pro-B cells.

To determine whether natural stimuli could activate G2A in more mature B cells, we used a human B cell line (Ramos) as a model system in which G2A expression is at a basal level. Ramos cells were activated by anti-IgM antibodies to examine whether activation of B cell receptors (BCR) induced G2A transcription.

Example 4
Illustrative G2A Constructs and Methods

Insertion of mouse and human G2As into expression vectors

G2A cDNA was inserted into several eukaryotic expression vectors. Any of these constructs can be used to transfect eukaryotic cells, preferably mammalian cells, for production of recombinant G2A using methods well known in the art. Such methods are described in, for example, Sambrook et al. (*Molecular Biology: a Laboratory Manual*, Cold Spring Harbor Laboratory, 1988; Ausubel, *Current Protocols in Molecular Biolog*, 1989). Such eukaryotic cells include Rat-1, NIH 3T3, 293T, CHO, COS-7 and BHK cells. The G2A can also be inserted into a baculovirus expression vector which is used to infect Sf9 insect cells using methods well known in the art.

N-terminal flag-tagged mouse G2A in the pCRII vector (Invitrogen) was used for in vitro transcription and translation of mouse G2A and for making probes for Northern, S1 or in situ analysis. Reverse transcription of RNA into first strand cDNA was performed using RNA isolated from bone marrow cells transformed with WT BCR-ABL. PCR was performed using 10 pmol of MuN2Aflag5 and MuN2A3'-1 primers in 50 μl reaction mixture containing 1× pfu buffer (20 mM Tris-HCl, pH 8.75, 10 mM KCl, 10 mM $(NH_4)_2SO_4$, 2 mM $MgSO_4$, 0.1% Triton X-100, 100 μg/ml BSA) (Sigma). The cDNA was first denatured at 94° C. for 3 min. PCR was performed by 35 cycles of denaturation at 94° C. for 0.5 min., annealing at 62° C. for 1 min. and elongation at 75° C. for 3 min. The amplified PCR product was cloned into the pCRII vector (invitrogen) according to the manufacturer's instructions.

The pSRα-Flag-G2A tk Neo expression vector is a retroviral expression vector for expression of mouse and human G2As in mammalian cells. In this construct, the Neo gene is under control of the herpes simplex virus thyrnidine kinase (tk) promoter for selection of infected cells with G418. The EcoRI insert from pCRII-Flag-Mu-G2A was excised and cloned into pSRα-Flag-G2A tk Neo at the EcoRI cloning site upstream of the TK promoter.

pCRII-Mu-G2A, the untagged version of pCR-Flag-Mu-G2A, was used for in vitro transcription and translation, and for making probes for Northern, S1 or in situ analysis. For construction of this vector, RT-PCR was performed using primers MuN2A5'Eco and MuN2A3'-1 using the protocol described for pCRII-Mu-G2A. The amplified PCR product was cloned into the pCRII vector. In vitro transcription and translation were performed using the TNT-coupled reticulocyte lysate system (Promega, Madison, Wis.) according to the manufacturer's instructions. The in vitro transcription and translation of Mu-G2A revealed a protein product having a molecular weight of about 42 kDa which is similar to the calculated molecular weight of mouse G2A.

pCRII-Mu-G2A-HA, the C-terminal HA-tagged version of mouse G2A was used for in vitro transcription/translation and for labeling proves for Northern, S1 or in situ analysis. For construction of this vector, RT-PCR was performed using primers MuN2A5'Eco and MuN2A3'HA using the plasmid vector pGD-Mu-G2A-HA containing the HA-tagged version of murine G2A. The PCR product was cloned into the pCRII vector (Invitrogen).

For construction of pMu-G2A-GFP, the mouse G2A was fused to the N-terminal green fluorescence protein (GFP) in the pEGFP-N1 vector (Clontech). The murine G2A was amplified using primers specific for murine G2A and fused in frame with GFP in the pEGFP-N1 vector. The expression of the Mu-G2A-GFP fusion protein was confirmed by FACS analysis. The fusion protein will allow following the expression of murine G2A in mammalian cells and functional analysis of the G2A. Similarly, for pEGF-Hu-G2A-GFP, human G2A was fused to the N-terminal green fluorescence protein (GFP) in the pEGFP vector. The human G2A is amplified using primers specific for human G2A and fused in frame with GFP in the pEGFP vector. The fusion protein allows following the expression of human G2A in mammalian cells and functional analysis of the G2A.

Example 5
Illustrative Animal Model for Evaluating G2A

Acceleration of leukemogenesis in vivo by BCR-ABL

One day prior to reconstitution, severe combined immunodeficient (SCID) mice were sublethally irradiated with 275 rads. Whole bone marrow was isolated and infected with retrovirus as described above. Three hours post-infection, the bone marrow was injected intravenously into the tail veins of recipient SCID mice. Animals are monitored for signs of sickness over a twelve-week period. Sick mice are sacrificed and tissues are analyzed for BCR-ABL expression by Western Blotting. Blood and spleen samples are analyzed by fluorescence activated cell sorting (FACS). Blood smears are analyzed by Wright/Giemsa staining. Mice which were injected with WT BCR-ABL exhibit significantly more leukemogenesis than mice injected with the SH2 mutant.

To evaluate the effect of BCR-ABL-regulated genes on the oncogenic potential of BCR-Abl, a soft agar fibroblast colony formation assay was used. BCR-ABL confers anchorage-independent growth of rodent fibroblasts (Rat-1) in soft agar and the numbers of colonies quantitatively reflects its transformation potency (Lugo et al., Mol. Cell. Biol. 9:1263–1270, 1989). This assay is described below.

Example 6
Modulation of a Tumor Suppression Activity Via G2A Gene Expression

G2A functions as a tumor suppressor gene

The G2A, G2A-GFP, or G2A indicator cell lines were generated by infection of Rat-1 fibroblasts with helper-free retroviruses followed by selection in G418 (0.4 mg/ml) for approximately 1–2 weeks. The expression of G2A-GFP and GFP were confirmed by FACS analysis using a FACScan (Becton Dickinson). Transformation by various oncogenes was measured using a soft agar assay as described (Lugo et al., supra.). Briefly, the indicator cell lines were plated at a density of $6 \times 10^4$ cells/6 cm dish overnight. Infection was performed for 3 hours at 37° C. using 1 ml of virus stock with 8 µg/ml polybrene. Two days post-infection, cells were harvested and plated in agar at a density of $1 \times 10^4$ cells/6 cm dish in duplicate. Dishes were re-fed at one week and colonies were counted after three weeks. Colonies greater than 0.5 mm in diameter were scored positive.

G2A or Neo-expressing Rat-1 cell lines were also generated by retroviral infection and G418 selection, followed by superinfection with a retroviral stock expressing BCR-ABL. Similar percentages of cells were infected by BCR-ABL-expressing retrovirtuses as shown by FACS analysis and Western blotting.

Most of the genes isolated by the RDA screen had no discernible effects on the oncogenic potential of BCR-ABL. However, G2A strongly antagonized the ability of BCR-ABL to form colonies in soft agar. As listed in Tables 4A–B, overexpression of G2A suppressed the number of agar colonies induced by BCR-ABL p185 approximately five fold. G2A epitope-tagged with GFP still retained some ability to block BCR-ABL-mediated transformation in Rat-1 cells. G2A also blocked agar colonies induced by Gag-BTK*, an activated version of Bruton tyrosine kinase, and the transcription factor Myc. Interestingly, G2A failed to block transformation mediated by v-ABL or the serine kinase oncogene v-Mos. v-ABL and v-Mos may transform cells by mechanisms distinct from BCR-ABL, Myc and Gag-BTK*. Since BTIC has been shown to play a critical role in B cell development (Tsukada et al., Cell 72:279–290, 1993; Rawlings et al., Immunological Rev. 138, 1994), the ability of G2A to block Gag-BTK* transformation also suggests that the G2A may also be a regulator of BTK during B cell development. Similarly, overexpression of the G2A gene suppressed the transformation of bone marrow cells. In addition, in vivo tumor formation and leukemogenesis assays can be used to analyze the effect of G2A on malignant phenotypes induced by various organisms. Transfection or infection of cells in vitro, ex vivo or in vivo with expression constructs, preferably retroviral or adenoviral vector constructs, encoding G2A results in inhibition of cell proliferation. In a preferred embodiment of the invention, bone marrow is isolated from an individual with leukemia by standard methods, and the bone marrow cells are infected with the retroviral construct encoding G2A as described herein. The bone marrow is then returned to the patient. Overexpression of G2A in the bone marrow cells inhibits farther leukemogenesis and results in a significant clinical improvement.

TABLE 1A

| Oncogene | Rat-1 | Rat-1/G2A |
|---|---|---|
| Ø | 0 | 0 |
| BCR-ABL p185 | >1300 | 226 ± 40 |
| v-ABL | 552 ± 28 | 444 ± 24 |
| Myc | >1300 | 388 ± 20 |

TABLE 1B

| Oncogene | Rat-1/GFP | Rat-1/G2A-GFP |
|---|---|---|
| Ø | 9 ± 1 | 2 ± 1 |
| BCR-ABL p185WT | >1300 | 608 ± 40 |
| v-ABL | 432 ± 64 | 496 ± 16 |
| Gag-BTK* | 88 ± 12 | 3 ± 1 |
| v-Mos | 224 ± 16 | 172 ± 20 |

Rat-1/Neo cells exhibited a prominent elongation phenotype typical of transformation by BCR-ABL. G2A blocked this gross morphological change by BCR-ABL. When these same cell populations were plated in agar, wild type BCR-ABL alone gave rise to more than 1,000 colonies after three weeks. In contrast, BCR-ABL, co-expressed with G2A, yielded more than 5-fold fewer colonies indicating that G2A antagonizes BCR-ABL-mediated transformation. Evaluation of agar colonies recovered and expanded in liquid culture by FACS analysis showed that the cells that grew in agar lose expression of G2A but not BCR-ABL. Thus, G2A has an anti-proliferative effect on transformation.

To determine whether the G2A was involved in the regulation of cell cycle progression, Rat-1 fibroblasts were infected with retrovirus expressing G2A gene as described in the following example.

Example 7
Modulation of Cell Cycling Via G2A Gene Expression

G2A induces cell cycle arrest in Rat-1 cells during mitosis

Rat-1 cells were selected with G418 (0.4 mg/ml) for one week and grown to either subconfluence or confluence. The cells were harvested by trypsinization and pelleted by centrifugation. The cells were then resuspended in Vindelov's stain (5 mM Tris, pH 7.4, 5 mM NaCl, 0.05% NP-40, 0.04 mg/ml propidium iodide, 5 μkg/mi RNase) and incubated on ice for 15 min in the dark. Flow cytometric analysis was performed using FACScan (Lysis II program). As shown in Table 2, expression of G2A increases the percentage of cells in the G2/M phase of the cell cycle. Examination of Rat-1 cells expressing the G2A under the microscope revealed a higher percentage of cells with bi- or poly-nuclei (approximately 5–10% versus less than 1% observed in parental Rat-1 cells), suggesting that G2A-expressing cells were likely to be arrested at the anaphase of mitosis. Taken together, these data suggest that the G2A may function as a tumor suppressor gene and is involved in cell cycle arrest during mitosis. The biological properties of the G2A share similarities with $p^{53}$, a tumor suppressor gene. Both G2A and p53 negatively regulate cell growth and induce cell cycle arrest. Interestingly, their expressions are both upregulated by DNA damage-inducing agents such as X-rays. The ability of certain oncogenes to induce the expression of G2A and the ability of G2A to block the oncogenic potential of these genes suggest that the G2A may comprise a self-defense mechanism for cells to counter ill-fated transformation phenotypes.

TABLE 2

|  | G1 | S | G2/M | dead cells |
|---|---|---|---|---|
| Rat-1 (subconfluent) | 60% | 14% | 25% | 1% |
| Rat-1/G2A (subconfluent) | 47% | 14% | 37% | 2% |
| Rat-1 (confluent) | 64% | 11% | 24% | 1% |
| Rat-1/G2A (confluent) 49% | 12% | 36% | 3% | |

Example 8
Modulation of Mitosis Via GZA Gene Expression

G2A blocks the progression of mitosis in NIH3T3 cells

The anti-oncogenic effect of G2A in fibroblasts and lymphoid cells, as well as the induction of G2A by cell cycle arrest-associated DNA damaging agents suggested that G2A may be involved in cell cycle regulation. To investigate this possibility, retroviruses expressing G2A, G2A-GFP fusion protein or a GFP control were used to infect NIH3T3 cells which are easily infectable (>90% of infection). Transient infection with a G2A retrovirus reproducibly increased the fractions of cells at G2/M by approximately 10% under normal growing conditions (10% FBS), strongly indicating that G2A arrests cells at G2/M. This percentage increase is comparable to that caused by overexpression of p53. To further examine whether G2A confers a G2/M block under serum starvation conditions, NIH3T3 cells expressing G2A, G2A-GFP fusion or GFP control were cultured in the presence of 0.1% FBS for 48 hours. Cells were harvested and the DNA content analyzed by FACS. Two days after serum starvation, 95% of the control cells expressing GFP alone contained 2N DNA content, suggesting that these cells were arrested at G1 upon growth factor deprivation. However, cells expressing G2A or G2A-GFP fusion protein still exhibited a large percentage of cells with 4N DNA content (39% and 34%, respectively), suggesting that G2A blocks the exit of cells from G2/M during growth factor deprivation. An increase in the 8N DNA content which is accentuated during growth factor deprivation, and an increase of approximately 5–10% of multiple nuclei in cells expressing G2A or G2A-GFP, were also observed. This suggests that although there is still endoduplication of DNA in cells expressing G2A, these cells failed to undergo cytokinesis suggesting a potential additional role of G2A in perturbing the mitotic spindle checkpoint.

Examination of the G2A primary sequence reveals the presence of a "destruction box" found primarily in cyclin gene products which may serve as a recognition motif for the conjugation of ubiquitin. Cytosolic ubiquitinated cyclins are degraded by the multisubunit 26S proteosome. There is some evidence that certain GPCRs such as yeast Ste2 are ubiquitinated which is required for their internalization for subsequent degradation. A mote recent report demonstrated the role of ubiquitinization of a GPCR for internalization of the signal while it escaped degradation by the proteasome (Terrell et al., *Molecular Cell* 1:193–202, 1998). The presence of the "destruction box" in G2A raised the possibility that G2A may be ubiquitinated and down regulated or internalized via the ubiquitin pathway.

Example 9
General Materials and Methods For Modulating G2A Activity Via High and Low Affinity Ligands Materials LPCs (14:0, 16:0, 18:0 and 18:1), LPI, LPA, C16-PAF, C16-lysoPAF were from Avanti Polar Lipids, Inc. (Alabaster, Ala.). Sphingomyelins (16:0 and 18:0), S-1-P and SPC were from Toronto Research Chemicals (Toronto, ON) or Matreya, Inc. (Pleasant Gap, Pa.). BN52021 was from Biomol (Plymouth Meeting, Pa.). [$^3$H] LPC and [$^3$H] SPC were custom synthesised by Amersham Pharmacia Biotech, Buckinghamshire, England (102 Ci/mmol, 1 mCi/ml for [$^3$H] 18:0 LPC and 68 Ci/mmol, 1 mCi/mil for [$^3$H] SPC). [$^3$H] 16:0 LPC (60 Ci/mmol) was purchased from American Radiolabelled Chemicals Inc. (St Louis, Mo.).

Cell Culture

MCF 10A cells (passage 34) were purchased from the Barbara Ann Karmanos Cancer Institute (Detroit, Mich.) and cultured following their recommendations. HEK 293 and CHO cells were obtained from ATCC and cultured in DMEM supplemented with 10% FBS.

Calcium assay

MCF 10A cells were cultured in specialised glass-bottom dishes (Bioptech, Inc., Butler, Pa.) and loaded with Fura-2/AM (1 mM; Molecular Probes) at 37° C. for 30 minutes in HEPES buffered saline (pH 7.4) containing 125 mM NaCl, 5 mM KCl, 1.2 mM $MgSO_4$, 11 mM glucose, 1.8 mM $CaCl_2$, 25 mM HEPES, 0.2% BSA. Loaded cells were washed, placed in HEPES buffeted saline without BSA, and incubated for 30 minutes at ambient temperature ensure dye hydrolysis by cytosolic esterases. Using a dual-wavelength spectrofluorometer (RFK-6002, Photon Technology Int'l, So. Brunswick, N.J.) coupled to an inverted fluorescence microscope (Olympus, IX-70, Lake Success, N.Y.), GFP-positive cells were identified using an excitation wavelength of 488 nm, a dichroic 505 nm long-pass and an emitter bandpass of 535 nm (Chroma Technology, Brattleboro, Vt.). [$Ca^{2+}$], measurements were performed on individual GFP-positive cells at excitation wavelengths of 340 nm and 380 nm, and an emission wavelength of 510 nm. Prior to data acquisition, background fluorescence (areas without cells) was measured and automatically subtracted from subsequent measurements. Agonists were diluted in HEPES buffered saline and solution changes accomplished by rapidly aspirating the buffer and replacing it with HEPES buffered saline containing the specific agonist. Fura-2 fluorescence signals (340 nm, 380 nm and the 340/380 ratio) originating from individual GFP-positive cells were continuously monitored at a sampling frequency of 25 Hz and collected using a software package from Photon Technology International (Felix™). Conversion of the 340 nm/380 nm ratio value into $[Ca^{2+}]_i$ was estimated by comparing the cellular fluorescence ratio with ratios acquired using Fura-2 (free acid) in buffers containing known $Ca^{2+}$ concentrations. $[Ca^{2+}]_i$ was then calculated as described by Grynkiewicz, et al (Grynkiewicz, G, et al, J Biol Chem, 260: pp3440–3450, 1985). All assays were performed in assay buffers containing 1 mM EGTA to exclude measurement of calcium influx.

Figure 4A:
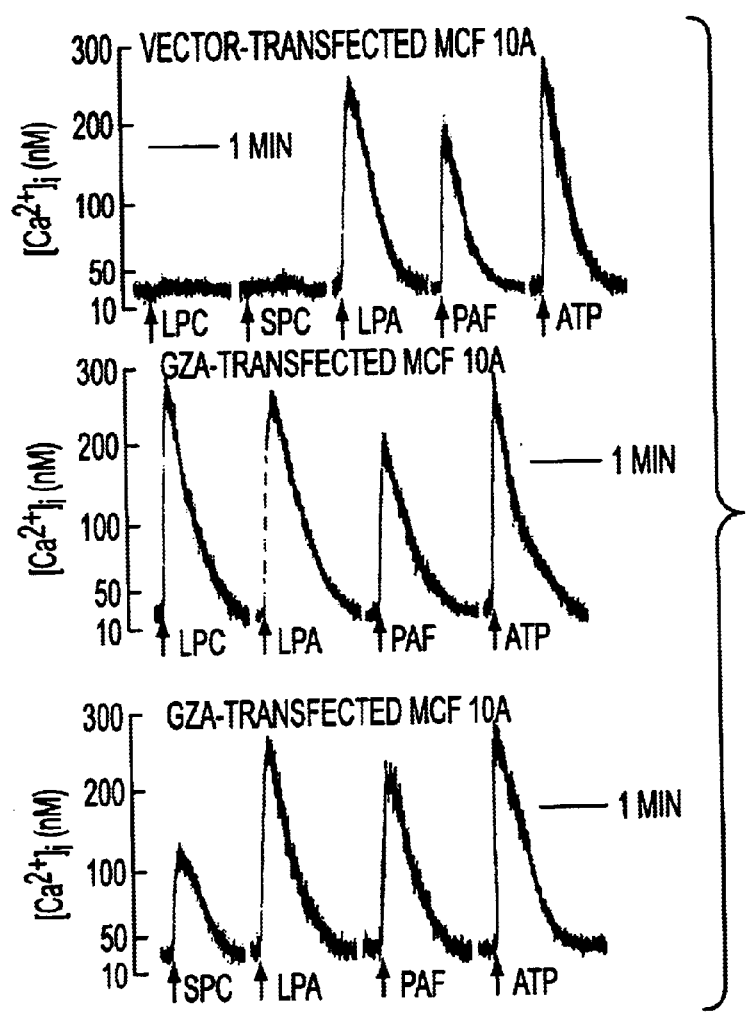
FIGS. 4A–F show that LPC and SPC induce transient $[Ca^2+]$, increases in G2A transfected MCF 10A cells. (A, upper panel) calcium responses of pEXV3 GFP transfected MCF 10A cells to 16:0 LPC (1 μM), SPC (1 μM), LPA (1 μM), PAF (0.1 μM) and ATP (20 μM). (A, middle panel) calcium responses of pEXV3 G2A.GFP transfected MCF 10A cells to 16:0 LPC (1 μM), LPA (1 μM), PAF (0.1 μM) and ATP (20 μM). (A, lower panel) calcium responses of pEXV3 G2A.GFP transfected MCF 10A cells to SPC (1 μM), LPA (1 μM), PAF (0.1 μM) and ATP (20 μM). (B) 16:0 LPC and SPC dose responses in pEXV3 G2A.GFP transfected MCF 10A cells. (C, upper panel) effect of PAF receptor inhibitor (BN52021) pretreatment on $[Ca^2+]$, increases induced by PAF (0.1 μM), 16:0 LPC (1 μM), LPA (1 μM) and ATP (20 μM). (C, lower panel) effect of BN52021 pretreatment on $[Ca^{2+}]$, increases induced by PAF (0.1 μM), SPC (1 μM), LPA (1 μM) and ATP (20 μM). (D, upper panel) pretreatment of pEXV3 G2A.GFP transfected MCF 10A cells with 16:0 LPC (1 μM) (upper panel) or SPC (1.0 μM) (lower panel) induces desensitisation to subsequent stimulation with 16:0 LPC or SPC (1 μM). (E) pretreatment of pEXV3 G2A.GFP transfected MCF 10A cells with PTX (100 ng/ml, 16 hours) inhibits $[Ca^{2+}]$, increases induced by 16:0 LPC (1 μH) (upper panel), SPC (1 μM) (lower panel), and LPA (1 μM) (both panels). (F) pretreatment of pEXV3 G2A.GFP transfected MCF 10A cells with PMA (0.1 mM, 5 minutes) inhibits $[Ca^{2+}]_i$ increases induced by 16:0 LPC (1 μM) (upper panel), SPC (1 μM) (lower panel), and LPA (1 μM) (both panels).
Figure 4B:
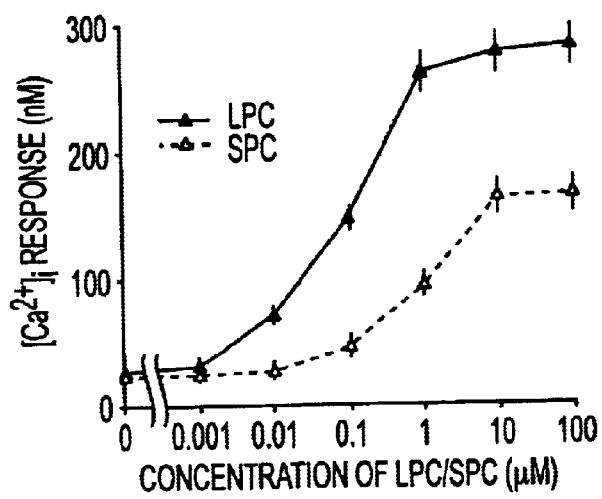

Example 10
Lysophosphatidylcholine And Sphingosylphosphorylcholine Induce Transient Increases In Intracellular Calcium Concentration In G2A Transfected Cells To address whether G2A is a lysophospholipid receptor, we examined signalling events in cells ectopically expressing G2A as functional correlates of receptor activation. The immortalised human breast epithelial cell line, MCF 10A, was chosen for studies as they do not express endogenous G2A or OGR-1, and do not respond to SPC with a transient elevation of intracellular calcium concentration $[Ca^{2+}]_i$ (Yan Xu, et al, Nature Cell Biology, 2: pp261–267, 2000). $[Ca^{2+}]_i$ measurements were performed in MCF 10A cells transfected with plasmids encoding green fluorescent protein (GFP) tagged G2A (pEXV3 G2A.GFP) (Kabarowski, J H S, et al, PNAS, 97: pp12109–12114, 2000) or GFP as described (Yan Xu and Derek S. Damron, Methods in Molecular Medicine, 39: Ovarian Cancer: Methods and Protocols, pp611–619, 2000). Neither parental or pEXV3 GFP transfected cells responded to SPC or LPC (up to 10 μM) (FIG. 4A, upper panel). However, in G2A.GFP transfected cells, LPC (0.1 μM) induced a transient increase in $[Ca^{2+}]_i$ (FIG. 4A, middle panel). Treatment of G2A.GFP transfected cells with SPC (0.1 μM) also induced a transient increase in $[Ca^{2+}]$, albeit to a lesser extent (FIG. 4A, lower panel), suggesting that G2A may bind LPC with a higher affinity. Dose-dependent increases in $[Ca^{2+}]_i$ were observed in G2A.GFP transfected cells at concentrations of LPC between 0.001 μM and 100 μM, with an $EC_{50}$ of approximately 0.1 μM (FIG. 4B). Similarly, dose-dependent responses of G2A.GFP transfected cells to SPC were observed, with an $EC_{50}$ of approximately 0.4 μM (FIG. 4B). Both GFP transfected and G2A.GFP transfected cells responded to lysophosphatidyc acid (LPA) (1 μM), PAF (0.1 μM), and ATP (20 μM) with transient elevations of $[Ca^{2+}]_i$. Responses to these agonists were not affected by G2A.GFP expression (FIG. 4A, middle and lower panels).

Figure 4C:
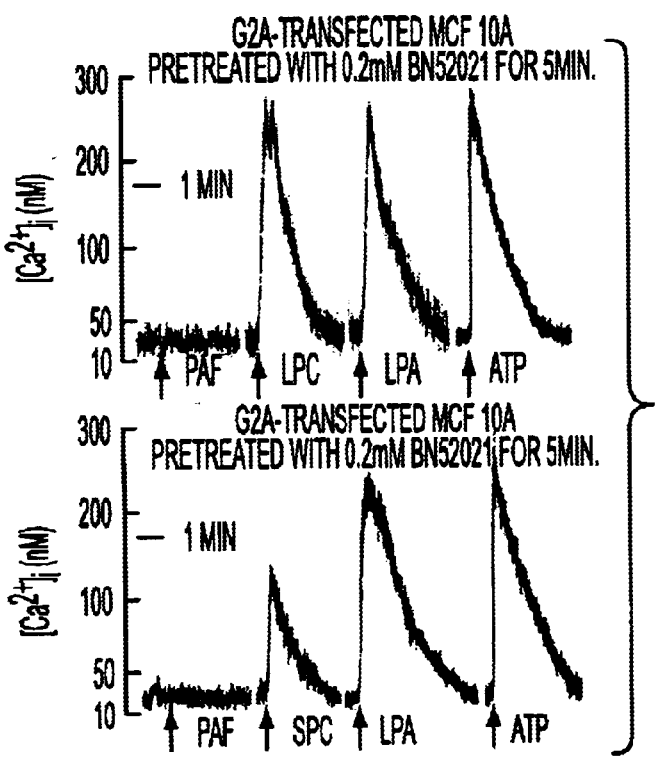
Figure 4D:
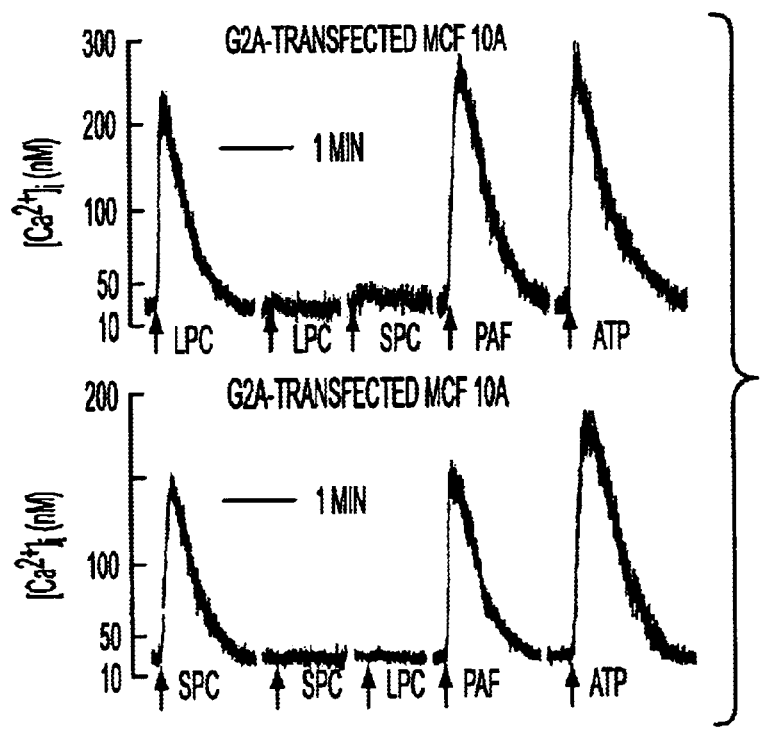

The partial sensitivity of LPC-induced effects to PAF receptor antagonists such as BN 52021 suggests that some effects of LPC may be mediated by the PAF receptor (Huang, Y H, et al, Clin Exp Immunol, 116: pp326–331, 1999) (Ogita, T, et al, American J Physiol, 272: ppH17–24, 1997) (Hirayama, T, et al, Hypertension Res, 21: pp137–145, 1998) (Huang, Y H, et al, Clin & Exp Immunol, 116: pp326–331, 1999). Pretreatment of G2A.GFP-transfected MCF 10A cells with BN 52021 (200 μM, Biomol) completely blocked the increase in $[Ca^{2+}]_i$ induced by PAF, but not that induced by LPC (1 μM), SPC (1 μM), LPA (1 μM), or ATP (20 μM) (FIG. 4C). Therefore, increases in $[Ca^{2+}]_i$ induced by LPC and SPC are mediated by G2A and do not involve action of these lysophospholipids via PAF receptors.

Concomitantly with activation of downstream signalling pathways, ligand stimulation of GPCRs elicits their desensitisation and internalisation. LPC (1 μM) or SPC (10 μM) pretreatment (5 minutes) of G2A.GFP-transfected MCF 10A cells induced homologous and heterologous desensitisation to subsequent stimulation with LPC or SPC (1 μM), providing further evidence for a cognate receptor/ligand relationship.

Figure 4E:
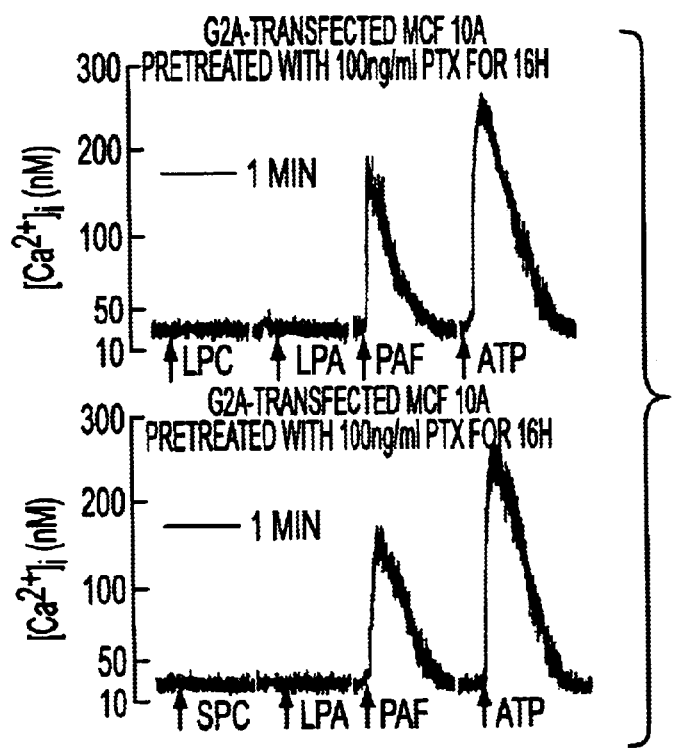
Figure 4F:
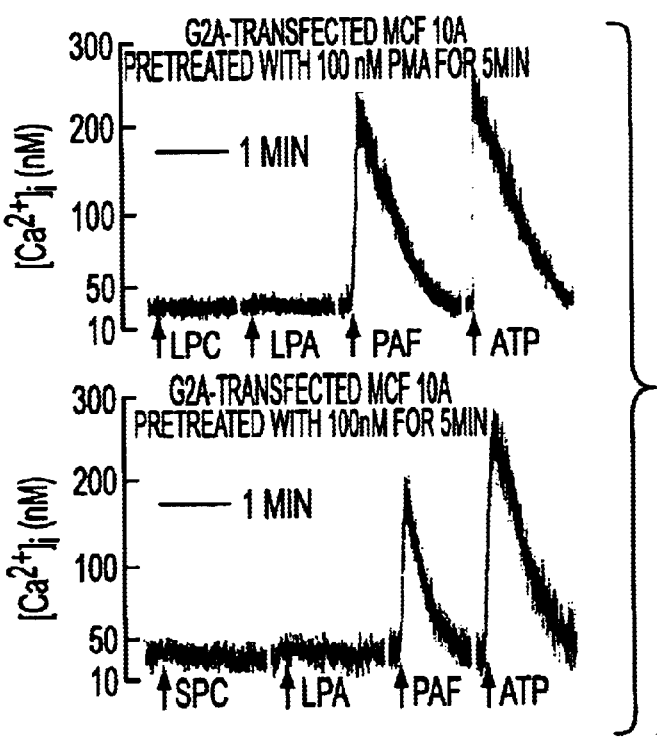

Heterotrimeric G proteins of the Gαi and Gαq class are involved in the propagation of signals from GPCRs leading to $[Ca^{2+}]_i$ elevation (Meyer zu Heringdorf, et al, Eur J Pharmacol, 354: pp113–122, 1998) (Xu, Y, et al, Nature Cell Biology, 2: pp261–267, 2000). To determine whether Gαi is involved in the elevation of $[Ca^{2+}]_i$ induced by LPC and SPC, G2A.GFP-transfected MCF 10A cells were pretreated for 16 hours with Pertussis Toxin (PTX, 100 ng/ml), an inhibitor of Gαi. PTX inhibited transient increases in $[Ca^{2+}]_i$ induced by LPA (1 μM), LPC (0.1 μM-5 μM) and SPC (1 μM-5 μM), but not those induced by PAF (0.1 μM) or ATP (20 μM) (FIG. 4E). These data indicate that LPC and SPC-induced transient increases in $[Ca^{2+}]_i$ are mediated through the activation of a Gαi family G protein.

Pretreatment of G2A.GFP-transfected MCF 10A cells with Phorbol 12-myristate 13-acetate (PMA, 100 nM, 5 minutes), an activator of PKC, abolished the transient increases in $[Ca^{2+}]_i$ induced by LPA, LPC and SPC (up to 10 μM), but did not affect those induced by PAF (0.1 μM and ATP (20 μM) (FIG. 4E). This indicates that PKC affects LPC signalling pathways by inducing G2A desensitisation and/or inhibition of Gαi. Several putative consensus PKC phosphorylation sites in G2A are located in the third intracellular loop and carboxy terminus, regions known to interact with G proteins (Iismaa, T P and Shine, J G, Curr Opin Cell Biol, 4: pp195–202, 1992). Thus, PKC mediated phosphorylation and receptor desensitisation may be responsible for the inhibitory effect of PMA.

Example 11
Activation of ERK MAP Kinase Via Ligand In G2A Expressing CHO Cells

Figure 7:
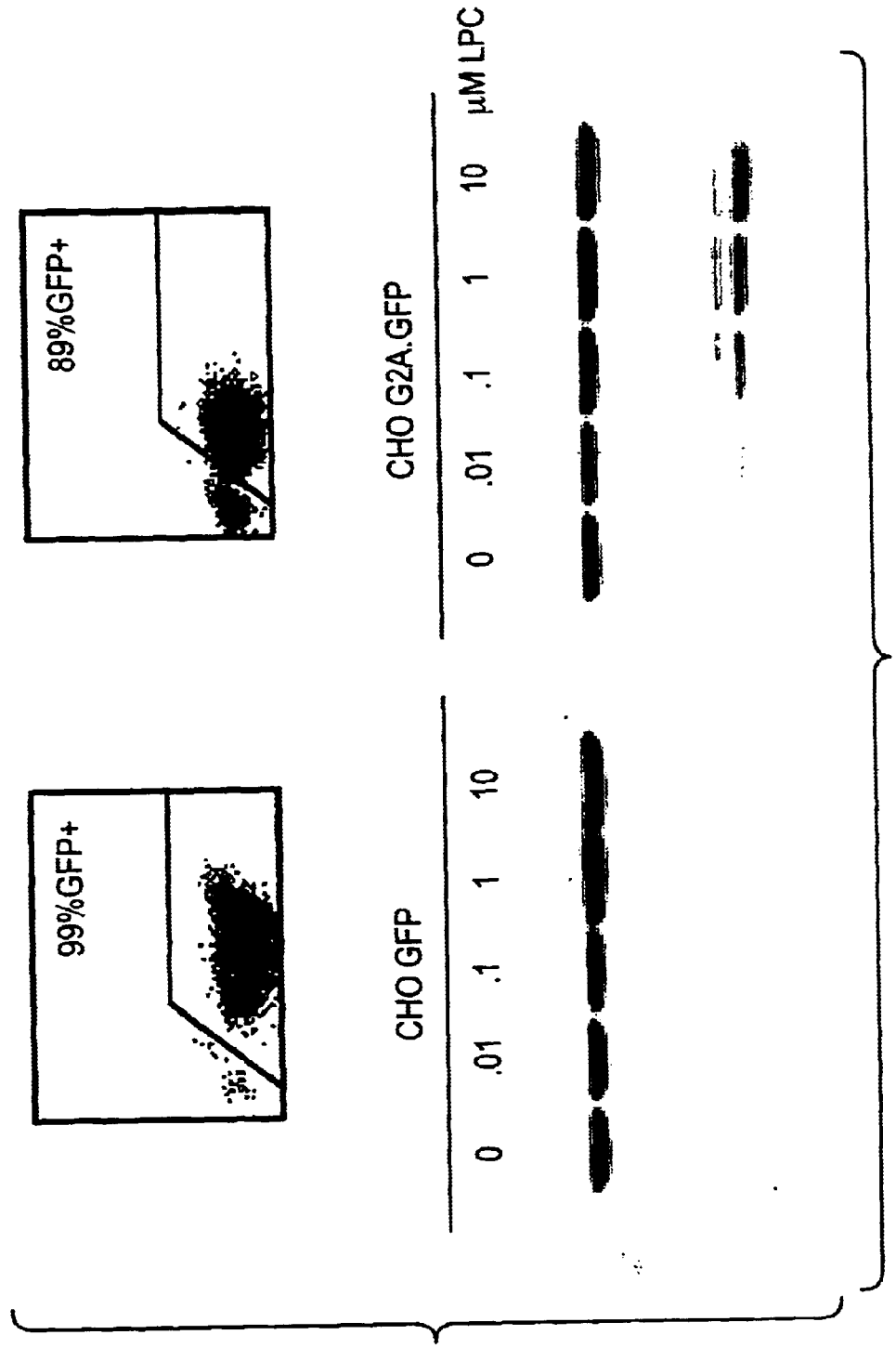
FIG. 7 shows that LPC activates ERK MAP kinase in G2A expressing CHO cells.

Further exploration of the cellular response to LPC was undertaken in Chinese hamster ovary (CHO) cells. Stable lines of G2A expressing CHO cells were derived by infection with retroviruses encoding G2A.GFP (MSCV G2A.GFP). We examined ERK MAP kinase activity in control CHO GFP and CHO G2A.GFP cells in response to varying doses of LPC (0.01 μM to 10 μM). While serum starved CHO GFP cells did not respond to LPC treatment, dose-dependent increases in ERK MAP kinase activity were induced by LPC in CHO G2A.GFP cells (FIG. 7).

ERK MAP kinase assay
CHO GFP or CHO G2A.GFP cells were serum starved for 18 hours prior to treatment with LPC for 10 minutes at 37° C. Western blotting was performed to detect activated p44/42 ERK MAP kinase using a specific phospho-ERK antibody (Santa Cruz Biotechnology,).

Figure 6:
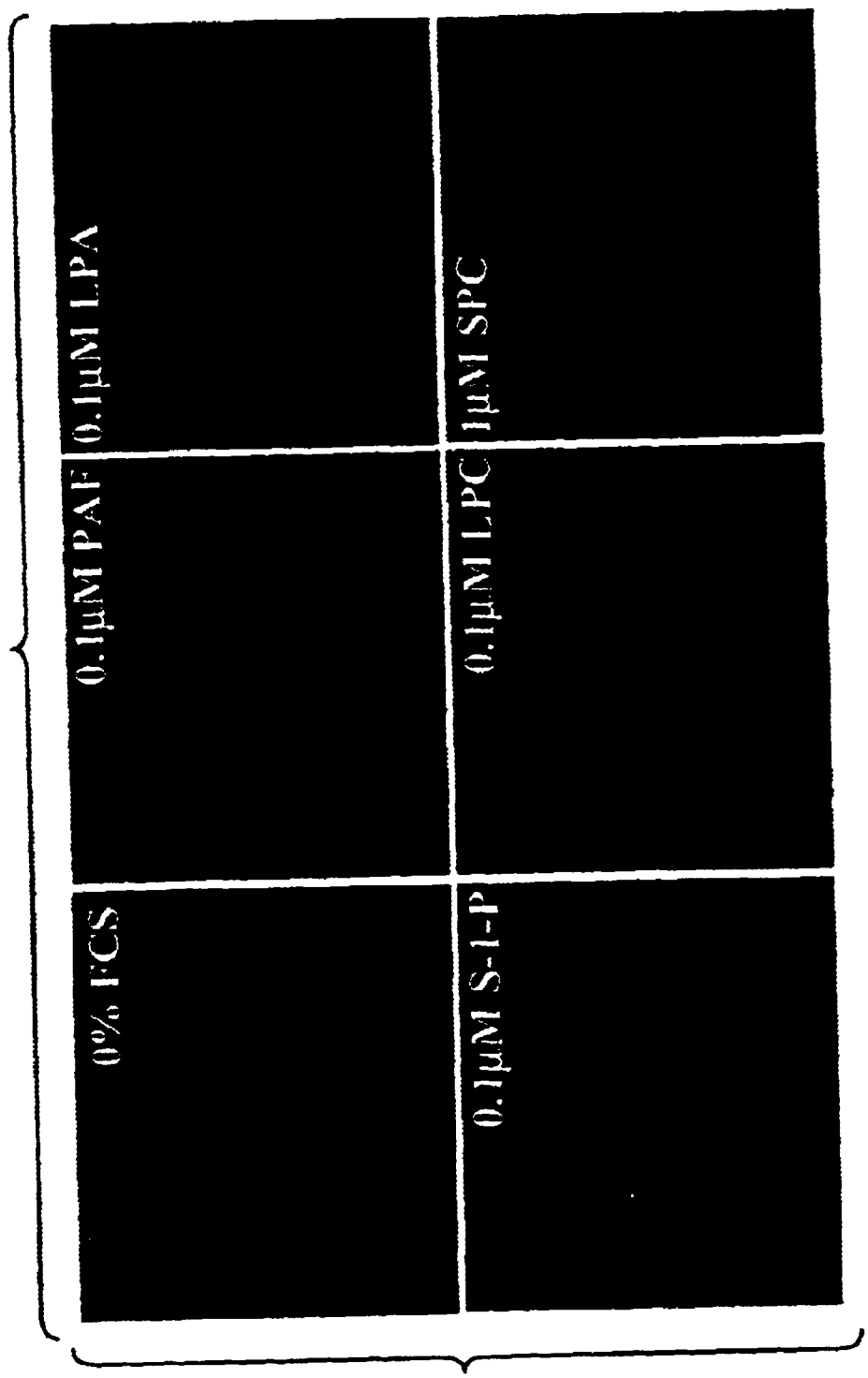
FIG. 6 shows the internalisation of G2A.GFP induced by LPC. HEK 293 cells expressing the G2A.GFP fusion receptor were treated with the indicated agonists for 2 hours. Results are representative of 3 independent experiments and the indicated responses were observed in >90% of cells.

Example 12
Ligand Induced Internalisation of G2A.GFP Fusion Protein
Agonist dependent receptor internalisation is a feature of GPCRs. G2A.GFP expressing HEK 293 cells (HEK 293 G2A.GFP) were generated by infection with amphotropic MSCV G2A.GFP retroviruses. In serum starved HEK 293 G2A.GFP cells, G2A.GFP is expressed predominantly on the plasma membrane. LPC (0.1 µM), as well as SPC (1 µM), induced internalisation of G2A.GFP in over 90% of cells (FIG. 6). Neither LPA, S-1-P or PAF induced G2A internalisation, which is consistent with LPC acting as a specific ligand for G2A. Treatment of HEK 293 G2A.GFP cells with SPC at low concentrations (0.1 µM) induced receptor internalisation in fewer cells (<50%). Together with the lower SPC-induced calcium responses (FIG. 4), this suggests that G2A may bind this lysophospholipid with low affinity.

Internalisation

HEK 293 G2A.GFP cells were seeded onto glass coverslips and subsequently serum starved for 16–24 hours prior to treatment with lipids. Two hours following lipid treatment, coverslips were washed with cold PBS and fixed with PBS/4% paraformaldehyde. Subcellular localisation of G2A.GFP was visualised under a confocal fluorescence microscope with a 60× oil immersion lens.

Example 13
Labelling G2A Ligands To Assess Binding To G2A

Figure 5A:
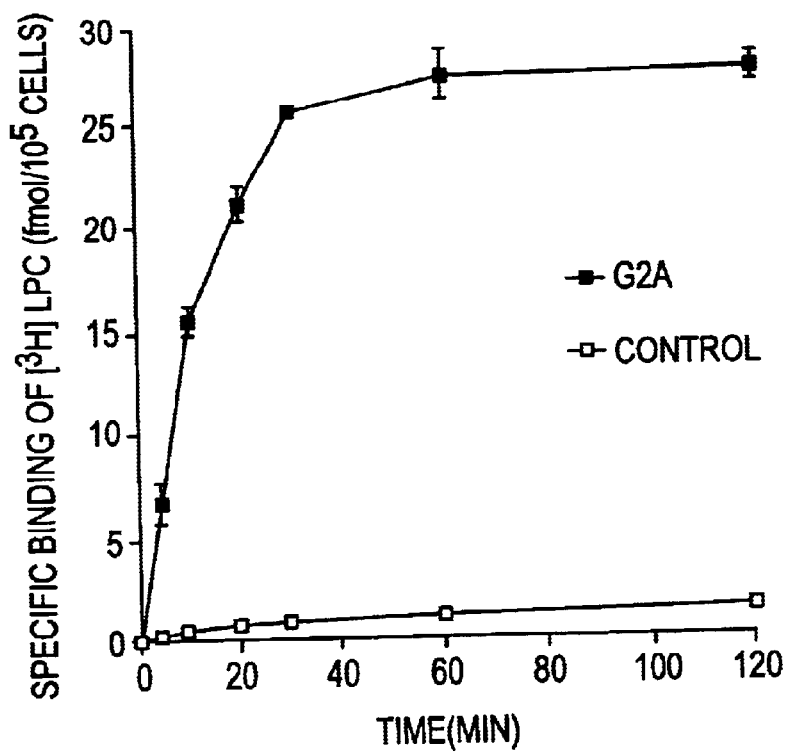
FIGS. 5A–5F show binding of 16:0 LPC and SPC to G2A. (A and B) time dependence of specific [$^3$H] LPC and [$^3$H] SPC binding. Cell homogenates from control HEK 293 GFP or HEK 293 G2A.GFP cells were incubated with [$^3$H] 16:0 LPC (1 nM) or [$^3$H] SPC (1 nM) for the indicated times. Specific binding is presented. (C and D) saturation isotherms of specific binding of [$^3$H] LPC or [$^3$H] SPC to HEK 293 GFP or HEK 293 G2A.GFP cells. Cell homogenates were incubated with the indicated concentrations of [$^3$H] 16:0 LPC or [$^3$H] SPC in the presence or absence of unlabelled LPC or SPC (100-fold excess) and specific binding was measured. Inset graphs show Scatchard analyses of [$^3$H] 16:0 LPC and [$^3$H] SPC binding to HEK 293 cell homogenate. (E and F) structural specificity of binding of [$^3$H] 16:0 LPC and [$^3$H] SPC to G2A. HEK 293 G2A.GFP cells were incubated with [$^3$H] 16:0 LPC (1 nM) or [$^3$H] SPC (1 nM) in the presence or absence of unlabelled lipids (100 nM). Total binding is presented. All binding experiments were performed in triplicate. Data are means ±SD representing 3 independent experiments. * p<0.05;  p<0.01; * p<0.001, compared to control (Student's t test).
Figure 5B:
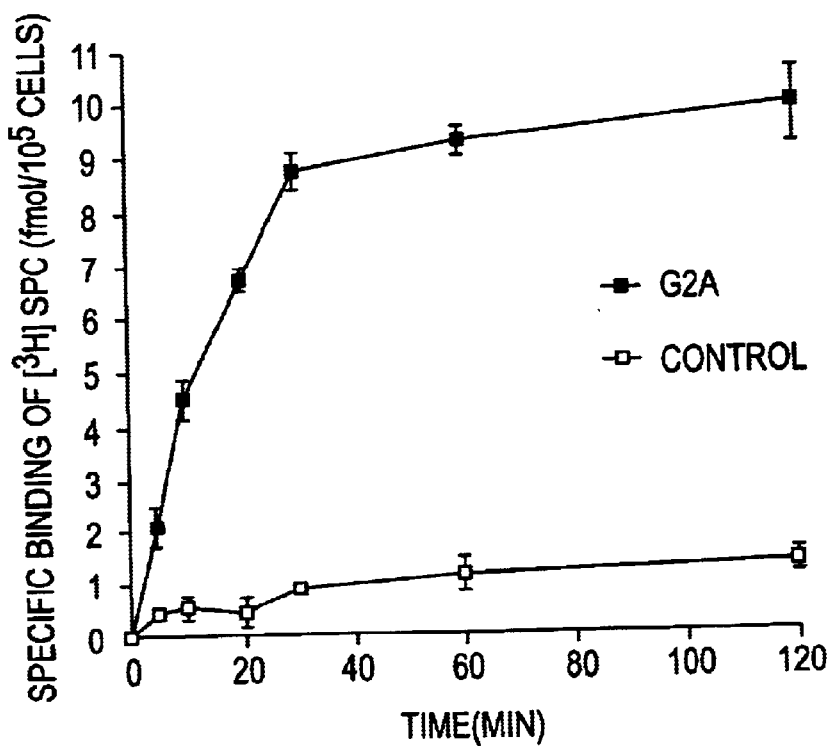
Figure 5C:
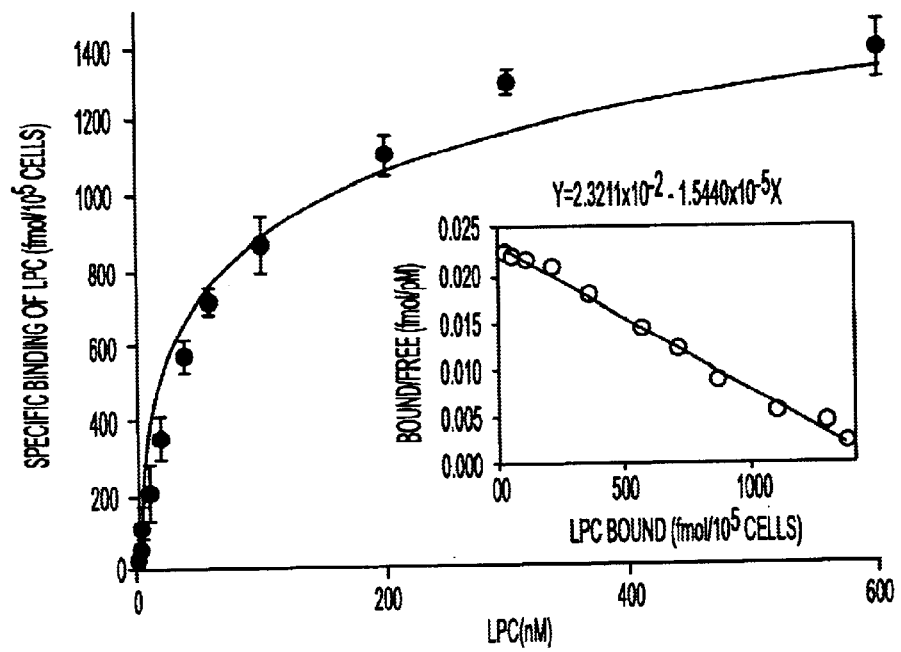
Figure 5D:
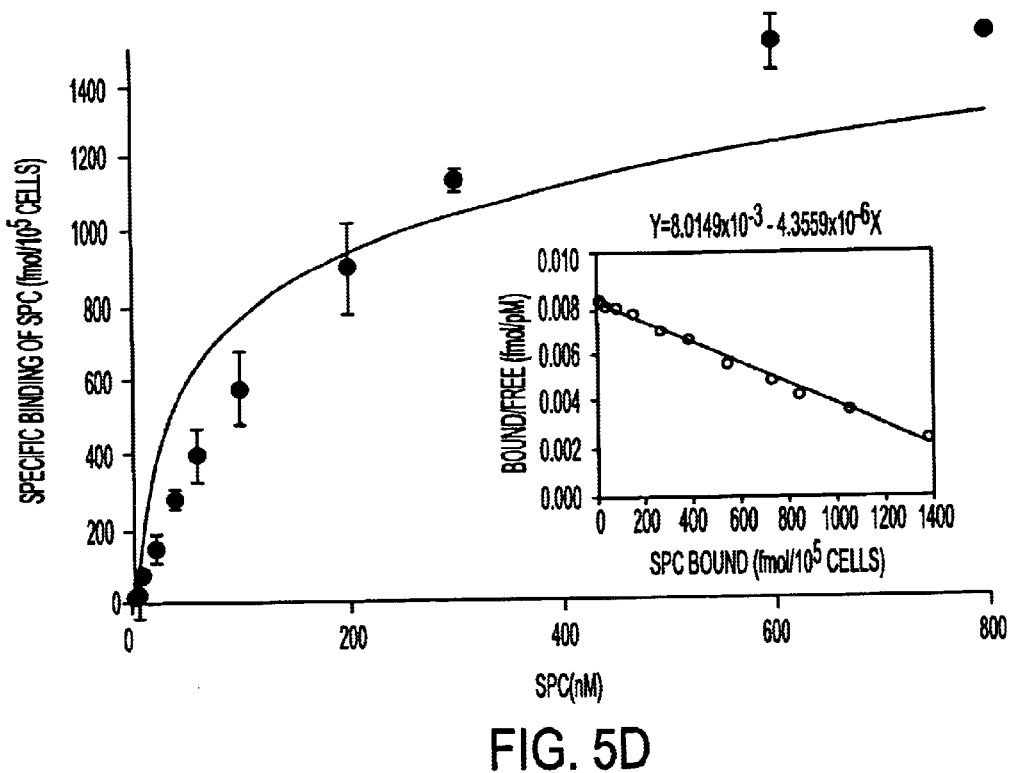
Figure 5E:
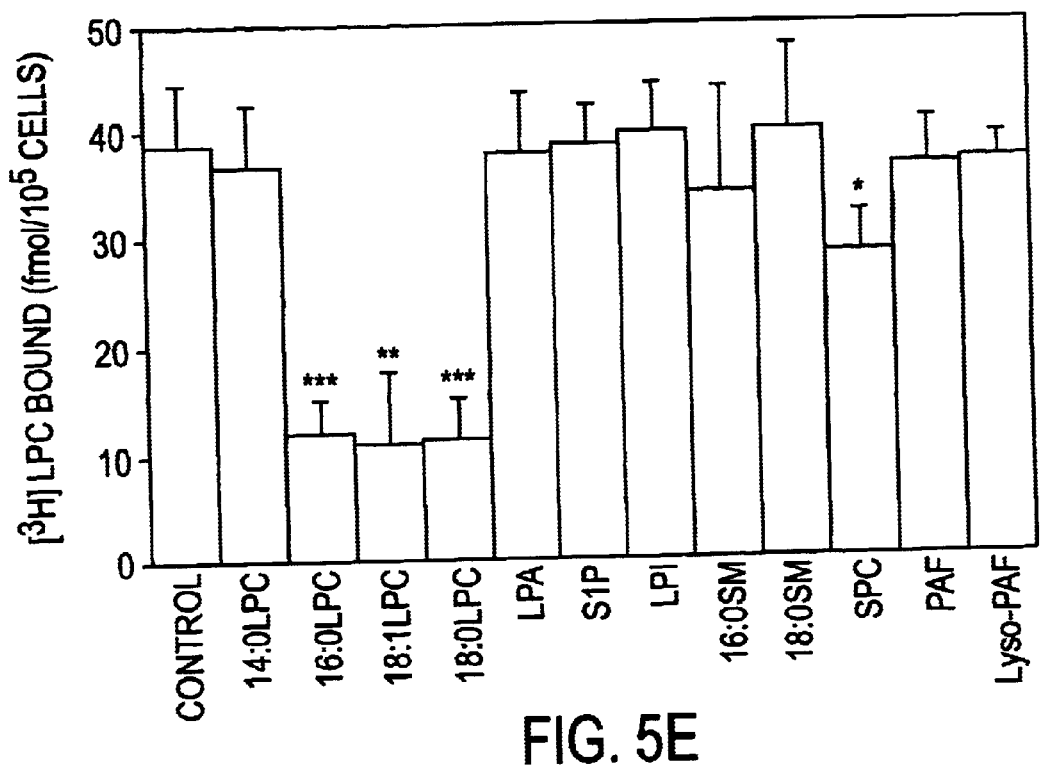
Figure 5F:
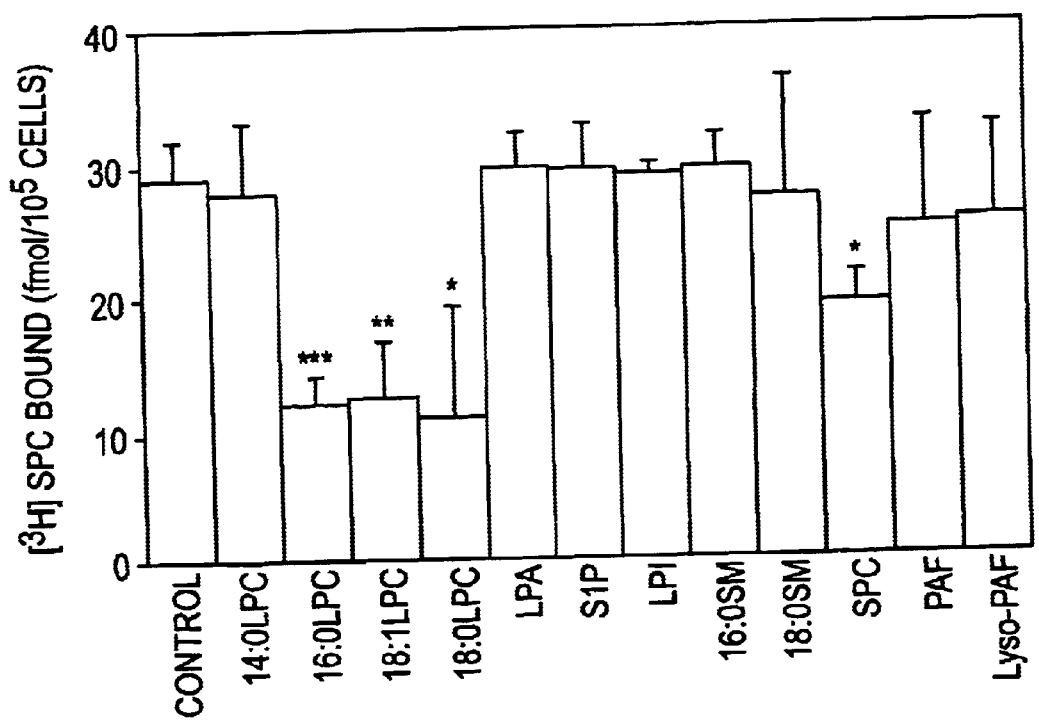

To characterise the binding of LPC and SPC to G2A, we performed radioligand binding assays as described previously (Xu, Y, e al, Nature Cell Biology, 2: pp261–267, 2000). [$^3$H] 16:0 LPC and [$^3$H] SPC bound to cell homogenates from G2A expressing HEK 293 cells in a time-dependent manner and reached equilibrium after 60 minutes incubation at 4° C. (FIGS. 5A and B). HEK 293 cells displayed low background binding of [$^3$H] LPC and [$^3$H] SPC. Binding of [$^3$H] LPC and [$^3$H] SPC was greatly increased in HEK 293 cells expressing G2A (FIGS. 5C and D). LPC and SPC bindings were saturable and Scatchard analysis indicated a dissociation constant ($K_d$) of 65 nM for LPC and 229 nM for SPC. The maximum binding capacities for LPC and SPC were approximately 1,503 fmole/$10^5$ cells and 1,840 fmole/$10^5$ cells respectively. Competition analyses revealed that only SPC and various LPC species, but not 14:0 LPC, LPA, S-1-P, lysophosphatidylinositol (LPI), sphingomyelin (SM), PAF or lyso-PAF, competed for binding (FIGS. 5E and F).

Binding assay HEK 293 GFP or HEK 293 G2A.GFP cells were serum starved for 20 hours and subsequently collected in PBS/EDTA. Pelleted cells were stored at −80° C. until use. Frozen cells ($10^6$ cells/ml) were homogenized in "binding buffer" containing 20 mM Tris-HCl pH 7.5, 100 mM NaCl, 15 mM NaF, 0.2 mM PMSF, 1 mM MgCl$_2$ and 4 mg/ml fatty acid-free BSA in a tight-fit glass Dounce homogeniser. Assays were performed in 96-well plates in triplicate with 100 µl cell homogenate (equivalent to $10^5$ cells/well). Varying amounts of [$^3$H] 16:0 LPC or [$^3$H] SPC were added to cell homogenates in 50 µl of binding buffer in the presence or absence of cold 16:0 LPC or SPC, or other competitors. Plates were incubated at 4° C. for 2 hours, or for the indicated times. Cell-bound [$^3$H] LPC or [$^3$H] SPC was collected onto a filter (Printed Filtermat A, Wallac, Gaithersburg, Md.) using an automated cell harvester (HARVESTER 96, Tomtec, Orange, Conn.). A pause wash programme (five cycle washes) was used. Filters were presoaked in 1% polyethyleneimine (Sigma) to prevent nonspecific binding, dried, sealed in bags (Sample Bag, Wallac) with 4.5 ml Betaplate "Scint" scintillation cocktail (Wallac), and counted in a 1450 Microbeta Trilux Liquid Scintillation and Luminescence Counter (Wallac). Specific binding was calculated by subtraction of nonspecific binding (binding detected in the presence of 100-fold excess unlabelled lipid) from total binding.

Different LPC species may have different affinities for G2A (FIGS. 5E and F); 14:0 LPC is not able to compete [$^3$H] 16:0 LPC binding, while 16:0 LPC, 18:0 LPC and 18:1 LPC are potent competitors. G2A also binds SPC with low affinity. While it is not unusual for a GPCR to bind two or more structurally related ligands with different affinities (Horuk, R, Trends in Pharmacological Sciences, 15: pp159–165, 1994) (Communi, D, et al, Cell Signal, 12: pp351–360, 2000), the physiological relevance of this promiscuity remains to be defined. Nevertheless, both distinct and overlapping expression of members of this GPCR sub-family together with shared ligand specificity (An, S, et al, FEBS Letters, 375: pp121–124, 1995) (Xu, Y, et al, Nature Cell Biology, 2: pp261–267, 2000) suggests that they may perform both redundant as well as unique biological roles. Our collective knowledge thus far suggests that each lysophospholipid (PC and SPC) may bind multiple GPCRs (G2A, OGR-1, GPR4), which have both distinct and overlapping tissue distributions (Xu, Y, et al, Nature Cell biology, 2: pp261–267, 2000).

Example 14
Creation of An Animal Model for Examining G2A
Generation of G2A-Deficient Mice As disclosed herein we generated G2A-deficient (G2A−/−) mice by homologous recombination to determine its role in lymphocyte development and function. Young G2A−/− mice appear normal and exhibit no discernible histological abnormalities of their lymphoid tissues. However, with age, they develop progressive secondary lymphoid organ enlargement associated with an abnormal polyclonal expansion of lymphocytes which dramatically disrupts their normal architecture. Finally, older G2A−/− mice (>1 year of age) succumb to an autoimmune syndrome whose late onset distinguishes it from phenotypically similar syndromes arising in mice with targeted disruptions of genes encoding other regulators of TCR signaling (Bachmaier, K., et al., 2000, Nature 403:211–216.; Chiang et al., 2000, Nature 403:216–220; Jacobson et al., 1995, Immunity 3:509–519; Tivol et al., 1995, Immunity 3:541–547). T cells from young G2A−/− mice display enhanced in vitro proliferative responses to TCR crosslinking and co-stimulation. These observations demonstrate that although G2A is not essential for normal T and B cell development, it plays an important homeostatic role in controlling peripheral lymphocyte numbers by regulating the threshold of TCR-dependent activation and proliferation.

Experimental Procedures

The G2A knock-out targeting vector was constructed from a 14 Kb Not I fragment of genomic DNA isolated from a 129-Sv mouse genomic library using G2A cDNA as a probe. A 3.6 Kb BstXI—HpaI fragment containing exon 2 derived coding sequences for the entire C-terminus and all intracellular and extracellular loops of G2A was replaced by a 4.5 Kb fragment encoding promoterless IRES-LacZ sequences and a 1.5 Kb PGK1—Neo resistance cassette flanked by Plox. The vector can be linearized with Not I and contains 5 Kb of 5' flanking sequence homology and 3 Kb of 3' flanking sequence homology. A 1 Kb HpaI-NotI fragment immediately downstream of the 3' sequence homology was used as the external probe for Southern blot hybridization to check for homologous recombination.

The targeting vector was electroporated into 129SvJ ES cells (Genomes System). Southern blot analysis of 150 Neomycin-resistant colonies yielded four positive clones. ES cells from these individual positive clones were injected into blastocysts harvested from C57BL/6 mice (UCLA Transgenic Facility). Chimeric males from two independent ES cell clones were crossed with BABB/C females. Germ line transmission of the G2A mutant allele was detected by southern blot analysis of tail DNA from F1 offsprings. G2A homozygous (−/−) mice were generated by interbreeding heterozygous (+/−) mice. All animals were housed in the conventional animal facility at UCLA (Los Angeles, Calif.).

RNA and PCR Analysis

An RT-PCR method was used to measure the G2A RNA levels as previously described (Weng et al., 1998, Proceedings of the National Academy of Arts and Sciences 95:12334–12339). Briefly, RNA was isolated from either splenic T cells or BCR-ABL transformed Pre-B lymphocytes (Weng et al. 1998, Supra). First-strand cDNA was synthesized from 5 µg of total RNA using the Superscript preamplification system (GIBCO/BRL). Ten percent of the first strand cDNA synthesis product was subsequently used for PCR using G2A-specific primers P1 (TAGCGGTCGCAGGAAATGCAG) (SEQ ID NO: 6) and P2 (CAGGACTGGCTTGGGTCATT). (SEQ ID NO: 7) Glyceraldehyde 3-phosphate dehydrogenase (G3PDH) control amphimer set (CLONTECH) was included as a control to ensure equivalent template levels and quality of RNA. For PCR analysis of TCR and Ig rearrangement, genomic DNA was isolated from spleen and lymph nodes of old mice and 50 ng was used as templates for PCR amplification. Primers are as follows: D2 (GCACCTGTGGGGAAGAAACT) (SEQ ID NO: 8); J2.6 (TGAGAGCTGTCTCCTACTATCGAT) (SEQ ID NO: 9) for TCR rearrangement and DSF (AGGGATCCTTGTGAAGGGATCTACTACTGTG) (SEQ ID NO: 10); $J_{H4}$ (AAAGACCTGCAGAGGCCATCTTACC) (SEQ ID NO: 11) for Ig rearrangement. PCR analysis was performed as previously described (Kawamoto et al. 2000, Immunity 12:441–450) and amplified DNA products were electrophoresed on a 1.2% agarose gel.

Cell Surface Staining and Flow Cytometric Analysis

Single cell suspensions from lymph nodes, spleen, bone marrow, or thymus were depleted of red blood cells by hypotonic lysis and stained with combinations of the following antibodies from Pharmingen (San Diego, Calif.), unless otherwise stated: PE-conjugated anti-B220; FITC-conjugated anti-IgM; PE-conjugated anti-BP-1; PE-conjugated anti-CD43; PE-conjugated anti-CD19; Tri-color-conjugated anti-B220 (CalTag); FITC-conjugated anti-TCRαβ; FITC-conjugated anti-CD3; Biotin-conjugated anti-CD25Rα; FITC-conjugated anti-Thy-1.2;PE-conjugated anti-CD4; FITC-conjugated anti-CD8; PE-conjugated anti-CD44; FITC-conjugated anti-CD69; PE-conjugated anti-Ter119; PE-conjugated anti-Grl; FITC-conjugated anti-Mac1 (Boehringer Mannheim Corp.). Data was acquired on a FACScan (Becton Dickinson) and analyzed using CellQuest software. Live cells were gated based on forward and side scatter.

Histological and Immunohistochemical analysis

Tissue specimens were harvested and fixed with 10% formalin in phosphate-buffered saline (PBS) for one day and subsequently embedded in paraffin. 4 µm thick sections were stained with hematoxyhn and eostn as previously described (Gorelik and Flavell, 2000, Immunity 12:171–181). For immunohistochemical studies of immunoglobulin complex deposition, paraffin sections of kidney tissue were baked overnight at 60° C., deparaffinized with xylene, rehydrated, and pretreated with rat serum. The sections were subsequently stained with biotinylated rat antiserum against mouse Ig (Pharmingen), followed by incubation with streptavidin and biotinylated horseradish peroxidase complex (DAKO) according to the manufacturers instructions. Sections were developed with diaminobenzidine tetrahydrochloride (DAB) (Sigma) and counterstained with hematoxylin. ANAs were detected by indirect immunoflourescence on Hep-2 cells from IMMCO (Buffalo, N.Y.) according to the manufacturers instructions (Di Cristofano et al., 1999, Science 285:2122–2125).

For X-gal staining, mice were anesthetized with ketamine (1.5 mg/mouse) and subjected to total body perfusion with 4% paraformaldehyde in PBS. Tissues were harvested, equilibrated in 30% sucrose in PBS overnight at 4° C., and subsequently embedded in OTC medium (Tissue-Tek). Frozen sections were sliced with a cryostat and mounted on superfrost microscope slides (Fisher Scientific). Cryostat sections were post-fixed with 4% paraformaldehyde, stained with X-gal at 30° C. overnight and counterstained with neutral red. The X-gal reaction mixture comprises 1 mg/ml 4-chloro-5-bromo-3-indolyl-β-galactoside (X-gal), 4 mM potassium ferrocyanide, 4 mM potassium ferricyanide, 2 mM magnesium chloride in PBS.

In Vitro Proliferation Assays

Peripheral B or T cells from lymph nodes and spleen were isolated using the Mininacs magnetic bead system (Miltenyi Biotec, Inc., Auburn, Calif.) according to the manufacturers instructions. Briefly, single-cell suspensions were depleted of red blood cells by hypotonic lysis and macrophages by plastic adherence prior to incubation with anti-B220 microbeads. T or B cell-enriched populations were >90% pure by FACS analysis. B220$^+$ B cells or CD3$^+$ T cells were seeded into 96-well plates at 2.5×10$^5$ cell per well in RPMI with 10% heat-inactivated FCS. B220$^+$ B cells were incubated with various concentrations of goat anti-mouse IgM F(ab')$_2$ fragments Jackson ImmunoResearch Labs.) or LPS (Diffco). CD3$^{3+}$ T or total lymph node cells were cultured in the presence of various concentrations of ConA (Pharmacia) or plate-bound anti-CD3ε antibody (Pharmingen) with or without anti-CD28 antibody (Pharmingen). 1 µCi [$^3$H] Thymidine (NEN Life Science Products) was added into each well at the indicated time-points for 12 hours and [$^3$H] Thymidine incorporation was measured by scintillation counting as described previously (Miyazaki et al., 1997, The EMBO Journal 16:4217–4225).

For analysis of tyrosine phosphorylation, T cell stimulation was performed as previously described (Murphy et al., 1998, Molecular and Cellular Biology 18:4872–4882). Briefly, purified T cells were incubated with anti-CD3ε antibody (5 µg/ml) on ice for 20 minutes, washed, and subsequently incubated with goat anti-hamster IgG (5 µg/ml) (Jackson ImmunoResearch Labs.) on ice for a further 20 minutes. CD3/TCR complexes were crosslinked by shift to 37° C. for the indicated times. Following stimulation, T cells were washed once in ice-cold PBS and subsequently lysed in ice-cold Triton-X-100 buffer (50 mM Tris-HCl [pH 7.4], 150 mM NaCl, 1 mM EDTA, 1 mM sodium orthovanadate, 1 mM NaF, 1 mM PMSF, 1% Triton-X-100, 10 µg/ml aprotinin, 10 µg/ml leupeptin, and 10 µg/ml bestatin). Cleared lysates were run on 10–16% gradient SDS-polyacrylamide gels and proteins transferred onto nitrocellulose. Membranes were immunoblotted with 4G10 antiphosphotyrosine antibody (Upstate Biotechnology) followed by incubation with horseradish peroxidase conjugated goat anti-mouse secondary antibody (Bio-Rad). Signal was detected by enhanced chemiluminescence (ECL) following the manufacturers recommendation (Amersham).

Mixed Lymphocyte Reactions (MLRs)

Responder lymph node T cells were cultured at various ratios with stimulators (2500 rads irradiated splenic cells) from the same animal for syngeneic MLRs, or from C57BL/6 mice for allogenic MLRs. At the indicated time-points, proliferation was assessed by [³H] Thymidine incorporation during the last 12 hours of culture (Miyazaki et al., 1997, The EMBO Journal 16:4217–4225).

T cell-dependent and T cell-independent immune responses

To induce antibody responses to T cell-dependent antigen, mice were immunized intraperitoneally with 100 μg of DNP-KLH (Calbiochem) in incomplete Freund's adjuvant (GIBCO BRL, Gaithersburg, Md.), boosted on day 21 with 50 μg of DNP-KLH in PBS, and bled on days 14 and 28. For T cell-independent antibody responses, mice were immunized intraperitoneally with 10 μg of TNP-Ficoll (Biosearch Technology, Inc.) in incomplete Freund's adjuvant (GIBCO BRL, Gaithersburg, Md.) and bled seven days later. Serum immunoglobulins and DNP-specific or TNP-specific antibody titers were measured by enzyme-linked immunosorbent assay (ELISA) as described previously (Satterthwaite et al., 1998, Journal of Experimental Medicine 188:833–844).

Generation of G2A-deficient mice.

Figure 8A:
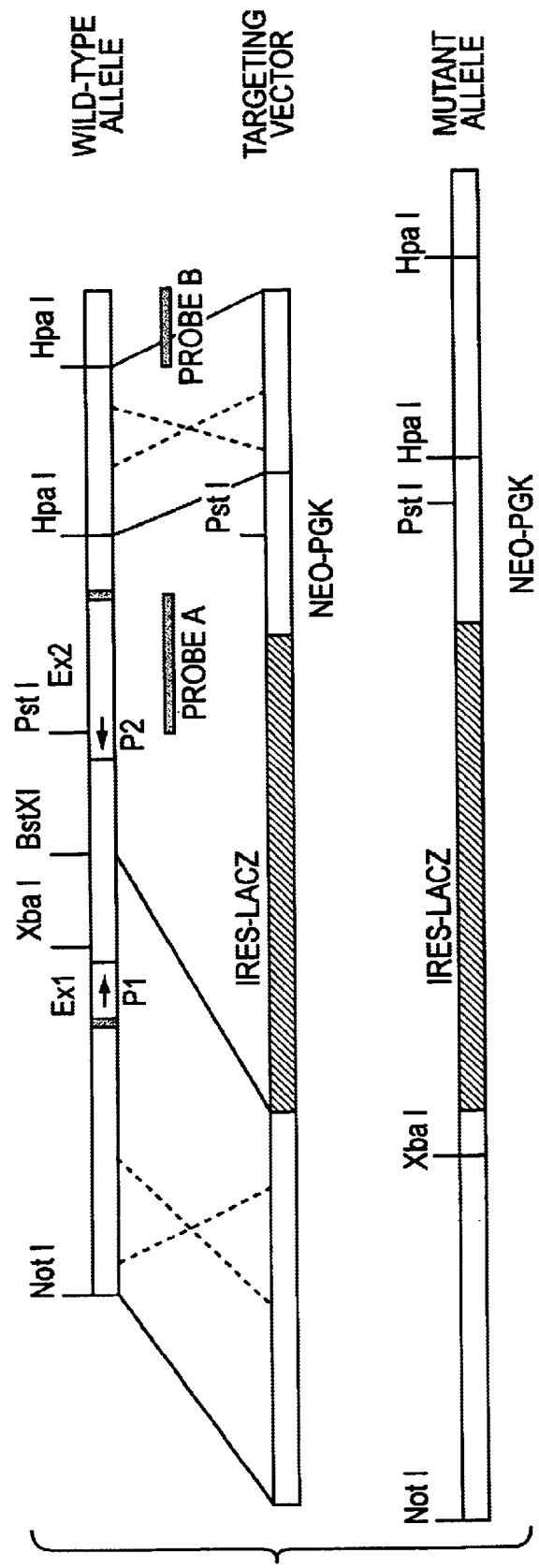

We used homologous recombination in 129SvJ embryonic stem (ES) cells to disrupt the G2A locus. A targeting vector was constructed by replacing the second exon of the G2A gene, which contains 98% of the total coding sequence, with IRES-β-galactosidase (LacZ) sequences driven by the endogenous G2A promoter and a Neomycin resistance gene driven by a cis-linked PGK promoter (FIG. 8A). Chimeric mice generated from targeted ES cells were bred with BALB/c mice. All phenotypic studies reported in this manuscript were conducted with mice backcrossed from $3^{rd}$ to $6^{th}$ generations onto the BALB/c background. Heterozygotes carrying the G2A null mutation were interbred, and offspring were genotyped by Southern blot analysis of tail DNA (FIG. 8B). Heterozygous (G2A+/–) and homozygous (G2A–/–) mutant mice are born with expected Mendelian frequencies. Young G2A–/– mice are healthy and appear indistinguishable from wild-type litermates. Southern blot analysis of genomic DNA using G2A cDNA as a probe demonstrates the successful deletion of the G2A gene at the DNA level (FIG. 8C). In addition, RT-PCR analysis of RNA from G2A–/– Pre-B and T cells failed to detect the expression of G2A mRNA, further confirming that G2A proteins cannot be made (FIG. 8D). These combined data demonstrate that this alteration of the G2A gene is a loss of expression mutation.

Examination of the expression pattern of murine G2A on multiple tissue mRNA blots revealed that the highest expression is in hemato-lymphoid tissues like spleen and thymus (Weng et al., 1998, Proceedings of the National Academy of Arts and Sciences 95:12334–12339). To further characterize the pattern of G2A expression in various murine tissues, we used the LACZ knock-in as a surrogate marker. X-gal staining and histological analysis of tissue sections derived from G2A+/– mice confirmed that G2A is expressed predominantly in lymphoid tissues like bone marrow, spleen and thymus. Interestingly, LACZ expressing cells are present at a low frequency in lymphoid organs of G2A+/– mice. This could be due to low detection limits of this method as T and B cells are known to contain a β-Gal-inhibitory activity (Elefanty et al., 1998, Proceedings of the National Academy of Arts and Sciences 95:11897–11902; Krall and Braun, 2000, New Biol 4:581–590; Schwarze et al., 1999, Science 285:1569–1572). However, it is also possible that G2A expression may be restricted to those lymphocytes engaged in specific processes of immunological function or development. We also observe expression of G2A in testis and kidney. In the kidney, G2A is expressed at the cortical-medullary junction, whereas in the testis G2A expression is largely confined to mature spermatids. We do not currently know what role, if any, G2A plays in these tissues.

Normal T and B cell development in G2A-deficient mice.

Compared to wild-type animals, G2A–/– mice grow and breed normally. Up to 8 weeks of age, G2A–/– mice display no gross abnormalities, although rarely an animal will have an enlarged superficial inguinal lymph node. Histological analyses of bone marrow, thymus, spleen, lymph nodes, Peyer's patch, kidney, testis, adrenal gland, liver, pancreas, small and large intestine, brain, heart, lung, skeletal muscle and skin from wild-type and G2A–/– mice revealed no morphologic differences.

Figures 9A, 9B:
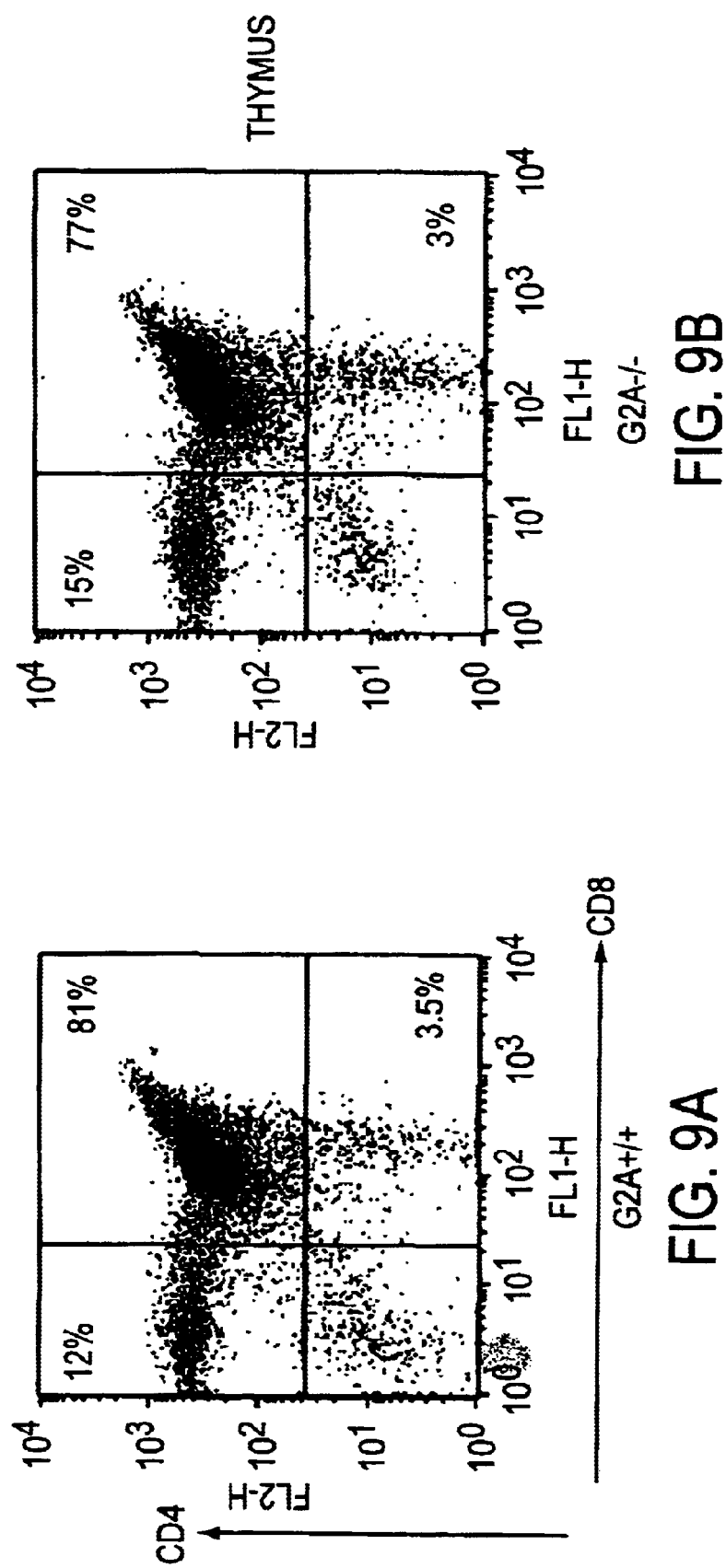
Figures 9E, 9F:
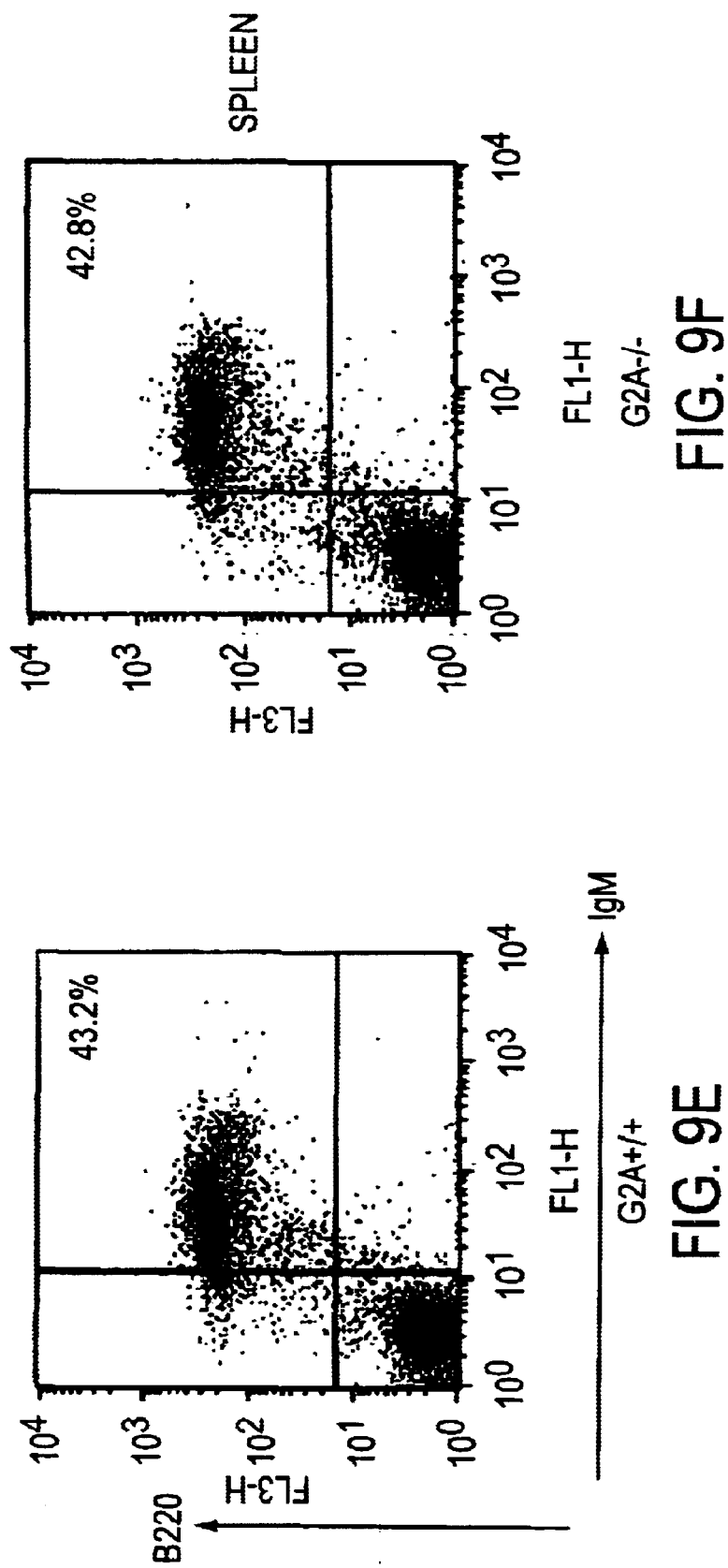

To determine the potential consequences of loss of G2A function in T and B lymphoid lineages, we examined the composition and distribution of cell surface markers in the bone marrow, thymus, spleen and lymph nodes of young (6 to 10 weeks of age) G2A–/– mice. Expression of TCRαβ, CD3, CD4, CD8, CD25Rα, Thy1.2, CD44, CD69, B220, IgM, IgD, BP-1, CD43, and CD19 was analyzed. T and B lymphoid compartments of wild-type and G2A–/– animals are indistinguishable by these criteria (FIG. 9). In addition, proliferative expansion and differentiation of G2A–/– T and B lymphoid precursors and their progeny in fetal thymic organ culture (Hashimoto et al., 2000, Journal of Immunology 164:1569–1575) and long-term Pre-B bone marrow culture (Whitlock and Witte, 1987, Methods in Enzymology 150:275–286) are indistinguishable from that of their wild-type counterparts. Normal development of G2A–/– T lymphoid subsets in fetal thymic organ cultures also suggests that migratory responses of thymic precursors and their progeny are not impaired in the absence of G2A.

Our previous observation that ectopic expression of G2A in heterologous cell-types delays cell-cycle progression through G2/M (Weng et al., 1998, Proceedings of the National Academy of Arts and Sciences 95:12334–12339) warranted examination of growth and apoptotic responses in G2A–/– lymphoid cells. Treatment of wild-type and G2A–/– B lymphoid and thymic T cells with various doses of ionizing radiation (IR), etoposide or dexamethasone in vitro induced apoptosis to the same extent and with similar kinetics as measured by FACS analysis of propidium iodide and anti-Annexin-V antibody stained cells. In addition, we found no significant differences in cell-cycle parameters or the rate and degree of apoptosis in wild-type versus G2A–/– T and B lymphoid cells following serum deprivation in vitro, or in vivo exposure of animals to varying doses of IR.

To assess the integrity of humoral immune responses in young adult G2A–/– mice (2–4 months old), we measured basal levels of serum immunoglobulin (Ig) production in unimmunized wild-type and G2A–/– mice. Comparable levels of different Ig isotypes (IgM, $IgG_1$, $IgG_{2a}$, $IgG_{2b}$, $IgG_3$, IgA) were observed, indicating that G2A–/– B lymphocytes are capable of isotype switching and a normal balance of Ig isotype production. We also measured the responses of wild-type and G2A–/– mice to immunization with T-cell dependent and T-cell independent antigens, DNP-KLH and TNP-Ficoll respectively (Satterthwaite et al., 1998, Journal of Experimental Medicine 188:833–844). Both wild-type and G2A–/– mice are able to mount comparable antibody responses to both of these antigenic challenges as determined by measurement of DNP-specific IgG1 and TNP-specific IgM. In addition, animals were challenged with infectious agents including *Bordetella pertussis* and Listeria (Harvill et al., 1999, Infect Immunol 67:6109–6118; Jensen et al., 1998, Infect Immunol 66:4143–4150). The rates of pathogen clearance were indistinguishable in wild-type and G2A–/– animals. Taken together, these observations indicate that a functional G2A gene product is not required for the development and immunological function of T and B lymphocytes in young adult mice.

Lymphoid expansion and disruption of lymph node architecture in older G2A-deficient mice.

Figure 10B:
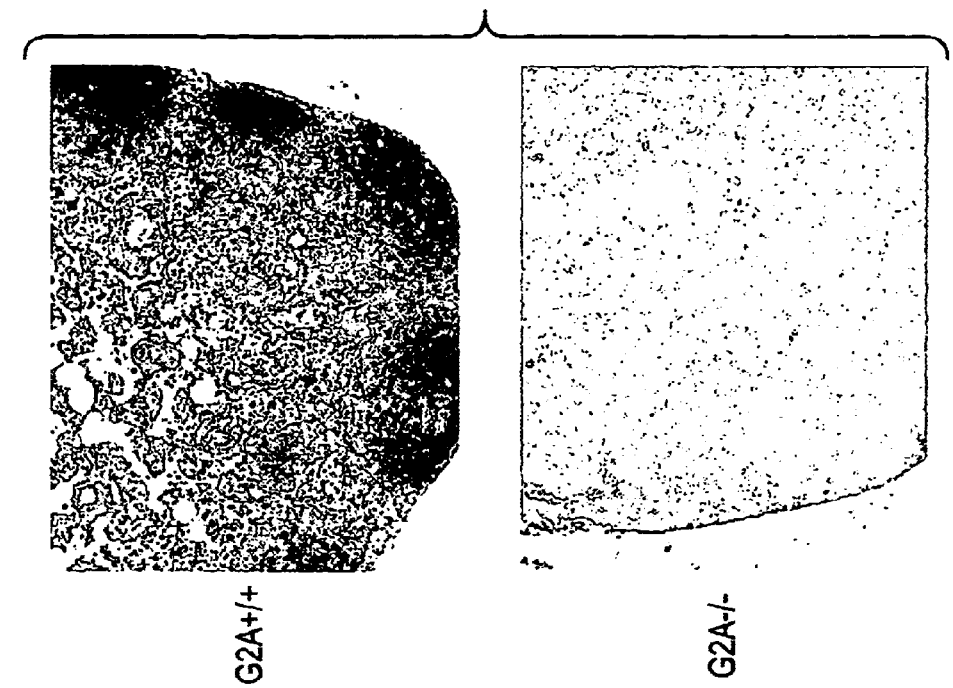
FIGS. 10A–C show enlargement of lymphoid organs and disruption of follicular architecture in older G2A-deficient mice. (A) peripheral lymph nodes and spleens of a typical 15 month-old G2A-/- mouse (right panel) and its wild-type littermate (left panel). (B) Hematoxylin and eosin stained sections of lymph nodes from wild-type (upper panel) and G2A-/- (lower panel) mice. (C) PCR analysis of TCR (left panel) and Ig (right panel) rearrangement. (Lane 1-2) G2A-/- spleens; (lane 3-5) G2A-/- lymph nodes; (lane 6) wild-type spleen; (lane 7) DNA size markers (GIBCO).
Figure 10A:
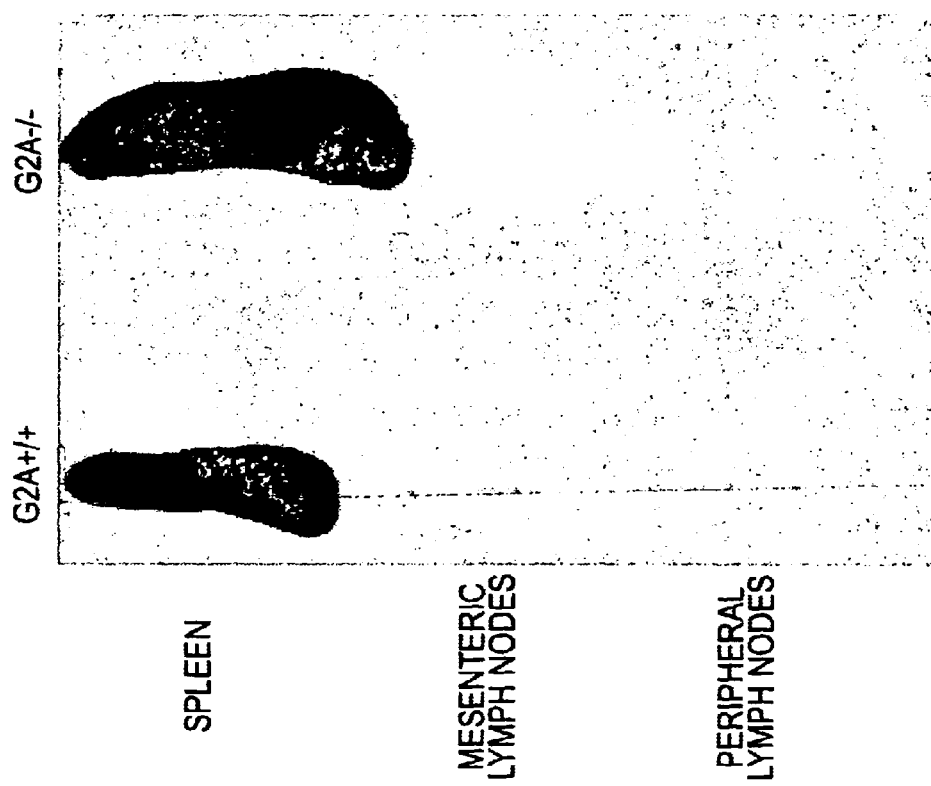
Figure 10C:
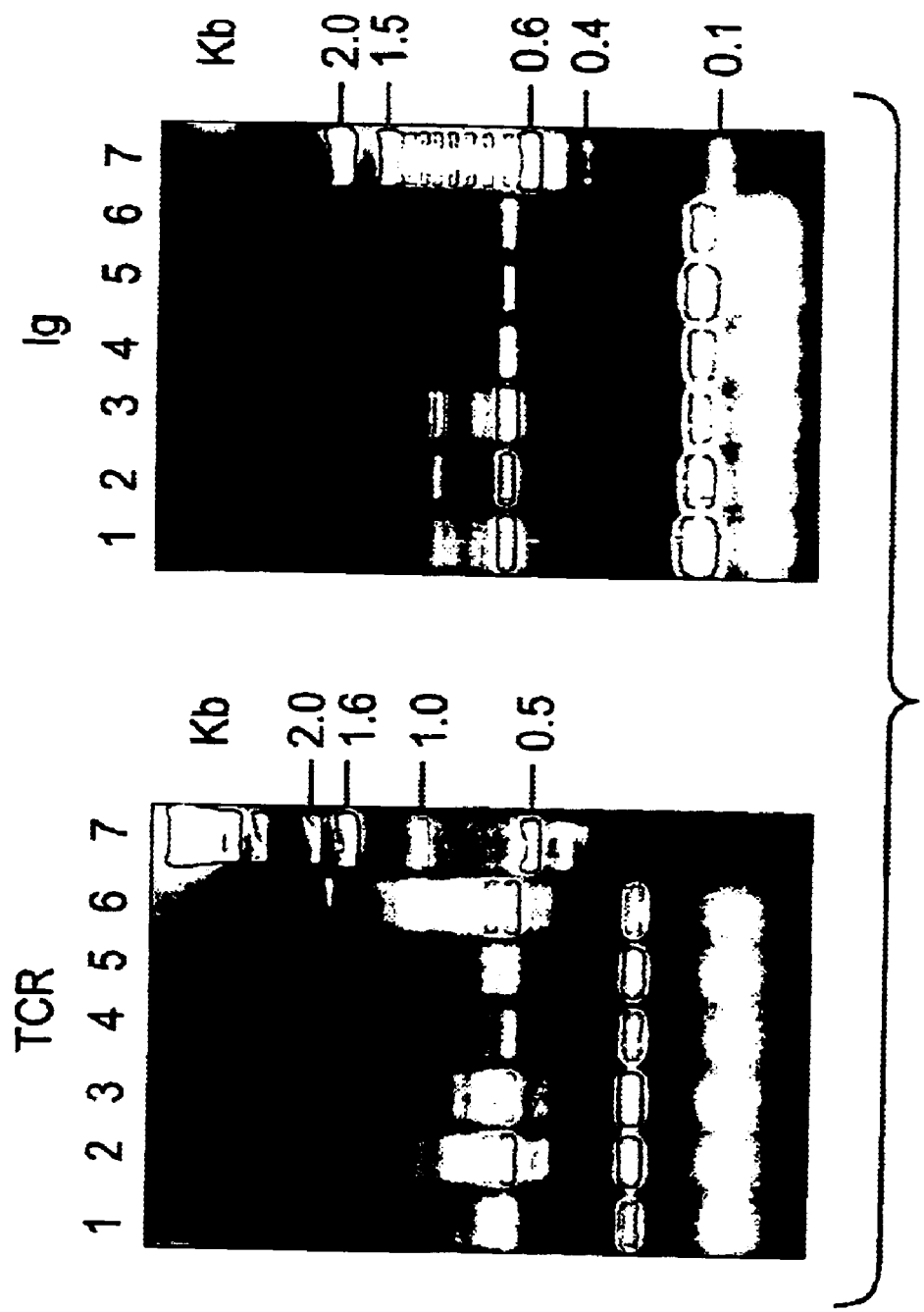

While young G2A-/- mice exhibit no discernible histological and cellular abnormalities of their lymphoid tissues, examination of older mice reveals progressive development of various anomalies which become more frequent and severe with age, indicative of a dysregulated immune system. Most prominent is a moderate enlargement of spleen and lymph nodes in G2A-/- mice greater than 6 months of age, while G2A-/- mice greater than 1 year of age exhibit gross enlargement of these secondary lymphoid organs (FIG. 10A). These changes were seen uniformly in G2A-/- mice examined from multiple litters. Thymi in wild-type and G2A-/- animals at these ages are not enlarged and indistinguishable. The lymphadenopathy is most prominent in the inguinal regions and is associated with increased numbers of both T and B lymphocytes, resulting in almost complete disruption of normal lymph node architecture FIG. 10B). This increase in lymphoid numbers does not appear to result from malignant expansion of a clonal nature (FIG. 10C) since PCR amplification of rearranged TCR and Ig junction and diversity regions (Kawamoto et al., 2000, Immunity 12:441–450) in G2A-/- mice (lane 1-5) revealed no evidence of clonality in comparison to wild-type spleen (lane 6).

Autoimmunity in older G2A-deficient mice.

Figure 11A:
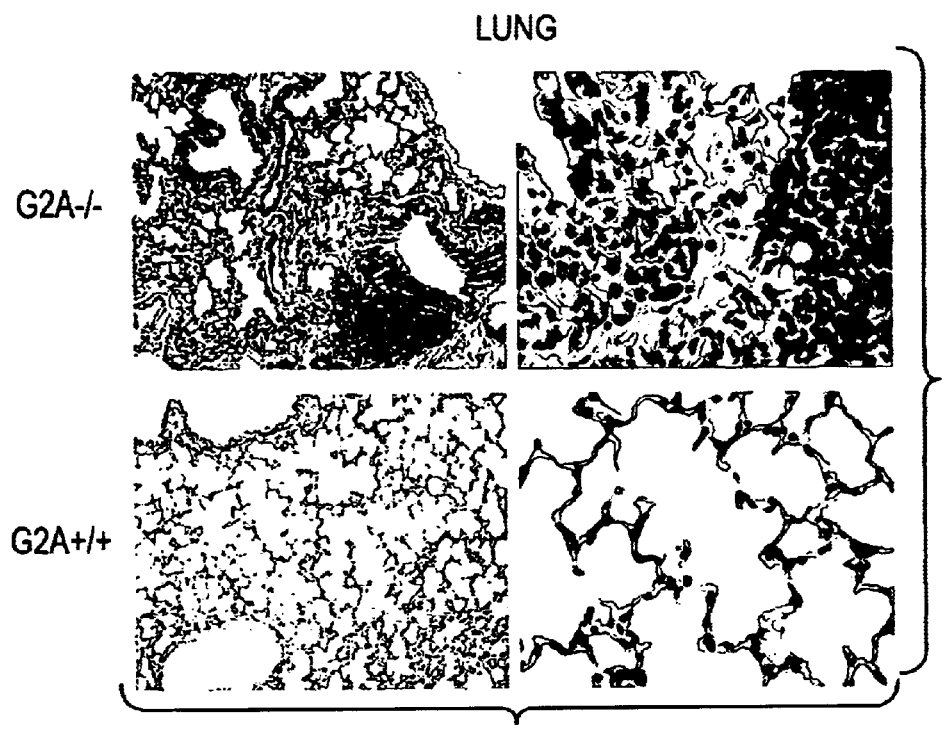
FIGS. 11A–B show a Photomicrograph of lung and liver sections from wild-type and G2A-/- mice stained with H & E. Histology of lung (A) and liver (B) tissues from a typical 15 month old wild-type mouse (lower panel) and a 15 month old G2A-/- mouse (upper panel) showing perivascular infiltration of mononuclear cells. (Right panels) 100x; (Left panels) 400x.
Figure 11B:
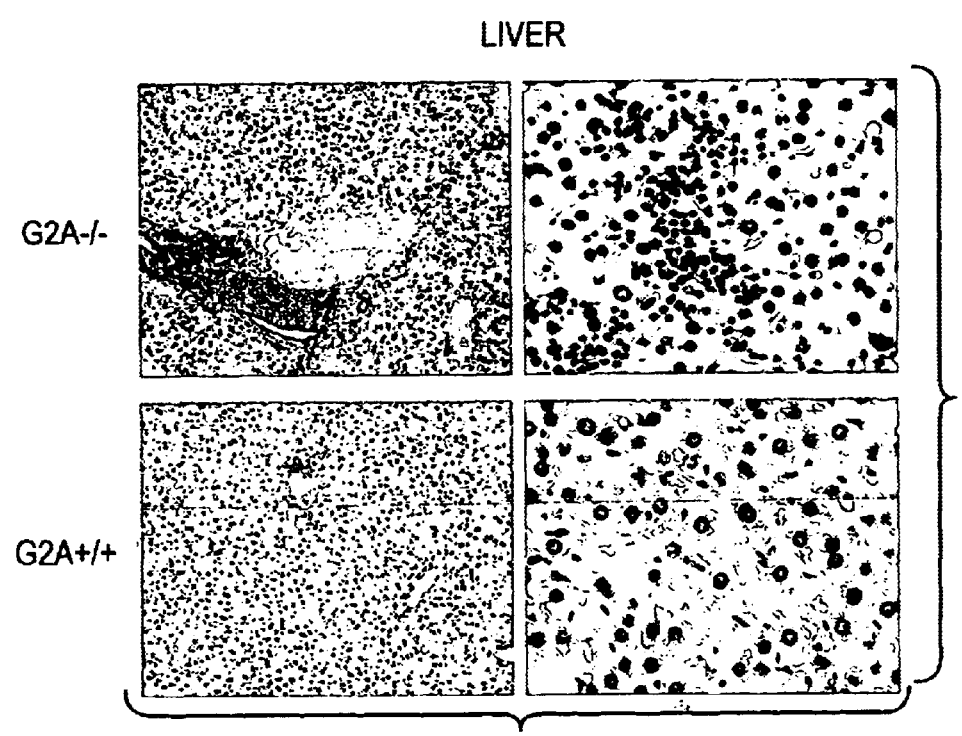

G2A-/- mice appear healthy until 15 to 16 months of age, when they begin showing signs of wasting. Wild-type litermates show no detectable signs of illness at this age. Histological examination of various tissues from these G2A-/- mice reveals heavy lymphocytic infiltration into various organs. Lungs of G2A-/- mice have prominent perivascular and interalveolar infiltration of mononuclear cells (FIG. 11A). Clusters of lymphocytes are present in the liver parenchyma of these G2A-/- animals (FIG. 11B).

Figures 2, 12A:
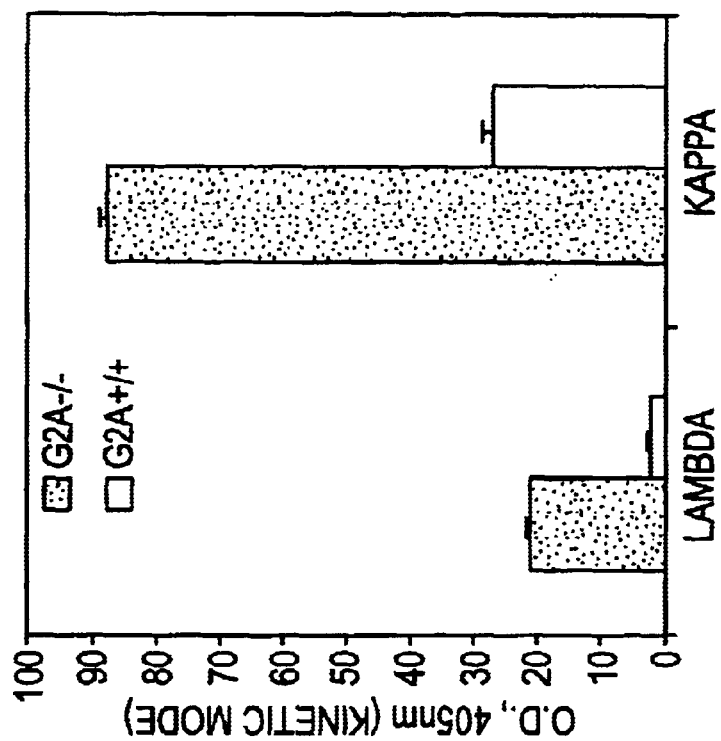
FIG. 2 shows a sequence alignment of murine (SEQ ID NO:2) and human (SEQ ID NO:4) G2As. The human and murine G2As share approximately 70% identity at the amino acid level.
FIGS. 12A–C show that older G2A-deficient mice develop an autoimmune syndrome. (A) Serum immunoglobulin levels in wild-type and G2A-/- mice. Increased immunoglobulin levels of IgG$_1$ and IgA (left panel) as well as elevated levels of both kappa and lambda light chains (right panel) in G2A−/− mice. (B) Paraffin sections of kidney tissue from wild-type (lower panels) and G2A−/− (upper panels) mice reveal glomerular immunoglobulin deposition. (left panels) 100×; (right panels) 400×. (C) Indirect immunoflourescence analysis of serum autoantibodies in wild-type and G2A−/− mice. Autoantibodies reacting against nuclear antigens are present in serum from G2A−/− mice (left panels, 1 and 2) but not in wild-type mice (right panels, 3 and 4).
Figures 1, 12A:
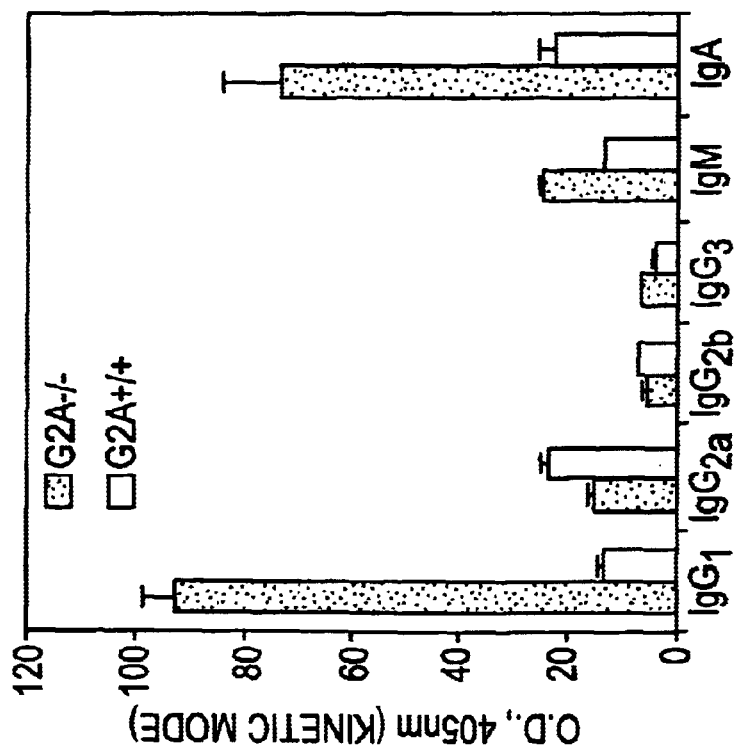
Figure 12B:
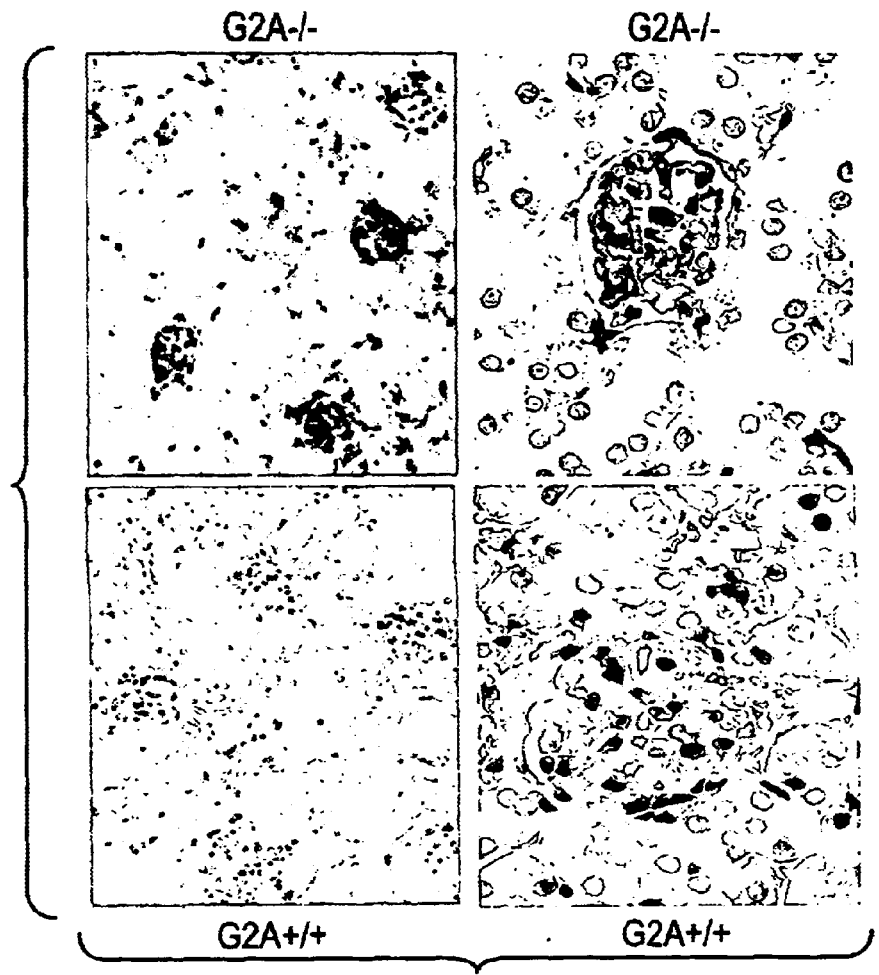
Figure 12C:
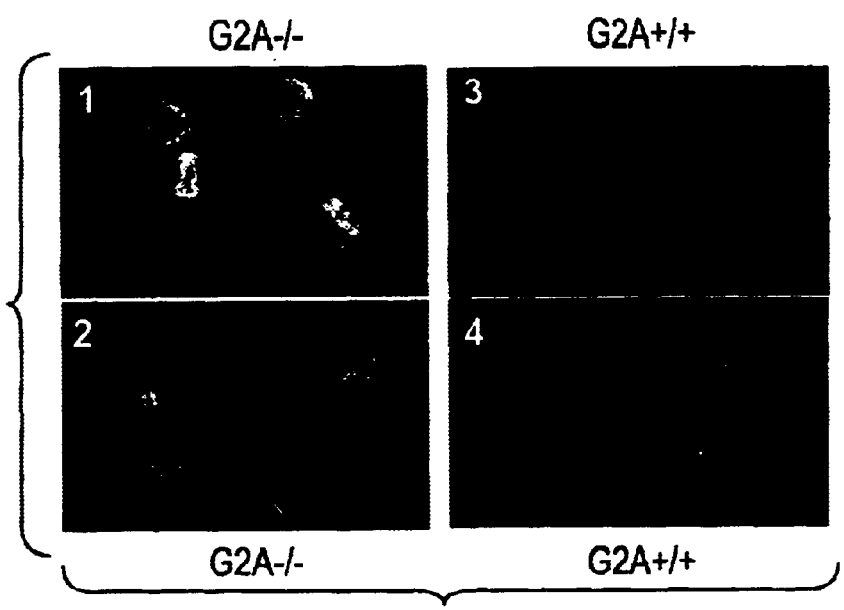

Affected mice also have increased immunoglobulin levels of different isotypes (IgG$_1$ and IgA) as well as elevated levels of both kappa and lambda light chains (FIG. 12A). Deposition of immunoglobulin complexes is detected in the glomeruli of older G2A-/- mice, whereas little deposition of IgG is detected in those of age-matched wild-type littermates (FIG. 12B). As one of the primary causes for deposition of immune complexes in the glomeruli is the presence of autoantibodies against nuclear antigens, we examined sera from wild-type and G2A-/- mice by indirect immunoflurescence on Hep-2 cells (Di Cristofano et al., 1999, Science 285, 2122–2125). Anti-nuclear autoantibodies (ANAs) showing speckled patterns and decorating mitotic figures are readily detectable in G2A-/- sera and absent in wild-type sera (FIG. 12C). Together with the emergence of lymphadenopathy in aging G2A-/- mice, these observations are consistent with the development of a late-onset non organ-specific autoimmune syndrome whose latency distinguishes it from other murine models of autoimmunity displaying otherwise similar pathological features (Bachmaier et al., 2000, Nature 403:211–216; Chiang et al., 2000, Nature 403:216–220; Hornquist et al., 1997, Journal of Immunology 158:1068–1077; Jacobson et al., 1995, Immunity 3:509–519; Tivol et al., 1995, Immunity 3:541–547).

G2A-deficient T cells exhibit enhanced proliferative responses to T cell receptor stimulation.

When considered together with the normal lymphoid development and immune function observed in young G2A-/- mice, the age-related development of lymphadenopathy and autoimmunity suggests a defect in normal regulatory mechanisms controlling the level or threshold of antigen receptor-dependent immunological activation. To address the question of whether the lymphoproliferative phenotype of older G2A-/- mice is associated with altered responses to antigen receptor stimulation, we tested young animals (6–10 weeks of age) prior to the development of any overt signs of histopathological abnormalities. G2A-/- peripheral T cells were stimulated in titro by plate-bound anti-CD3ε antibodies and proliferation measured by tritiated Thymidine ([$^3$H] Thymidine) incorporation. Compared to their wild-type equivalents, G2A-/- T cells exhibit enhanced proliferative responses to stimulation with anti-CD3ε antibodies across a range of concentrations (FIG. 13A). Importantly, this is not associated with abrogation of CD28 costimulation requirement for IL-2 production in G2A-/- T cells as levels of IL-2 are comparably low in supernatants of anti-CD36 antibody stimulated wild-type and G2A-/- cultures. Suboptimal concentrations of anti-CD36 antibodies (0.25–0.5 μg/ml) which barely induce a proliferative response in wild-type T cells nevertheless elicit a significant proliferative response in G2A-/- lymphocytes, suggesting lower TCR thresholds in the latter (FIG. 13A).

Figure 13B:
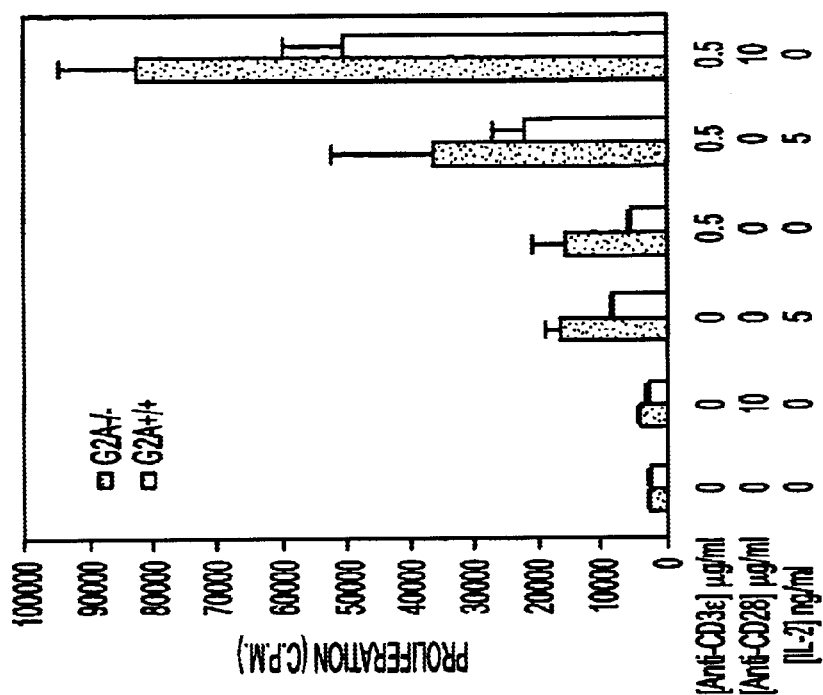
Figure 13A:
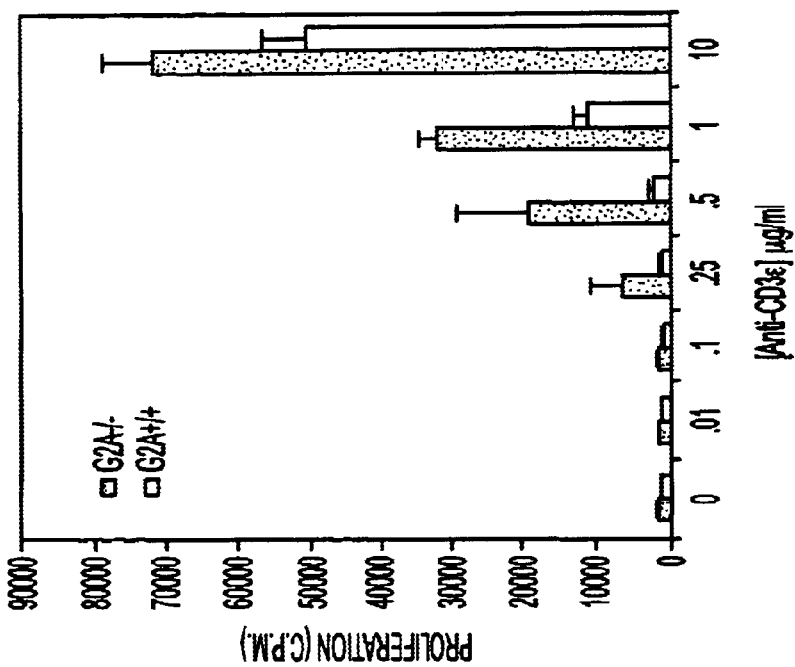
Figure 13D:
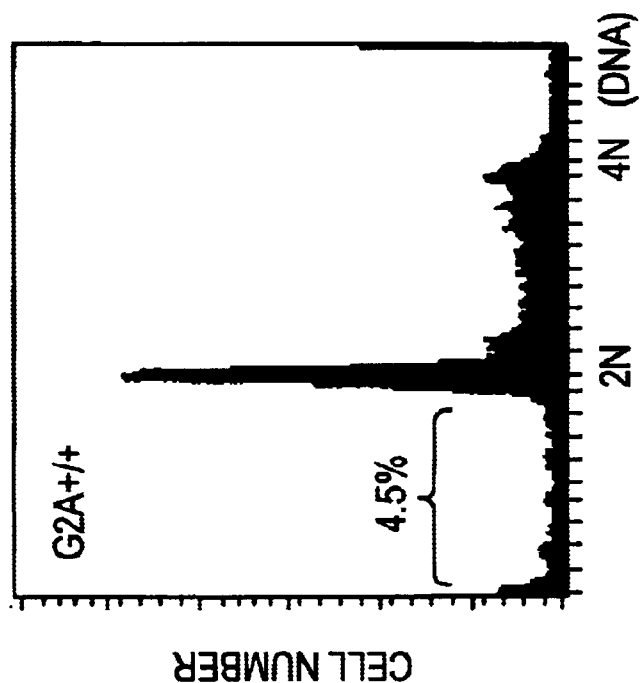
Figure 13C:
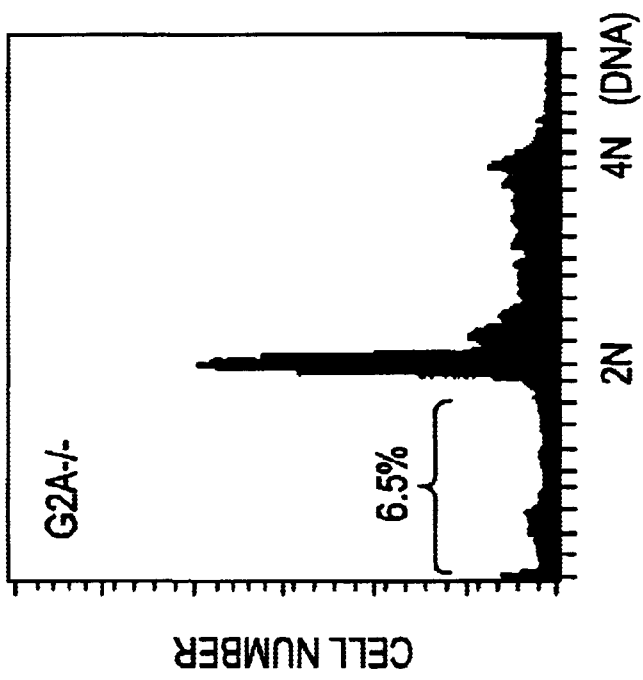

Costimulation of wild-type and G2A-/- T cells with anti-CD3s mAb plus anti-CD28 mAb, or anti-CD3εmAb plus IL-2, similarly induces greater proliferative responses in G2A-/- versus G2A+/+ lymphocytes, despite both being increased above that elicited by anti-CD36 antibody alone (FIG. 13B). Importantly, the rate and extent of apoptosis in stimulated cultures of wild-type and G2A-/- T lymphocytes are indistinguishable as measured by FACS analysis of propidium iodide stained cells, demonstrating that increased survival is not likely a major component of the hyperproliferative phenotype (FIGS. 13C, D).

We also analyzed antigen receptor-dependent proliferative responses of B cells in vitro (Satterthwaite et al., 1998, Journal of Experimental Medicine 188:833–844). Both wild-type and G2A-/- peripheral B cells displayed equivalent proliferative responses to surface IgM crosslinking as well as lipopolysaccharide (LPS) stimulation (FIGS. 13E, F), suggesting that either the primary action of G2A is in T cells rather than in B cells, or that loss of G2A function in B cells is compensated by one or more homologous GPCRs.

Figure 14B:
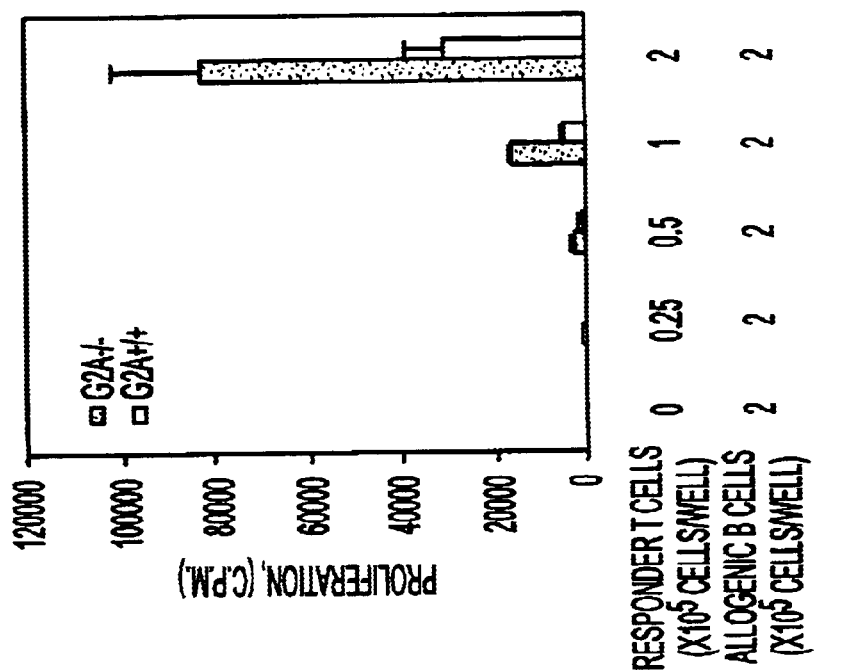
Figure 14A:
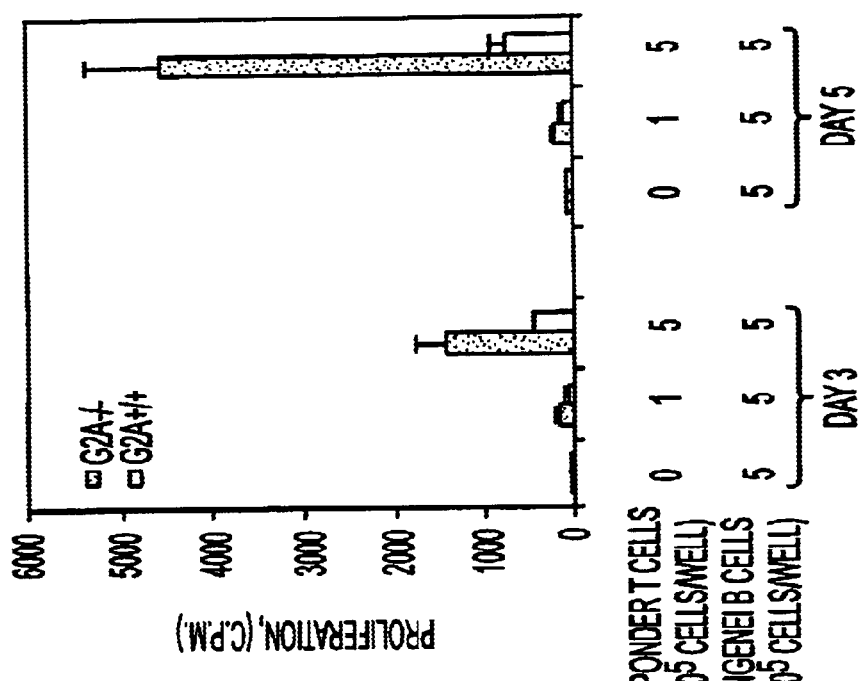

In addition, we performed syngeneic and allogenic mixed lymphocyte reactions (MLRs) using autologous splenic B cells or B6 derived B cells as stimulators respectively (Miyazaki et al., 1997, The EMBO Journal 16:4217–4225). Lymph node derived T cells from G2A-/- mice responded with significantly enhanced proliferation in both syngeneic and allogenic MLRs compared to T cells from wild-type animals (FIGS. 14A, B). Interestingly, the hyperresponsiveness of G2A-/- T cells is even more pronounced in MLRs. This suggests an impact of G2A upon one or more biological processes regulating MHC-dependent T/B cell interaction and immunological activation which are less adequately recapitulated by engagement of TCR and costimulatory receptors by plate-bound antibodies. Importantly, proliferative responses of wild-type T cells ate negligible in syngeneic MLRs, while those of G2A-/- T cells are high, suggesting that autoreactive T cells are present in G2A-/- animals (Bachmaier et al., 2000, Nature 403:211–216).

The responsiveness of G2A-/- T cells to suboptimal concentrations of anti-CD3ε antibody suggests that the activation thresholds of antigen receptors may be altered in G2A-/- T cells. To explore this issue further, we performed kinetic experiments in which [$^3$H]-Thymidine was added to T cells at various time-points following deposition onto anti-CD3ε antibody coated plates. These studies revealed that proliferative responses of G2A-/- T cells are not only greater, but occur at earlier time-points compared to wild-type T cells when stimulated with equivalent concentrations of anti-CD3ε antibody (FIG. 14C). This suggest that activation thresholds are lower in G2A-/- T cells. Expression of the high affinity IL-2 receptor (CD25α) is equivalent in wild-type and G2A-/- T cells before and after stimulation, suggesting that increased responsiveness to sub-optimal concentrations of IL-2 does not account for this kinetic difference. In addition, expression of the T cell early activation marker, CD69, is comparable between wild-type and G2A-/- T cells prior to and 12 to 48 hours following activation, suggesting that hyperresponsiveness of G2A-/- T cells is not associated with an "activated" phenotype.

An essential role for the orphan GPCR, G2A, in homeostatic mechanisms regulating lymphocyte numbers is demonstrated by the development of lymphadenopathy and autoimmune disease in older G2A-/- animals. Although the molecular basis underlying the hyperresponsiveness of G2A-/- T lymphocytes to TCR stimulation is presently unknown, several possible explanations can be proposed based on our knowledge of the biological properties of G2A. G2A activates RhoA leading to actin rearrangement via Gα13 (Kabarowski et al., 2000, Proceedings of the National Academy of Arts and Sciences 97:12109–12114), suggesting that G2A may function to regulate the most proximal events of T lymphocyte activation, perhaps at the level of TCR/cytoskeleton interaction. This hypothesis is further supported, albeit indirectly, by the more pronounced hyperproliferative responses of G2A-/- T cells elicited by MHC stimulation in MLRs compared to those induced by antibody mediated CD3/TCR crosslinking or CD3/CD28 costimulation. As in vitro experimental correlates of antigenic TCR activation, T cell stimulation by cell-bound MHC in MLRs can be considered more physiological than that induced by antibody mediated TCR crosslinking. While both systems recapitulate events associated with immunological synapse formation, namely assembly of receptor clusters and signaling molecules, cell-cell contact in MLRs introduces additional key processes which may be influenced by loss of G2A function. Based on our knowledge of signal transduction events downstream of G2A (Kabarowski et al., 2000, Proceedings of the National Academy of Arts and Sciences 97:12109–12114), engagement of integrin receptors and cytoskeletal reorganisation may be one such process. We are currently exploring the possibility that G2A influences formation of the immunological synapse between the T cell and antigen presenting cell (APC). This process is critically dependent upon cytoskeletal reorganization during which clustering of membrane microdomains (lipid rafts) compartmentalises downstream signal transduction molecules to modify the signaling response (Anton van der Merwe et al., 2000, Seminars in Immunology 12:5–21; Langlet et al., 2000, Current Opinion in Immunology 12:250–255).

The normal development and distribution of CD4$^+$ CD8$^+$, CD4$^-$ CD8$^-$, CD4$^+$ and CD8$^+$ T cells in the thymus of G2A-/- mice suggests that mechanisms governing positive and negative selection involved in central tolerance are not responsible for the emergence of autoimmunity.

Additionally, the major pathological features of the autoimmune syndrome emerging in G2A-/- animals are most similar to the human disease Systemic Lupus Erythematosus (SLE) (Nishimura et al., 1999, Immunity 11:141–151). An important question, therefore, is how the hyperresponsiveness of G2A-/- T cells to TCR crosslinking in vitro relates to this late-onset lymphoproliferative autoimmune syndrome which develops in vivo. Compared to G2A-/- mice, overt lymphoproliferative disease and autoimmunity develops relatively early in mice with targeted disruptions of genes encoding CBL-B, CTLA4, FAS (CD95) or FAS Ligand, consistent with their roles as direct regulators of proliferative and apoptotic pathways in activated T cells (Bachmaiet et al., 2000, Nature 403:211–216; Chiang et al., 2000, Nature 403:216–220; Jacobson et al., 1995, Immunity 3:509–519; Tivol et al., 1995, Immunity 3:541–547). Importantly, the rate and extent of apoptosis in TCR stimulated cultures of wild-type and G2A-/- T cells are indistinguishable, demonstrating that increased thymidine incorporation in the latter is not the result of suppressed activation induced apoptosis but rather increased cycling. Thus, it is possible that deregulated proliferative responses of T cells subverts normal peripheral tolerance mechanisms in G2A-/- mice, resulting in the expansion of autoreactive T cells, which in turn activate autoreactive B cells. In this respect, thresholds of TCRs are primary determinants of the outcome following encounter with self-antigens: tolerance or immunological activation (Van Parijs and Abbas, 1998, Science 280:243–248). Certainly, the proliferative responses of G2A-/- T cells in syngeneic MLRs suggests that autoreactive T cells are present in G2A-/- mice Bachmaier et al., 2000, Nature 403:211–216).

As a unique animal model of late-onset autoimmunity, G2A-deficient mice contribute to our understanding of the pathogenesis of human autoimmune and other immunological disorders. In addition, the suitability of GPCRs as targets of drug based therapeutic intervention promises that farther characterization of G2A function in T lymphocytes and identification of it's ligand may uncover clinical benefits of modulating G2A activity in the treatment of autoimmune disease.

Throughout this application, various publications are referenced (within parentheses for example). The disclosures of these publications are hereby incorporated by reference herein in their entireties. The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention. However, the invention is only limited by the scope of the appended claims.

What is claimed is:

```
                            SEQUENCE LISTING

<160> NUMBER OF SEQ ID NOS: 11

<210> SEQ ID NO 1
<211> LENGTH: 1507
<212> TYPE: DNA
<213> ORGANISM: Mus musculis
<220> FEATURE:
<221> NAME/KEY: CDS
<222> LOCATION: (147)...(1292)

<400> SEQUENCE: 1
aaacctccca gctgggcctg cagagggtg ctcagccctg cctcaggacg ggcctgccct      60
gtgctgcctc aggactggct tgggtcattt taagctgcca gagccacctt cacaagggggg  120 tccacagaac tcacatagga gccacc atg aga tca gaa cct acc aat gca gca   173
                             Met Arg Ser Glu Pro Thr Asn Ala Ala
                               1               5 gga aac acc aca ctg ggg gtt acc tcc gtt ctt cag agc acc tca gta    221
Gly Asn Thr Thr Leu Gly Val Thr Ser Val Leu Gln Ser Thr Ser Val
 10              15                  20                  25 cct tct tct gag acc tgc cac gtc tcc tac gag gag agc aga gtg gtc   269
Pro Ser Ser Glu Thr Cys His Val Ser Tyr Glu Glu Ser Arg Val Val
                 30                  35                  40 ctg gtg gtg gtg tac agt gcc gtg tgc ctg ctg ggc cta cca gcc aac   317
Leu Val Val Val Tyr Ser Ala Val Cys Leu Leu Gly Leu Pro Ala Asn
             45                  50                  55 tgc ctg act gcc tgg ctg acg ctg ctg caa gtc ctg cag agg aac gtg   365
Cys Leu Thr Ala Trp Leu Thr Leu Leu Gln Val Leu Gln Arg Asn Val
         60                  65                  70 cta gcc gtc tac ctg ttc tgc ctg tcc ctc tgt gag ctg ctc tac atc   413
Leu Ala Val Tyr Leu Phe Cys Leu Ser Leu Cys Glu Leu Leu Tyr Ile
     75                  80                  85 agc acg gtg cca ttg tgg atc atc tac atc cag aat cag cac aaa tgg   461
Ser Thr Val Pro Leu Trp Ile Ile Tyr Ile Gln Asn Gln His Lys Trp
 90                  95                 100                 105 aac ctg ggt ccg cag gcc tgc aag gtg act gct tac atc ttc ttc tgc   509
Asn Leu Gly Pro Gln Ala Cys Lys Val Thr Ala Tyr Ile Phe Phe Cys
                110                 115                 120 aac atc tac atc agc atc ctc ttg ctc tgc tgc att tcc tgc gac cgc   557
Asn Ile Tyr Ile Ser Ile Leu Leu Cys Cys Ile Ser Cys Asp Arg
                125                 130                 135 tac atg gcc gtg gtc tat gca ctg gag agc cga ggc cac cgc cac cag   605
Tyr Met Ala Val Val Tyr Ala Leu Glu Ser Arg Gly His Arg His Gln
            140                 145                 150 agg act gct gtc acc att tct gcg tgt gtg att ctt ctt gtt gga ctt   653
Arg Thr Ala Val Thr Ile Ser Ala Cys Val Ile Leu Leu Val Gly Leu
        155                 160                 165 gtt aac tat cca gtg ttt gac atg aag gtg gag aag agt ttc tgc ttt   701
Val Asn Tyr Pro Val Phe Asp Met Lys Val Glu Lys Ser Phe Cys Phe
170                 175                 180                 185 gag ccc ctg agg atg aac agc aag ata gcc ggc tac cac tac ctg cgt   749
Glu Pro Leu Arg Met Asn Ser Lys Ile Ala Gly Tyr His Tyr Leu Arg
                190                 195                 200 ttc acc ttt ggc ttt gcc atc cct ctc ggc atc ctg gcg ttc acc aat   797
Phe Thr Phe Gly Phe Ala Ile Pro Leu Gly Ile Leu Ala Phe Thr Asn
                205                 210                 215 cac cag atc ttc cgg agc atc aaa ctc agt gac agc ctg agc gct gcg   845
His Gln Ile Phe Arg Ser Ile Lys Leu Ser Asp Ser Leu Ser Ala Ala
```

```
           220                 225                 230
cag aag aac aag gtg aag cgc tcc gcc atc gcg gtc gtc acc atc ttc      893
Gln Lys Asn Lys Val Lys Arg Ser Ala Ile Ala Val Val Thr Ile Phe
    235                 240                 245 ctg gtc tgc ttt gct ccc tac cac gtg gta ctc ctc gtc aaa gct gcc      941
Leu Val Cys Phe Ala Pro Tyr His Val Val Leu Leu Val Lys Ala Ala
250                 255                 260                 265 agc ttt tcc ttc tac caa gga gac atg gat gcc gtg tgt gcc ttt gaa      989
Ser Phe Ser Phe Tyr Gln Gly Asp Met Asp Ala Val Cys Ala Phe Glu
                270                 275                 280 agc aga ctg tac aca gtc tct atg gtg ttt ctg tgc ctg tct aca gtc     1037
Ser Arg Leu Tyr Thr Val Ser Met Val Phe Leu Cys Leu Ser Thr Val
            285                 290                 295 aac agt gtg gct gac ccc atc atc tac gtg ctg ggt aca gac cac tct     1085
Asn Ser Val Ala Asp Pro Ile Ile Tyr Val Leu Gly Thr Asp His Ser
        300                 305                 310 cgg caa gaa gtg tcc aga atc cac aca ggg tgg aaa aag tgg tcc aca     1133
Arg Gln Glu Val Ser Arg Ile His Thr Gly Trp Lys Lys Trp Ser Thr
    315                 320                 325 aag aca tat gtt aca tgc tca aag gac tct gag gag aca cac ttg ccc     1181
Lys Thr Tyr Val Thr Cys Ser Lys Asp Ser Glu Glu Thr His Leu Pro
330                 335                 340                 345 aca gag ctt tca aac aca tac acc ttc ccc aat ccc gcg cac cct cca     1229
Thr Glu Leu Ser Asn Thr Tyr Thr Phe Pro Asn Pro Ala His Pro Pro
                350                 355                 360 gga tca cag cca gcg aag cta ggt tta ctg tgc tcg cca gag aga ctg     1277
Gly Ser Gln Pro Ala Lys Leu Gly Leu Leu Cys Ser Pro Glu Arg Leu
            365                 370                 375 cct gag gag ctc tgc taagagacga ttgtccactc ttcctcaaaa ctagcaccag     1332
Pro Glu Glu Leu Cys
            380 tcacacatac ctggtcctct gagtcaccgt ctggggtgtc cacagcacta tagatgcctt     1392 tgttcgggca cacgctgctg atctttcctt cctaaggcca ccaactctga aagtatctgt     1452 tccttaaact gtcctcaggc tccctctat ggaaagcggg gcttgctaag ggacc           1507

<210> SEQ ID NO 2
<211> LENGTH: 382
<212> TYPE: PRT
<213> ORGANISM: Mus musculis

<400> SEQUENCE: 2

Met Arg Ser Glu Pro Thr Asn Ala Ala Gly Asn Thr Thr Leu Gly Val
 1               5                  10                  15

Thr Ser Val Leu Gln Ser Thr Ser Val Pro Ser Ser Glu Thr Cys His
                20                  25                  30

Val Ser Tyr Glu Glu Ser Arg Val Val Leu Val Val Tyr Ser Ala
            35                  40                  45

Val Cys Leu Leu Gly Leu Pro Ala Asn Cys Leu Thr Ala Trp Leu Thr
50                  55                  60

Leu Leu Gln Val Leu Gln Arg Asn Val Leu Ala Val Tyr Leu Phe Cys
65                  70                  75                  80

Leu Ser Leu Cys Glu Leu Leu Tyr Ile Ser Thr Val Pro Leu Trp Ile
                85                  90                  95

Ile Tyr Ile Gln Asn Gln His Lys Trp Asn Leu Gly Pro Gln Ala Cys
            100                 105                 110

Lys Val Thr Ala Tyr Ile Phe Phe Cys Asn Ile Tyr Ile Ser Ile Leu
        115                 120                 125
```

-continued

```
Leu Leu Cys Cys Ile Ser Cys Asp Arg Tyr Met Ala Val Val Tyr Ala
    130                 135                 140
Leu Glu Ser Arg Gly His Arg His Gln Arg Thr Ala Val Thr Ile Ser
145                 150                 155                 160
Ala Cys Val Ile Leu Leu Val Gly Leu Val Asn Tyr Pro Val Phe Asp
                165                 170                 175
Met Lys Val Glu Lys Ser Phe Cys Phe Glu Pro Leu Arg Met Asn Ser
            180                 185                 190
Lys Ile Ala Gly Tyr His Tyr Leu Arg Phe Thr Phe Gly Phe Ala Ile
        195                 200                 205
Pro Leu Gly Ile Leu Ala Phe Thr Asn His Gln Ile Phe Arg Ser Ile
    210                 215                 220
Lys Leu Ser Asp Ser Leu Ser Ala Ala Gln Lys Asn Lys Val Lys Arg
225                 230                 235                 240
Ser Ala Ile Ala Val Val Thr Ile Phe Leu Val Cys Phe Ala Pro Tyr
                245                 250                 255
His Val Val Leu Leu Val Lys Ala Ala Ser Phe Ser Phe Tyr Gln Gly
            260                 265                 270
Asp Met Asp Ala Val Cys Ala Phe Glu Ser Arg Leu Tyr Thr Val Ser
        275                 280                 285
Met Val Phe Leu Cys Leu Ser Thr Val Asn Ser Val Ala Asp Pro Ile
    290                 295                 300
Ile Tyr Val Leu Gly Thr Asp His Ser Arg Gln Glu Val Ser Arg Ile
305                 310                 315                 320
His Thr Gly Trp Lys Lys Trp Ser Thr Lys Thr Tyr Val Thr Cys Ser
                325                 330                 335
Lys Asp Ser Glu Glu Thr His Leu Pro Thr Glu Leu Ser Asn Thr Tyr
            340                 345                 350
Thr Phe Pro Asn Pro Ala His Pro Gly Ser Gln Pro Ala Lys Leu
        355                 360                 365
Gly Leu Leu Cys Ser Pro Glu Arg Leu Pro Glu Leu Cys
    370                 375                 380

<210> SEQ ID NO 3
<211> LENGTH: 2938
<212> TYPE: DNA
<213> ORGANISM: Homo sapiens
<220> FEATURE:
<221> NAME/KEY: CDS
<222> LOCATION: (901)...(2040)
<223> OTHER INFORMATION: n = a, c, t, or g

<400> SEQUENCE: 3 gggagggtg cnangctagc cacgcaggcg gggccctggg tcattttaan ctctcagagt      60
gaacgtcttg ataggaccga caanacncat nacntgtact tagatagctt atcttananc    120
cacnctgana ttggaacccg caaaatatgc cngggaggaa ggtgagcaag ggacacgaca    180
ctcacccgga taaacccaac aagcgcagcg aggctgtggg gaaaccggan ccctgcacac    240
cgccggggga aggtgggcen ccgccaccac cgtggaagaa cagcgcggan caccccacg     300 agatgagacg gaactgccgt gagatccagc aatccnact gtgggtctga cccaggatan    360
cggaaagcag ggacgtgaac agccctcctc atgttcttga caccgtcatt ctcagcagct    420
cagctaaggc acagaggcag ccgagcgtct gtcagcagag tcgtggctga gcagaacacg    480
ccacacgcca cacgccacac gccacacgtg caggattgct caagatggaa gggcacagtg    540
```

-continued

```
gaatatatat atatatttat attttttggcg agaccctgga ggacacactg aatacaatgg      600 ataccatcc cgcctttgaa aggaagggaa atcctggcac acgctgcaac aggagggagc       660
ttgaggacac tgtggtgagt ggagcacgtg agacacggaa ggacacacgc tgaagacacg      720
cagagatgcc cacccacgtg gggaggtgac aggggagccc agcgcacaga gacaaagtgg      780
aatggaggcc tggggctgg gagcaaatgc ggagcgagtg cttcctgggg cagagtctcc       840
gtttgggaag atgagaaggt tctgccgacg gatgctggcg atggttgcag aagaatgtga     900
```

| | | | | | | | | | | | | | | | | |
|---|---|---|---|---|---|---|---|---|---|---|---|---|---|---|---|---|
| atg | tgc | cca | atg | cta | ctg | aaa | aac | ggt | tac | aat | gga | aac | gcc | acc | cca | 948 |
| Met | Cys | Pro | Met | Leu | Leu | Lys | Asn | Gly | Tyr | Asn | Gly | Asn | Ala | Thr | Pro | |
| 1 | | | 5 | | | | | 10 | | | | | 15 | | | |

| gtg | acc | acc | act | gcc | ccg | tgg | gcc | tcc | ctg | ggc | ctc | tcc | gcc | aag | acc | 996 |
|---|---|---|---|---|---|---|---|---|---|---|---|---|---|---|---|---|
| Val | Thr | Thr | Thr | Ala | Pro | Trp | Ala | Ser | Leu | Gly | Leu | Ser | Ala | Lys | Thr | |
| | | 20 | | | | | 25 | | | | | 30 | | | | |

| tgc | aac | aac | gtg | tcc | ttc | gaa | gag | agc | agg | ata | gtc | ctg | gtc | gtg | gtg | 1044 |
|---|---|---|---|---|---|---|---|---|---|---|---|---|---|---|---|---|
| Cys | Asn | Asn | Val | Ser | Phe | Glu | Glu | Ser | Arg | Ile | Val | Leu | Val | Val | Val | |
| | 35 | | | | | 40 | | | | | 45 | | | | | |

| tac | agc | gcg | gtg | tgc | acg | ctg | ggg | gtg | ccg | gcc | aac | tgc | ctg | act | gcg | 1092 |
|---|---|---|---|---|---|---|---|---|---|---|---|---|---|---|---|---|
| Tyr | Ser | Ala | Val | Cys | Thr | Leu | Gly | Val | Pro | Ala | Asn | Cys | Leu | Thr | Ala | |
| 50 | | | | | 55 | | | | | 60 | | | | | | |

| tgg | ctg | gcg | ctg | ctg | cag | gta | ctg | cag | ggc | aac | gtg | ctg | gcc | gtc | tac | 1140 |
|---|---|---|---|---|---|---|---|---|---|---|---|---|---|---|---|---|
| Trp | Leu | Ala | Leu | Leu | Gln | Val | Leu | Gln | Gly | Asn | Val | Leu | Ala | Val | Tyr | |
| 65 | | | | 70 | | | | | 75 | | | | | 80 | | |

| ctg | ctc | tgc | ctg | gca | ctc | tgc | gag | ctg | ctg | tac | aca | ggc | acg | ctg | cca | 1188 |
|---|---|---|---|---|---|---|---|---|---|---|---|---|---|---|---|---|
| Leu | Leu | Cys | Leu | Ala | Leu | Cys | Glu | Leu | Leu | Tyr | Thr | Gly | Thr | Leu | Pro | |
| | | | 85 | | | | | 90 | | | | | 95 | | | |

| ctc | tgg | gtc | atc | tat | atc | cgc | aac | cag | cac | cgc | tgg | acc | cta | ggc | ctg | 1236 |
|---|---|---|---|---|---|---|---|---|---|---|---|---|---|---|---|---|
| Leu | Trp | Val | Ile | Tyr | Ile | Arg | Asn | Gln | His | Arg | Trp | Thr | Leu | Gly | Leu | |
| | | 100 | | | | | 105 | | | | | 110 | | | | |

| ctg | gcc | tgc | aag | gtg | acc | gcc | tac | atc | ttc | ttc | tgc | aac | atc | tac | gtc | 1284 |
|---|---|---|---|---|---|---|---|---|---|---|---|---|---|---|---|---|
| Leu | Ala | Cys | Lys | Val | Thr | Ala | Tyr | Ile | Phe | Phe | Cys | Asn | Ile | Tyr | Val | |
| | | 115 | | | | | 120 | | | | | 125 | | | | |

| agc | atc | ctc | ttc | ctg | tgc | tgc | atc | tcc | tgc | gac | cgc | ttc | gtg | gcc | gtg | 1332 |
|---|---|---|---|---|---|---|---|---|---|---|---|---|---|---|---|---|
| Ser | Ile | Leu | Phe | Leu | Cys | Cys | Ile | Ser | Cys | Asp | Arg | Phe | Val | Ala | Val | |
| | 130 | | | | | 135 | | | | | 140 | | | | | |

| gtg | tac | gcg | ctg | gag | agt | cgg | ggc | cgc | cgc | cgc | cgg | agg | acc | gcc | atc | 1380 |
|---|---|---|---|---|---|---|---|---|---|---|---|---|---|---|---|---|
| Val | Tyr | Ala | Leu | Glu | Ser | Arg | Gly | Arg | Arg | Arg | Arg | Arg | Thr | Ala | Ile | |
| 145 | | | | 150 | | | | | 155 | | | | | 160 | | |

| ctc | atc | tcc | gcc | tgc | atc | ttc | atc | ctc | gtc | ggg | atc | gtt | cac | tac | ccg | 1428 |
|---|---|---|---|---|---|---|---|---|---|---|---|---|---|---|---|---|
| Leu | Ile | Ser | Ala | Cys | Ile | Phe | Ile | Leu | Val | Gly | Ile | Val | His | Tyr | Pro | |
| | | | 165 | | | | | 170 | | | | | 175 | | | |

| gtg | ttc | cag | acg | gaa | gac | aag | gag | acc | tgc | ttt | gac | atg | ctg | cag | atg | 1476 |
|---|---|---|---|---|---|---|---|---|---|---|---|---|---|---|---|---|
| Val | Phe | Gln | Thr | Glu | Asp | Lys | Glu | Thr | Cys | Phe | Asp | Met | Leu | Gln | Met | |
| | | | 180 | | | | | 185 | | | | | 190 | | | |

| gac | agc | agg | att | gcc | ggg | tac | tac | tac | gcc | agg | ttc | acc | gtt | ggc | ttt | 1524 |
|---|---|---|---|---|---|---|---|---|---|---|---|---|---|---|---|---|
| Asp | Ser | Arg | Ile | Ala | Gly | Tyr | Tyr | Tyr | Ala | Arg | Phe | Thr | Val | Gly | Phe | |
| | | 195 | | | | | 200 | | | | | 205 | | | | |

| gcc | atc | cct | ctc | tcc | atc | atc | gcc | ttc | acc | aac | cac | cgg | att | ttc | agg | 1572 |
|---|---|---|---|---|---|---|---|---|---|---|---|---|---|---|---|---|
| Ala | Ile | Pro | Leu | Ser | Ile | Ile | Ala | Phe | Thr | Asn | His | Arg | Ile | Phe | Arg | |
| | 210 | | | | | 215 | | | | | 220 | | | | | |

| agc | atc | aag | cag | agc | atg | ggc | tta | agc | gct | gcc | cag | aag | gcc | aag | gtg | 1620 |
|---|---|---|---|---|---|---|---|---|---|---|---|---|---|---|---|---|
| Ser | Ile | Lys | Gln | Ser | Met | Gly | Leu | Ser | Ala | Ala | Gln | Lys | Ala | Lys | Val | |
| 225 | | | | 230 | | | | | 235 | | | | | 240 | | |

| aag | cac | tcg | gcc | atc | gcg | gtg | gtt | gtc | atc | ttc | cta | gtc | tgc | ttc | gcc | 1668 |
|---|---|---|---|---|---|---|---|---|---|---|---|---|---|---|---|---|
| Lys | His | Ser | Ala | Ile | Ala | Val | Val | Val | Ile | Phe | Leu | Val | Cys | Phe | Ala | |
| | | | 245 | | | | | 250 | | | | | 255 | | | |

| ccg | tac | cac | ctg | gtt | ctc | ctc | gtc | aaa | gcc | gct | gcc | ttt | tcc | tac | tac | 1716 |
|---|---|---|---|---|---|---|---|---|---|---|---|---|---|---|---|---|
| Pro | Tyr | His | Leu | Val | Leu | Leu | Val | Lys | Ala | Ala | Ala | Phe | Ser | Tyr | Tyr | |
| | | 260 | | | | | 265 | | | | | 270 | | | | |

-continued

| | |
|---|---|
| aga gga gac agg aac gcc atg tgc ggc ttg gag gaa agg ctg tac aca<br>Arg Gly Asp Arg Asn Ala Met Cys Gly Leu Glu Glu Arg Leu Tyr Thr<br>                275                          280                        285 | 1764 |
| gcc tct gtg gtg ttt ctg tgc ctg tcc acg gtg aac ggc gtg gct gac<br>Ala Ser Val Val Phe Leu Cys Leu Ser Thr Val Asn Gly Val Ala Asp<br>        290                          295                        300 | 1812 |
| ccc att atc tac gtg ctg gcc acg gac cat tcc cgc caa gaa gtg tcc<br>Pro Ile Ile Tyr Val Leu Ala Thr Asp His Ser Arg Gln Glu Val Ser<br>305                      310                        315                        320 | 1860 |
| aga atc cat aag ggg tgg aaa gag tgg tcc atg aag aca gac gtc acc<br>Arg Ile His Lys Gly Trp Lys Glu Trp Ser Met Lys Thr Asp Val Thr<br>                          325                        330                        335 | 1908 |
| agg ctc acc cac agc agg gac acc gag gag ctg cag tcg ccc gtg gcc<br>Arg Leu Thr His Ser Arg Asp Thr Glu Glu Leu Gln Ser Pro Val Ala<br>                  340                        345                        350 | 1956 |
| ctt gca gac cac tac acc ttc tcc agg ccc gtg cac cca cca ggg tca<br>Leu Ala Asp His Tyr Thr Phe Ser Arg Pro Val His Pro Pro Gly Ser<br>        355                          360                        365 | 2004 |
| cca tgc cct gca aag agg ctg att gag gag tcc tgc tgagcccact<br>Pro Cys Pro Ala Lys Arg Leu Ile Glu Glu Ser Cys<br>370                    375                    380 | 2050 |
| gtgtggcagg gggatggcag gttgggggtc ctggggccag caatgtggtt cctgtgcact | 2110 |
| gagcccacca gccacagtgc ccatgtcccc tctggaagac aaactaccaa tttctcgttc | 2170 |
| ctgaagccac tccctccgtg accactggcc ccangctttc ccacatggaa ggtggctgca | 2230 |
| tgccaagggg aagaacgaca cctccaggct tccgggagcc cananancat gtggcangca | 2290 |
| gtggggcctc ttcatcatca ncctgcctgg ctggctccct tggctgtggg cangtacacc | 2350 |
| cctgctggca naagtacctg gtggctgccc tgttcgcatc antggcgatn actttatttg | 2410 |
| cggagcattt ctgcaancgt tgcctggatn cggtggtgca ttgtgggccc tctgggctcc | 2470 |
| tgcctcaaaa tgtcagtgan caccatgctg gaagtcacca tcactgtggc ancgcccang | 2530 |
| aaggcatang gcacctacca cctccaaggg ggcangcgcc ctcatctggg gttgggtctn | 2590 |
| ttgctgaact gggaaggcct ctangggaac cctggggcan ggtggccaac tgctngctcc | 2650 |
| canaaaccaa cccaaggcgt ctcaacgggg gaaccccaaa tgttcncgcc ccanaaaaaa | 2710 |
| caattttngg aagganaagt tnttaaacac cccncncca naagccaagg ggttcccagg | 2770 |
| aaattcccca ccggcatcct ccggggaaaa nactcggtna angggtccct tacaagggtt | 2830 |
| ggggttccc cnccctaac cccnttaat tgaagggggg gaaattcaac ccttttggcc | 2890 |
| tcctttttt ttgcggnaaa aaaacaacn tccctgcan ccccggn | 2938 |

<210> SEQ ID NO 4
<211> LENGTH: 380
<212> TYPE: PRT
<213> ORGANISM: Homo sapiens

<400> SEQUENCE: 4

Met Cys Pro Met Leu Leu Lys Asn Gly Tyr Asn Gly Asn Ala Thr Pro
1               5                    10                   15

Val Thr Thr Thr Ala Pro Trp Ala Ser Leu Gly Leu Ser Ala Lys Thr
                  20                    25                    30

Cys Asn Asn Val Ser Phe Glu Glu Ser Arg Ile Val Leu Val Val Val
              35                    40                    45

Tyr Ser Ala Val Cys Thr Leu Gly Val Pro Ala Asn Cys Leu Thr Ala
    50                    55                    60

-continued

```
Trp Leu Ala Leu Leu Gln Val Leu Gln Gly Asn Val Leu Ala Val Tyr
 65                  70                  75                  80

Leu Leu Cys Leu Ala Leu Cys Glu Leu Tyr Thr Gly Thr Leu Pro
                 85                  90                  95

Leu Trp Val Ile Tyr Ile Arg Asn Gln His Arg Trp Thr Leu Gly Leu
                100                 105                 110

Leu Ala Cys Lys Val Thr Ala Tyr Ile Phe Phe Cys Asn Ile Tyr Val
            115                 120                 125

Ser Ile Leu Phe Leu Cys Cys Ile Ser Cys Asp Arg Phe Val Ala Val
            130                 135                 140

Val Tyr Ala Leu Glu Ser Arg Gly Arg Arg Arg Arg Thr Ala Ile
145                 150                 155                 160

Leu Ile Ser Ala Cys Ile Phe Ile Leu Val Gly Ile Val His Tyr Pro
                165                 170                 175

Val Phe Gln Thr Glu Asp Lys Glu Thr Cys Phe Asp Met Leu Gln Met
                180                 185                 190

Asp Ser Arg Ile Ala Gly Tyr Tyr Ala Arg Phe Thr Val Gly Phe
            195                 200                 205

Ala Ile Pro Leu Ser Ile Ile Ala Phe Thr Asn His Arg Ile Phe Arg
210                 215                 220

Ser Ile Lys Gln Ser Met Gly Leu Ser Ala Ala Gln Lys Ala Lys Val
225                 230                 235                 240

Lys His Ser Ala Ile Ala Val Val Val Ile Phe Leu Val Cys Phe Ala
                245                 250                 255

Pro Tyr His Leu Val Leu Val Lys Ala Ala Ala Phe Ser Tyr Tyr
            260                 265                 270

Arg Gly Asp Arg Asn Ala Met Cys Gly Leu Glu Glu Arg Leu Tyr Thr
            275                 280                 285

Ala Ser Val Val Phe Leu Cys Leu Ser Thr Val Asn Gly Val Ala Asp
290                 295                 300

Pro Ile Ile Tyr Val Leu Ala Thr Asp His Ser Arg Gln Glu Val Ser
305                 310                 315                 320

Arg Ile His Lys Gly Trp Lys Glu Trp Ser Met Lys Thr Asp Val Thr
                325                 330                 335

Arg Leu Thr His Ser Arg Asp Thr Glu Glu Leu Gln Ser Pro Val Ala
            340                 345                 350

Leu Ala Asp His Tyr Thr Phe Ser Arg Pro Val His Pro Pro Gly Ser
            355                 360                 365

Pro Cys Pro Ala Lys Arg Leu Ile Glu Glu Ser Cys
370                 375                 380

<210> SEQ ID NO 5
<211> LENGTH: 13
<212> TYPE: PRT
<213> ORGANISM: Mus musculis

<400> SEQUENCE: 5

Lys Asp Ser Glu Glu Thr His Leu Pro Thr Glu Leu Ser
 1                   5                  10

<210> SEQ ID NO 6
<211> LENGTH: 21
<212> TYPE: DNA
<213> ORGANISM: Mus musculis

<400> SEQUENCE: 6
```

-continued

```
tagcggtcgc aggaaatgca g                                          21

<210> SEQ ID NO 7
<211> LENGTH: 20
<212> TYPE: DNA
<213> ORGANISM: Mus musculis

<400> SEQUENCE: 7
caggactggc ttgggtcatt                                            20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gcacctgtgg ggaagaaact                                            20

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
tgagagctgt ctcctactat cgat                                       24

<210> SEQ ID NO 10
<211> LENGTH: 31
<212> TYPE: DNA
<213> ORGANISM: Artificial Sequence
<220> FEATURE:
<223> OTHER INFORMATION: Primer

<400> SEQUENCE: 10
agggatcctt gtgaagggat ctactactgt g                               31

<210> SEQ ID NO 11
<211> LENGTH: 26
<212> TYPE: DNA
<213> ORGANISM: Artificial Sequence
<220> FEATURE:
<223> OTHER INFORMATION: Primer

<400> SEQUENCE: 11
aaagacctgc agaggccatt cttacc                                     26
```

1. A method of modulating G2A receptor (FIG. 2, SEQ ID NOS: 2 and 4) mediated signaling in a cell comprising increasing or decreasing the concentration of G2A ligand present in the cell's environment that is capable of binding and activating the G2A receptor.

2. The method of claim 1 wherein G2A receptor mediated signaling is measured by observing an elevation in the concentration of intracellular calcium (−).

3. The method of claim 1 wherein G2A receptor mediated signaling is measured by observing an induction of ERK MAP kinase activation.

4. The method of claim 1 wherein the concentration of G2A ligand present in the cell's environment that is capable of binding to and activating the G2A receptor is increased.

5. The method of claim 2, wherein the concentration of G2A ligand present in the cell's environment that is capable of binding to and activating the G2A receptor is increased by introducing exogenous lysophosphatidylcholine into the cell's environment.

6. The method of claim 2, wherein the concentration of G2A ilgand present in the cell's environment that is capable of binding to and activating the G2A receptor is increased by introducing exogenous sphingosylphosphorylcholine into the cell's environment.

7. The method of claim 1, wherein the concentration of G2A ligand present in the cell's environment that is capable of binding to and activating the G2A receptor is decreased.

8. The method of claim 4, wherein the concentration of G2A ligand present in the cell's environment that is capable of binding to and activating the G2A receptor is decreased by the LPC antagonist choline.

9. The method of claim 1, wherein the G2A ligand is selected from the group consisting of lysophosphatidylcholine and sphingosylphosphorylcholine.

10. A method of modulating LPC mediated activation of a G2A receptor (FIG. 2, SEQ ID NOS: 2 and 4) in a cell comprising increasing or decreasing the concentration of LPC capable of binding to and activating the G2A receptor.

11. The method of claim 10 wherein LPC mediated activation of G2A receptor is measured by observing an elevation in the concentration of intracellular calcium (−).

12. The method of claim 10, wherein the concentration of LPC capable of binding to and activating the G2A receptor is increased by introducing exogenous lysophosphatidylcholine into the cells's environment.

13. The method of claim 10, wherein the concentration of LPC capable of binding to and activating the G2A receptor is decreased by introducing anti-LPC antibody into the cell's environment.

14. A method of modulating SPC mediated activation of a G2A receptor (FIG. 2, SEQ ID NOS: 2 and 4) in a cell comprising increasing or decreasing the concentration of SPC capable of binding to and activating the G2A receptor.

15. The method of claim 14, wherein the concentration of SPC capable of binding to and activating the G2A receptor is decreased by introducing exogenous LPC into the cell's environment.

* * * * *